US006861397B2

(12) United States Patent
Seitz, Jr. et al.

(10) Patent No.: US 6,861,397 B2
(45) Date of Patent: Mar. 1, 2005

(54) COMPOSITIONS HAVING ENHANCED DEPOSITION OF A TOPICALLY ACTIVE COMPOUND ON A SURFACE

(75) Inventors: Earl P. Seitz, Jr., Scottsdale, AZ (US); Andrea Lynn Waggoner, Mesa, AZ (US); Priscilla S. Fox, Phoenix, AZ (US); Timothy J. Taylor, Phoenix, AZ (US)

(73) Assignee: The Dial Corporation, Scottsdale, AZ (US)

( * ) Notice: Subject to any disclaimer, the term of this patent is extended or adjusted under 35 U.S.C. 154(b) by 167 days.

(21) Appl. No.: 10/192,449

(22) Filed: Jul. 10, 2002

(65) Prior Publication Data

US 2003/0125224 A1 Jul. 3, 2003

Related U.S. Application Data

(63) Continuation-in-part of application No. 09/578,020, filed on May 24, 2000, now Pat. No. 6,451,748, which is a continuation of application No. 09/338,654, filed on Jun. 23, 1999, now Pat. No. 6,107,261.

(51) Int. Cl.[7] .................................................. C11D 3/12
(52) U.S. Cl. ..................... 510/119; 510/119; 510/130; 510/136; 510/137; 510/138; 510/394; 510/426; 510/427
(58) Field of Search ................................ 510/119, 130, 510/136, 137, 138, 394, 426, 427

(56) References Cited

U.S. PATENT DOCUMENTS

| | | |
|---|---|---|
| 3,326,808 A | 6/1967 | Noseworthy |
| 3,503,885 A | 3/1970 | Wedell |
| 3,933,671 A | 1/1976 | Heile |
| 4,093,745 A | 6/1978 | Wood et al. |
| 4,111,844 A | 9/1978 | Polony et al. |
| 4,350,605 A | 9/1982 | Hughett |
| 4,518,517 A | 5/1985 | Eigen et al. |
| 4,666,615 A | 5/1987 | Disch et al. |
| 4,675,178 A | 6/1987 | Klein et al. |
| 4,702,916 A | 10/1987 | Geria |
| 4,822,602 A | 4/1989 | Sabatelli |
| 4,832,861 A | 5/1989 | Resch |
| 4,851,214 A | 7/1989 | Walters et al. |
| 4,954,281 A | 9/1990 | Resch |
| 4,975,218 A | 12/1990 | Rosser |
| 5,006,529 A | 4/1991 | Resch |
| 5,057,311 A | 10/1991 | Kamegai et al. |
| 5,147,574 A | 9/1992 | MacGlip et al. |
| 5,158,699 A | 10/1992 | MacGlip et al. |
| 5,234,618 A | 8/1993 | Kamegai et al. |
| 5,288,486 A | 2/1994 | White |
| 5,403,864 A | 4/1995 | Bruch et al. |
| 5,415,810 A | 5/1995 | Lee et al. |
| 5,417,875 A | 5/1995 | Nozaki |
| 5,441,671 A | 8/1995 | Cheney et al. |
| 5,462,736 A | 10/1995 | Rech et al. |
| 5,480,586 A * | 1/1996 | Jakubicki et al. ........... 510/237 |
| 5,539,001 A | 7/1996 | Waldmann-Laue et al. |

(List continued on next page.)

FOREIGN PATENT DOCUMENTS

| | | |
|---|---|---|
| AU | 8930018 | 2/1989 |
| DE | 31 17 792 | 11/1982 |
| DE | 37 23 990 | 2/1988 |
| DE | 37 23 994 | 2/1988 |
| DE | 195 30 833 | 2/1996 |
| EP | 0 259 249 | 3/1988 |
| EP | 0 505 935 | 9/1992 |
| EP | 0 604 848 | 12/1993 |
| EP | 0 855 439 | 7/1998 |
| EP | 0 855 440 | 7/1998 |
| FR | 2 629 095 | 9/1989 |
| GB | 743984 | 1/1956 |
| GB | 1408885 | 10/1975 |
| GB | 1453198 | 10/1976 |
| GB | 2208339 | 10/1988 |
| GB | 2211093 | 6/1989 |
| JP | 1-249897 | 10/1989 |
| JP | 5-279693 | 10/1993 |
| WO | WO 95/09605 | 4/1995 |
| WO | WO 95/32705 | 12/1995 |
| WO | WO 96/06152 | 2/1996 |
| WO | WO 96/06153 | 2/1996 |
| WO | WO 97/46218 | 12/1997 |
| WO | WO 98/01110 | 1/1998 |
| WO | WO 98/21955 | 5/1998 |
| WO | WO 98/32821 | 7/1998 |
| WO | WO 98/55092 | 12/1998 |
| WO | WO 98/55096 | 12/1998 |
| WO | WO 98/55097 | 12/1998 |
| WO | WO 99/25800 | 5/1999 |

OTHER PUBLICATIONS

Allawala et al., *Journal of the American Phramaceutical Association*, vol. XLII, No. 5, pp. 267–275 (1953).

Mitchell, *J. Pharm. Pharmacol.*, 16, pp. 533–537 (1964).

Kjaerheim et al., *Chemical Abstracts*, 122, No. 2, Abstract No. 16825 (1995).

No author, "Deblocking systems, surfactants, and irgasan," 14 pages.

No author, "Highly effective broad–spectrum antimicrobial with a potent, rapid microbicidal action and remanent effect for incorporation in hand disinfectants," Ciba–Geigy brochure, 15 pages. (Oct. 3, 1990).

*Primary Examiner*—Charles Boyer
(74) *Attorney, Agent, or Firm*—Marshall, Gerstein & Borun LLP

(57) ABSTRACT

Topically active compositions having enhanced effectiveness are disclosed. The compositions contain a topically active compound, an anionic surfactant, a hydric solvent, a hydrotrope, an optional cosurfactant, and water, wherein a percent saturation of the topical active compound of the composition is at least 25%. The compositions exhibit a rapid and effective topical effect, and effectively deposit the topically active compound for an effective residual effect.

15 Claims, No Drawings

U.S. PATENT DOCUMENTS

| | | | | |
|---|---|---|---|---|
| 5,635,462 | A | 6/1997 | Fendler et al. | |
| 5,635,469 | A | 6/1997 | Fowler et al. | |
| 5,646,100 | A | 7/1997 | Haugk et al. | |
| 5,653,970 | A | 8/1997 | Vermeer | |
| 5,681,802 | A | 10/1997 | Fujiwara et al. | |
| 5,716,626 | A | 2/1998 | Sakurai et al. | |
| 5,728,756 | A | 3/1998 | Gaffar et al. | |
| 5,730,963 | A | 3/1998 | Hilliard, Jr. et al. | |
| 5,816,446 | A * | 10/1998 | Steindorf et al. | 222/1 |
| 5,824,650 | A | 10/1998 | DeLacharriere et al. | |
| 5,837,272 | A | 11/1998 | Fierro, Jr. et al. | |
| 5,851,974 | A * | 12/1998 | Sandhu | 510/235 |
| 5,863,524 | A | 1/1999 | Mason et al. | |
| 5,871,718 | A | 2/1999 | Lucas et al. | |
| 5,888,524 | A | 3/1999 | Cole | |
| 5,905,066 | A | 5/1999 | Zocchi et al. | |
| 5,919,438 | A | 7/1999 | Saint-Leger | |
| 5,955,408 | A | 9/1999 | Kaiser et al. | |
| 5,968,539 | A | 10/1999 | Beerse et al. | |
| 5,985,294 | A | 11/1999 | Peffly | |
| 5,994,286 | A | 11/1999 | Desai et al. | |
| 6,057,274 | A | 5/2000 | Bator | |
| 6,071,541 | A | 6/2000 | Murad | |
| 6,107,261 | A * | 8/2000 | Taylor et al. | 510/131 |
| 6,147,120 | A | 11/2000 | Swart et al. | |
| 6,184,190 | B1 * | 2/2001 | D'Ambrogio et al. | 510/130 |
| 6,204,230 | B1 * | 3/2001 | Taylor et al. | 510/131 |
| 6,291,419 | B1 * | 9/2001 | D'Ambrogio et al. | 510/425 |
| 6,451,748 | B1 * | 9/2002 | Taylor et al. | 510/131 |
| 6,531,434 | B1 * | 3/2003 | Gluck | 510/131 |
| 6,699,824 | B1 * | 3/2004 | Dawson et al. | 510/130 |

* cited by examiner

COMPOSITIONS HAVING ENHANCED DEPOSITION OF A TOPICALLY ACTIVE COMPOUND ON A SURFACE

CROSS-REFERENCE TO RELATED APPLICATION

This application is a continuation-in-part of U.S. application Ser. No. 09/578,020, filed May 24, 2000, now U.S. Pat. No. 6,451,748, which is a continuation of U.S. application Ser. No. 09/338,654, filed Jun. 23, 1999, now U.S. Pat. No. 6,107,261.

FIELD OF THE INVENTION

The present invention is directed to compositions, particularly personal care compositions, having an improved ability to deposit topically active compounds on a surface, such as skin or hair. More particularly, the present invention is directed to compositions comprising a topically active compound, a primary surfactant, a hydrotrope, a hydric solvent, an optional cosurfactant, and other optional ingredients. The topically active compounds include antibacterial agents, sunscreens, vitamins, medicaments, fragrance materials, antioxidants, conditioners, emollients, and the like. The topically active compounds typically are insoluble in water, and the compositions deposit the topically active compounds to surfaces more effectively than present-day commercial compositions.

BACKGROUND OF THE INVENTION

For many personal care products, it is desirable not only to provide consumers the basic function of cleansing the skin or hair, but also to deposit a topically active compound that provides a predetermined benefit. The paradoxical problem of cleaning skin, or other surfaces, such as hair, cloth, or hard surfaces, while simultaneously depositing a topically active compound has been investigated for decades. Recent publications show that simultaneous cleaning and deposition of topically active ingredients is still a challenge, for example, see U.S. Pat. Nos. 5,885,948; 6,080,707; and 6,080,708.

The need for cleansing compositions that efficiently deposit topically active compounds is magnified when the typically high cost of the topically active compounds is considered, because a substantial portion of these expensive compounds is wasted in present-day compositions. In addition, particular topically active compounds, like antimicrobial agents, can provide both quick-acting and residual benefits. The value of a quick-acting antimicrobial agent is evident, and the residual benefit of antimicrobial agents is discussed in WO 98/55095 and U.S. Pat. No. 6,113,933, incorporated herein by reference.

Topically active compounds encompass a wide range of materials, including antibacterial agents, sunscreens, vitamins, medicaments, fragrance materials, antioxidants, conditioners, emollients, and other hair-care and skin-care ingredients. Many of these compounds are relatively water insoluble. Present-day compositions typically rely upon solubilization of active compounds in a surfactant system. Other systems rely upon a dispersion of emulsified active oil droplets.

A surfactant solubilized active compound is not effectively deposited unless the active compound is present at a very high level of saturation in the composition, or the active compound is chemically and/or physically modified to enhance deposition. However, there is a practical limit to incorporating a high level of saturation of active compound with traditional surfactant systems because of cost and/or regulatory constraints. For example, a composition containing 15% ammonium lauryl sulfate can require about 3% triclosan to form a saturated system. Because of the high cost of triclosan, such a composition would be too expensive to commercialize. Physical/chemical modifications of the active compounds, while possibly enhancing deposition, may not be desirable because of additional cost to an already expensive ingredient and/or the need for regulatory reapproval and additional testing required for the modified active compound.

The dispersion-type of emulsion composition typically operates by dilution deposition, and has the potential to deposit active compounds relatively well. However, this type of composition has limitations. For example, typical compositions are thickened dispersions, and cannot be used in certain dispensers (e.g., a self-foaming pump). In addition, some active compounds may not be biologically available on the skin, hair, or other surface when in the form of relatively large hydrophobic droplets or dissolved in a carrier oil.

Other strategies to enhance deposition include the addition of certain materials that enhance substantivity of active compounds by "codeposition," i.e., a "deposition aid" which adheres to the skin or hair and purportedly enhances deposition of an active ingredient. This strategy also has a limitation of decreased bioavailability when the active compound/deposition aid complex contacts the skin or hair, because the active compound may be less prone to diffuse to the site of action and/or may not be uniformly dispersed over the treated surface.

While not being bound by theory, it is envisioned that a present composition combines two principles to enhance deposition of active compounds. The first principle is the use of high thermodynamic activity (i.e., high percent saturation) to enhance the tendency of the active compound to deposit on surfaces. Allawalla et al., *J. Amer. Pharmaceut.*, Assn., XLII, pp. 267–274 (1953) disclose the importance of this factor of the activity of antimicrobial agents. In fact, as illustrated herein, thermodynamic activity is an important factor in enhancing deposition of other active compounds as well.

The second principle that contributes to enhanced deposition is the surprising and unique property of a present composition to release the active compound upon dilution. While the novel compositions containing an active compound, an anionic surfactant, a hydrotrope, a hydric solvent, an optional cosurfactant, and other optional ingredients form clear, mobile, phase-stable compositions, the compositions become unstable upon dilution with water and deposit the active compound to a surface in a highly effective manner. This type of behavior is in sharp contrast to typical solubilized active systems that generally remain stable upon dilution. The mechanism of deposition also is different from the dilution deposition of compositions disclosed in prior art because the present compositions do not contain dispersed oil droplets typical in existing emulsion systems.

Persons skilled in the art have evaluated numerous, diverse strategies to enhance the deposition of topically active compounds on the skin and hair. A review of these diverse strategies to solve the problem of cleaning a surface and depositing a topically active compound on the surface is summarized below. It can be seen that the present compositions are novel and nonobvious even over the art.

Compositions encompassed by the present invention include, but are not limited to, skin care, hair care, hard surface cleaning, and similar compositions used to cleanse and/or treat a surface. The present disclosure is directed primarily to antibacterial compositions, but also applies to other compositions containing a topically active compound.

With respect to antibacterial personal care compositions, such compositions are known in the art. Especially useful are antibacterial cleansing compositions, which typically are used to cleanse the skin and to destroy bacteria and other microorganisms present on the skin, especially the hands, arms, and face of the user.

Antibacterial compositions in general are used, for example, in the health care industry, food service industry, meat processing industry, and in the private sector by individual consumers. The widespread use of antibacterial compositions indicates the importance consumers place on controlling bacteria and other microorganism populations on skin. It is important, however, that antibacterial compositions provide a substantial and broad spectrum reduction in microorganism populations quickly and without problems associated with toxicity and skin irritation.

In particular, antibacterial cleansing compositions typically contain an active antibacterial agent, a surfactant, and various other ingredients, for example, dyes, fragrances, pH adjusters, thickeners, skin conditioners, and the like, in an aqueous carrier. Several different classes of antibacterial agents have been used in antibacterial cleansing compositions. Examples of antibacterial agents include a bisguanidine (e.g., chlorhexidine digluconate), diphenyl compounds, benzyl alcohols, trihalocarbanilides, quaternary ammonium compounds, ethoxylated phenols, and phenolic compounds, such as halo-substituted phenolic compounds, like PCMX (i.e., p-chloro-m-xylenol) and triclosan (i.e., 2,4,4'-trichloro-2'hydroxy-diphenylether). Present-day antimicrobial compositions based on such antibacterial agents exhibit a wide range of antibacterial activity, ranging from low to high, depending on the microorganism to be controlled and the particular antibacterial composition.

Most commercial antibacterial compositions, however, generally offer a low to moderate antibacterial activity. Antibacterial activity is assessed against a broad spectrum of microorganisms, including both Gram positive and Gram negative microorganisms. The log reduction, or alternatively the percent reduction, in bacterial populations provided by the antibacterial composition correlates to antibacterial activity. A log reduction of 3–5 is most preferred, a 1–3 reduction is preferred, whereas a log reduction of less than 1 is least preferred, for a particular contact time, generally ranging from 15 seconds to 5 minutes. Thus, a highly preferred antibacterial composition exhibits a 3–5 log reduction against a broad spectrum of microorganisms in a short contact time. Prior disclosures illustrate attempts to provide such antibacterial compositions, which, to date, do not provide the rapid, broad range control of microorganisms desired by consumers.

It should be noted that high log reductions have been achieved at pH values of 4 and 9, but such log reductions are attributed at least in part to these relatively extreme pH values. Compositions having such pH values can irritate the skin and other surfaces, and, therefore, typically are avoided. It has been difficult to impossible to achieve a high log reduction using an antibacterial composition having a neutral pH of about 5 to about 8, and especially about 6 to about 8.

For example, WO98/01110 discloses compositions comprising triclosan, surfactants, solvents, chelating agents, thickeners, buffering agents, and water. WO98/01110 is directed to reducing skin irritation by employing a reduced amount of surfactant.

Fendler et al. U.S. Pat. No. 5,635,462 discloses compositions comprising PCMX and selected surfactants. The compositions disclosed therein are devoid of anionic surfactants and nonionic surfactants.

WO97/46218 and WO96/06152 disclose compositions based on triclosan, organic acids or salts, hydrotropes, and hydric solvents.

EP 0 505 935 discloses compositions containing PCMX in combination with nonionic and anionic surfactants, particularly nonionic block copolymer surfactants.

WO95/32705 discloses a mild surfactant combination that can be combined with antibacterial compounds, like triclosan.

WO95/09605 discloses antibacterial compositions containing anionic surfactants and alkylpolyglycoside surfactants.

WO98/55096 discloses antimicrobial wipes having a porous sheet impregnated with an antibacterial composition containing an active antimicrobial agent, an anionic surfactant, an acid, and water, wherein the composition has a pH of about 3.0 to about 6.0.

N. A. Allawala et al., *J. Amer. Pharm. Assoc.—Sci. Ed., Vol. XLII,* no. 5, pp. 267–275 (1953) discusses the antibacterial activity of active antibacterial agents in combination with surfactants.

A. G. Mitchell, *J. Pharm. Pharmacol., Vol.* 16, pp. 533–537 (1964) discloses compositions containing PCMX and a nonionic surfactant that exhibit antibacterial activity. The compositions disclosed in the Mitchell publication exhibit antibacterial activity in at least 47 minutes contact time, thus the compositions are not highly effective.

Prior disclosures have not addressed the issue of which composition ingredient in an antibacterial composition provides bacterial control. Prior compositions also have not provided an effective, fast, and broad spectrum control of bacteria at a neutral pH of about 5 to about 8, and especially at about 6 to about 8.

An efficacious antibacterial composition has been difficult to achieve because of the properties of the antibacterial agents and the effects of a surfactant on an antibacterial agent. For example, several active antibacterial agents, like phenols, have an exceedingly low solubility in water, e.g., triclosan solubility in water is about 5 to 10 ppm (parts per million). The solubility of the antibacterial agent is increased by adding surfactants to the composition. However, an increase in solubility of the antimicrobial agent, and in turn, the amount of antibacterial agent in the composition, does not necessarily lead to an increased antibacterial efficacy.

Without being bound to any particular theory, it is theorized that the addition of a surfactant increases antimicrobial agent solubility, but also typically reduces the availability of the antibacterial agent because a surfactant in water forms micelles above the critical micelle concentration of the surfactant. The critical micelle concentration varies from surfactant to surfactant. The formation of micelles is important because micelles have a lipophilic region that attracts and solubilizes the antibacterial agent, and thereby renders the antibacterial agent unavailable to immediately contact bacteria, and thereby control bacteria in short time period (i.e., one minute or less).

The antibacterial agent solubilized in the surfactant micelles will control bacteria, but in relatively long time frames. The antibacterial agent, if free in the aqueous solution and not tied up in the surfactant micelle (i.e., is activated), is attracted to the lipophilic membrane of the bacteria and performs its function quickly. If the antibacterial agent is tied up in the surfactant micelle (i.e., is not activated), the antibacterial agent is only slowly available and cannot perform its function in a time frame that is practical for cleaning the skin.

In addition, an antibacterial agent solubilized in the micelle is readily washed from the skin during the rinsing process, and is not available to deposit on the skin to provide a residual antibacterial benefit. Rather, the antibacterial agent is washed away and wasted. The present invention is directed to enhancing the deposition of topically active compounds, like antibacterial agents.

As previously discussed, prior investigators have employed various strategies to improve deposition of a topically active compound on a surface. One strategy is to chemically modify the topically active compound, which is not a practical solution to compound deposition. Other investigators considered the nature of surface being treated. However, a commercially practicable composition should be useful on a variety of surfaces.

Other investigators utilized water-soluble cationic polymers as deposition aids for the topically active compound. See U.S. Pat. Nos. 3,489,686; 3,580,853; and 3,723,325, disclosing the use of polyethylenimine and the reaction product of polyethyleneimine and either ethylene oxide or propylene oxide, quaternary ammonium-substituted cellulose derivatives, and a polymer formed on tetraethylenepentamine and epichlorohydrin. Other patents and applications directed to the use of a deposition aid for a topically active compound include WO99/66886; U.S. Pat. Nos. 3,726,815; 3,875,071; 4,894,220; 6,057,275; and 6,126,954; WO99/63965; WO00/33807; WO99/63953.

Still other investigators directed attention to dilution deposition of a topically active compound. This is considered to be a primary deposition mechanism for many commercially available "two-in-one" conditioning shampoos. Dilution deposition involves the use of a topically active compound in a composition that is phase stable during storage and application to the hair, but becomes phase unstable and separates during rinsing. The additional water added to the composition during rinsing causes phase separation and deposition of the oil phase (which contains the topically active compound) onto the hair. Examples of patents relating to dilution deposition include EP 0 552 024; WO99/32079; WO99/53889; U.S. Pat. Nos. 5,981,465; 6,051,546; and 5,928,632; WO01/01949; WO99/26585; WO99/13854; WO99/62477; WO00/43984; and WO00/25739.

Other strategies used to enhance deposition of topically active compounds include varying the amount and type of surfactant in the composition, entrapping the topically active compound in a polymer matrix, utilizing separate cleansing and treatment compositions, using a wipe cloth to apply the topically active compound, and utilizing electrostatic sprays or liquid crystals. These strategies are disclosed in U.S. Pat. Nos. 5,409,695 and 5,814,323; WO00/64406; EP 0 573 229; WO00/00170; WO99/55303; WO99/13861; WO99/21532; WO99/12519; WO01/12138; and WO01/13871.

Accordingly, a need exists for a topically active composition that is highly efficacious in a short time period, and effectively deposits a topically active compound on a surface to provide residual benefits. The present invention is directed to such compositions, including antibacterial compositions and skin- and hair-care compositions.

SUMMARY OF THE INVENTION

The present invention relates to topically active compositions that provide (a) a rapid and substantial benefit attributed to a topically active compound, and (b) an efficacious deposition of the topically active compound on a surface to provide a residual benefit. In particular, the present invention relates to topically active compositions containing a topically active compound, wherein (a) the topically active compound is present in the continuous aqueous phase (in contrast to being present in micelles), in an amount of at least 25% of saturation, when measured at room temperature, (b) provides a substantial beneficial result, e.g., a substantial reduction in Gram positive and Gram negative bacteria, within one minute, and (c) effectively deposits the topically active compound on the treated surface to provide a residual benefit.

Therefore, one aspect of the present invention is to provide a topically active composition having an enhanced deposition of a topically active compound to a surface during a cleansing and/or rinsing step. More particularly, the present invention is directed to topically active compositions comprising a topically active compound, a primary surfactant, a hydrotrope, a hydric solvent, an optional cosurfactant, other optional ingredients, and water.

Accordingly, one aspect of the present invention is to provide a liquid topically active composition comprising:

(a) about 0.001% to about 5%, by weight, of a topically active compound;

(b) about 0.1% to about 15%, by weight, of an anionic surfactant;

(c) about 0.5% to about 35%, by weight, of a hydrotrope;

(d) about 0.5% to about 25%, by weight, of a water-soluble hydric solvent;

(e) 0% to about 5%, by weight, of a cosurfactant selected from the group consisting of a nonionic surfactant, an ampholytic surfactant, and mixtures thereof; and (f) water.

The topically active compound is a water-insoluble compound that provides a benefit to a surface contacted by the composition. The topically active compound can be, for example, an antibacterial agent, an antidandruff agent, a sunscreen, a medicament, a skin or hair conditioner, a vitamin, an emollient, an antioxidant, a fragrance, and other skin and hair care compounds.

Another aspect of the present invention is to provide a topically active composition comprising about 0.001% to about 5% of a water-insoluble topically active compound, about 5% to about 15% dipropylene glycol, about 10% to about 20% sodium xylene sulfonate, about 0.5% to about 5% ammonium lauryl sulfate, and 0% to about 5% cocamidopropylbetaine.

Yet another aspect of the present invention is to provide consumer products based on a topically active composition of the present invention, for example, a skin cleanser, a conditioning shampoo, an antidandruff shampoo, a body splash, a topical medicament, a surgical scrub, a wound care agent, a hand sanitizer gel, a disinfectant, a mouth wash, a pet shampoo, a hard surface sanitizer, and other skin and hair-care compositions.

A further aspect of the present invention is to provide a method of rapidly reducing the Gram positive and/or Gram negative bacteria populations on animal tissue, including human tissue, by contacting the tissue, like the dermis, with an antibacterial composition of the present invention for a sufficient time, such as about 15 seconds to 5 minutes, to reduce the bacteria level to a desired level, and depositing a substantial amount of the antibacterial agent on the tissue to provide a residual bacterial action.

The above and other novel aspects and advantages of the present invention are illustrated in the following, nonlimiting detailed description of the preferred embodiments.

DETAILED DESCRIPTION OF THE PREFERRED EMBODIMENTS

Personal care products incorporating a topically active compound have been used for many years. Since the introduction of such personal care products, many claims have been made that these products provide a benefit attributed to a topically active compound, like an antibacterial agent, present in the composition. With respect to antibacterial compositions, to be most effective, an antibacterial composition should provide a high log reduction against a broad spectrum of organisms in as short a contact time as possible, and also deposit on the skin to provide a residual antibacterial activity. This dual function of rapid and residual activity for antibacterial agents, and other topically active compounds, is difficult to achieve in a water-based composition that is applied to the skin, then rinsed off the skin in a relatively short time.

As presently formulated, commercial liquid antibacterial soap compositions provide a poor to marginal time kill efficacy, i.e., rate of killing bacteria. Table 1 summarizes the kill efficacy of commercial products, each of which contains about 0.2% to 0.3%, by weight, triclosan (an antibacterial agent).

TABLE 1

Time Kill Efficacy of Commercial Liquid Hand Soaps

| Product | Organism (Log Reductions after 1 Minute Contact Time) | | |
|---|---|---|---|
| | Gram Positive S. aureus | Gram negative E. coli | Gram negative K. pneum. |
| Commercial Product A | 1.39 | 0.00 | 0.04 |
| Commercial Product B | 2.20 | 0.00 | 0.01 |
| Commercial Product C | 1.85 | 0.00 | 0.00 |

Present-day products especially lack efficacy against Gram negative bacteria, such as *E. coli*, which are of particular concern to human health. In one aspect, the present invention, therefore, is directed to antibacterial compositions having an exceptionally high broad spectrum antibacterial efficacy, as measured by a rapid kill of bacteria (i.e., time kill), which is to be distinguished from persistent, or residual, kill.

In addition, as presently formulated, commercial cleansing compositions provide a poor to marginal deposition of topically active compounds. Typically, 98% or more of the applied topically active compound is wasted during application. Accordingly, there is a need to improve the deposition of such expensive active compounds in these compositions. Therefore, the present invention also is directed to providing a residual benefit attributed to the topically active compound, while incorporating a relatively low amount of the active comound in the composition.

The present antibacterial compositions provide significantly improved time kill efficacy compared to prior compositions. The basis of this improved time kill is the discovery that the antimicrobial efficacy of an active agent can be correlated to the rate at which the agent has access to an active site on the microbe. The driving force that determines the rate of agent transport to the site of action is the difference in chemical potential between the site at which the agent acts and the external aqueous phase. Alternatively stated, the microbicidal activity of an active agent is proportional to its thermodynamic activity in the external phase. Accordingly, thermodynamic activity, as opposed to concentration, is the more important variable with respect to antimicrobial efficacy. As discussed more fully hereafter, thermodynamic activity is conveniently correlated to the percent saturation of the active antibacterial agent in the continuous aqueous phase of the composition.

Many compounds have a solubility limit in aqueous solutions termed the "saturation concentration," which varies with temperature. Above the saturation concentration, the compound precipitates from solution. Percent saturation is the measured concentration in solution divided by the saturation concentration. The concentration of a compound in aqueous solution can be increased over the saturation concentration in water by the addition of compounds like surfactants. Surfactants not only increase the solubility of compounds in the continuous aqueous phase of the composition, but also form micelles, and can solubilize compounds in the micelles.

The % saturation of an active antibacterial agent in any composition, including a surfactant-containing composition, ideally can be expressed as:

$$\% \text{ saturation} = [C/C_S] \times 100\%$$

wherein C is the concentration of antibacterial agent in the composition and $C_S$ is the saturation concentration of the antibacterial agent in the composition at room temperature. While not wishing to be bound by any theory, it is contemplated that the continuous aqueous phase of a surfactant-containing composition is in equilibrium with the micellar pseudophase of said composition, and further that any dissolved species, such as an antibacterial active agent, is distributed between the aqueous continuous phase and the micellar pseudophase according to a partition law. Accordingly, the percent saturation, or alternatively the relative thermodynamic activity or relative chemical potential, of an antibacterial active agent dissolved in a surfactant-containing composition is the same everywhere within the composition. Thus, the terms percent saturation of the antibacterial agent "in a composition," "in the aqueous continuous phase of a composition," and "in the micellar pseudophase of a composition" are interchangeable, and are used as such throughout this disclosure.

Maximum antibacterial efficacy is achieved when the difference in thermodynamic activities of the active antibacterial agent between the composition and the target organism is maximized (i.e., when the composition is more "saturated" with the active ingredient). A second factor affecting antibacterial activity is the total amount of available antibacterial agent present in the composition, which can be thought of as the "critical dose." It has been found that the total amount of active agent in the continuous aqueous phase of a composition greatly influences the time in which a desired level of antibacterial efficacy is achieved, given equal thermodynamic activities. Thus, the two key factors affecting the antibacterial efficacy of an active agent in a composition are: (1) its availability, as dictated by its thermodynamic activity, i.e., percent saturation in the continuous aqueous phase of a composition, and (2) the total amount of available active agent in the solution.

An important ingredient in antibacterial cleansing compositions is a surfactant, which acts as a solubilizer, cleanser, and foaming agent. Surfactants affect the percent saturation of an antibacterial agent in solution, or more importantly, affect the percent saturation of the active agent in the continuous aqueous phase of the composition. This effect can be explained in the case of a sparingly water-soluble antibacterial agent in an aqueous surfactant solution, where the active agent is distributed between the aqueous (i.e., continuous) phase and the micellar pseudophase. For antibacterial agents of exceedingly low solubility in water, such as triclosan, the distribution is shifted strongly toward the micelles (i.e., a vast majority of the triclosan molecules are present in surfactant micelles, as opposed to the aqueous phase).

The ratio of surfactant to antibacterial agent directly determines the amount of active agent present in the surfactant micelles, which in turn affects the percent saturation of the active agent in the continuous aqueous phase. It has been found that as the surfactant:active agent ratio increases, the number of micelles relative to active molecules also increases, with the micelles being proportionally less saturated with active agent as the ratio increases. Since the active agent in the continuous phase is in equilibrium with active agent in the micellar pseudophase, as the saturation of antibacterial agent in the micellar phase decreases, so does the saturation of the antibacterial agent in the continuous phase. The converse also is true. Active agent solubilized in the micellar pseudophase is not immediately available to contact the microorganisms, and it is the percent saturation of active agent in the continuous aqueous phase that determines the antibacterial activity of the composition. The active agent present in the surfactant micelles, however, can serve as a reservoir of active agent to replenish the continuous aqueous phase as the active agent is depleted.

To summarize, the thermodynamic activity, or percent saturation, of an antibacterial agent in the continuous aqueous phase of a composition drives antibacterial activity. Further, the total amount of available active agent determines the ultimate extent of efficacy. In compositions wherein the active agent is solubilized by a surfactant, the active agent present in surfactant micelles is not directly available for antibacterial activity. For such compositions, the percent saturation of the active agent in the composition, or alternatively the percent saturation of the active agent in the continuous aqueous phase of the composition, determines antibacterial efficacy.

The present compositions are topically active compositions having an improved effectiveness with respect to imparting a rapid benefit and a residual benefit. As illustrated in the following embodiments, a topically active composition of the present invention comprises: (a) about 0.001% to about 5%, by weight, of a topically active compound; (b) about 0.1% to about 15%, by weight, of an anionic surfactant; (c) about 0.5% to about 35%, by weight, of a hydrotrope; (d) about 0.5% to about 25%, by weight, of a water-soluble hydric solvent; (e) 0% to about 5%, by weight, of a cosurfactant selected from the group consisting of a nonionic surfactant, an ampholytic surfactant, and mixtures thereof; and (f) water. The compositions have a percent saturation of topically active compound in the continuous aqueous phase of at least about 25%, when measured at room temperature. Antibacterial compositions of the present invention exhibit a log reduction against Gram positive bacteria of at least about 2 after 30 seconds contact. The compositions exhibit a log reduction against Gram negative bacteria of at least about 2.5 after 30 seconds contact.

In addition to providing a rapid and efficient benefit, a residual topical efficacy also is desired. To achieve a residual activity, the topically active compound must be deposited on the skin in the short time span between application of the composition to the skin and rinsing from the skin. It also is important that a variety of topically active compounds, such as medicaments, antibacterial agents, conditioners, fragrances, and the like, are effectively deposited on the skin prior to rinsing of the composition from the skin.

The present invention, therefore, is directed to topically active compositions that effectively and rapidly deposit the topically active compound on a cleansed surface. The following Table summarizes results of deposition tests comparing commercial products to examples of the present compositions. The compositions contain triclosan (TCS) as the water-insoluble topically active compound. As seen from these test results, the present compositions have superior efficacy over commercial products in the deposition of the topically active compound.

| Efficacy of Deposition of Triclosan (TCS) from Liquid Hand Soaps | | |
|---|---|---|
| Sample | % TCS | % TCS Remaining on Skin vs. Applied Dose[1] |
| Test I | | |
| Commercial Product C (LD) | 0.2 | 7.39 |
| Example 15D | 0.2 | 26.95 |
| Sample | % TCS | Relative Deposition[1] (compared to Commercial Product C) |
| Test II | | |
| Commercial Product A (PC) | 1 | 5.80 |
| Commercial Product B (SX) | 1 | 4.11 |
| Commercial Product C (LD) | 0.2 | 1.00 |
| Example 14A | 1 | 10.49 |
| Example 15C | 0.3 | 11.37 |

[1]As determined by a pigskin deposition test described below.

The following illustrates important, nonlimiting embodiments of the present invention. In particular, compositions of the present invention comprise a topically active compound, a primary surfactant, a hydrotrope, a hydric solvent, an optional cosurfactant, and water. The compositions can further include additional optional ingredients disclosed hereafter, like pH adjusters, dyes, and preservatives.

The following is a nonlimiting description of ingredients that can be included in a present composition.

1. Topically Active Compound

A topically active compound is present in a composition of the present invention in an amount of about 0.001% to about 5%, and preferably about 0.01% to about 3%, by weight of the composition. To achieve the full advantage of the present invention, the topically active compound is present in an amount of about 0.05% to about 2%, by weight, of the composition.

The topically active compositions can be ready to use compositions, which typically contain 0.001% to about 2%, preferably 0.01% to about 1.5%, and most preferably about 0.05% to about 1%, of a topically active compound, by weight of the composition. The topically active compositions also can be formulated as concentrates that are diluted before use with one to about 100 parts water to provide an end use composition. The concentrated compositions typically contain greater than about 0.1% and up to about 5%, by weight, of the topically active compound. Applications also are envisioned wherein the end use composition contains greater than 2%, by weight, of the topically active compound.

As discussed above, the absolute amount of topically active compound present in the composition is not as important as the amount of available topically active compound in the composition, and the ability of the composition to rapidly and effectively deposit the topically active compound on a treated surface. The amount of available topically active compound in the composition, and the ability of the composition to deposit the topically active compound, is related to the identity of the surfactant in the composition, the amount of surfactant in the composition, and the presence of optional ingredients in the composition.

For antibacterial agents, to achieve the desired bacteria kill in a short contact time, like 15 to 60 seconds, the continuous aqueous phase of the composition contains an amount of antibacterial agent that is at least about 50%, and preferably at least about 75%, of the saturation concentration of the antibacterial agent in water, when measured at room temperature. To achieve the full advantage of the present invention, the continuous aqueous phase is about 95% to 100% saturated with the antibacterial agent. The amount of antibacterial agent present in the continuous aqueous phase can be defined as the total amount of antibacterial agent in the composition, less any antibacterial agent present in surfactant micelles. The method of determining percent saturation of antibacterial agent in the composition is disclosed hereafter.

To achieve the desired residual activity, the topically active compound is rapidly and effectively deposited on the surface contacted by a composition of the present invention.

Topically active compounds of the present invention include, but are not limited to, antibacterial agents, skin and hair conditioning agents, fragrances, antidandruff agents, vitamins, sunscreen agents, antioxidants, antiacne agents, external analgesics, skin protectants, antiinflammatory agents, topical anesthetics, ultraviolet light absorbers, and other cosmetic and medicinal topically active compounds.

The topically active compound is a water-insoluble compound. As used herein, the term "water-insoluble" is defined as a compound having a water solubility, at 25° C. and 1 atmosphere pressure, of 2 grams or less per 100 ml of water, with water solubilities being as low as about 1 ppm (part per million).

One embodiment of topically active compounds useful in the present invention are water-insoluble phenolic compounds having as antimicrobial properties, and exemplified by the following classes of compounds:

2-Hydroxydiphenyl Compounds

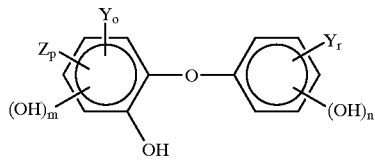

wherein Y is chlorine or bromine, Z is $SO_2H$, $NO_2$, or $C_{1-4}$alkyl, r is 0 to 3, o is 0 to 3, p is 0 or 1, m is 0 or 1, and n is 0 or 1.

In preferred embodiments, Y is chlorine or bromine, m is 0, n is 0 or 1, o is 1 or 2, r is 1 or 2, and p is 0.

In especially preferred embodiments, Y is chlorine, m is 0, n is 0, o is 1, r is 2, and p is 0.

A particularly useful 2-hydroxydiphenyl compound has the structure:

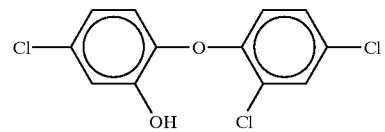

having the adopted name, triclosan, and available commercially under the tradename IRGASAN DP300, from Ciba Specialty Chemicals Corp., Greensboro, N.C. Another useful 2-hydroxydiphenyl compound is 2,2'-dihydroxy-5,5'-dibromo-diphenyl ether.

Phenol Derivatives

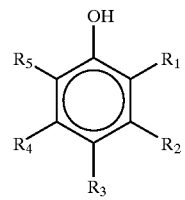

wherein $R_1$ is hydro, hydroxy, $C_{1-4}$alkyl, chloro, nitro, phenyl, or benzyl; $R_2$ is hydro, hydroxy, $C_{1-6}$alkyl, or halo; $R_3$ is hydro, $C_{1-6}$alkyl, hydroxy, chloro, nitro, or a sulfur in the form of an alkali metal salt or ammonium salt; $R_4$ is hydro or methyl, and $R_5$ is hydro or nitro. Halo is bromo or, preferably, chloro.

Specific examples of phenol derivatives include, but are not limited to, chlorophenols (o-, m-, p-), 2,4-dichlorophenol, p-nitrophenol, picric acid, xylenol, p-chloro-m-xylenol, cresols (o-, m-, p-), p-chloro-m-cresol, pyrocatechol, resorcinol, 4-n-hexylresorcinol, pyrogallol, phloroglucin, carvacrol, thymol, p-chlorothymol, o-phenylphenol, o-benzylphenol, p-chloro-o-benzylphenol, phenol, 4-ethylphenol, and 4-phenolsulfonic acid. Other phenol derivatives are listed in WO 98/55096, incorporated herein by reference.

Diphenyl Compounds

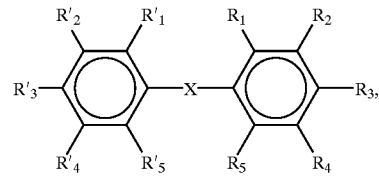

wherein X is sulfur or a methylene group, $R_1$ and $R'_1$ are hydroxy, and $R_2$, $R'_2$, $R_3$, $R'_3$, $R_4$, $R'_4$ $R_5$, and $R'_5$, independent of one another, are hydro or halo. Specific, nonlimiting examples of diphenyl compounds are hexachlorophene, tetrachlorophene, dichlorophene, 2,3-dihydroxy-5,5'-dichlorodiphenyl sulfide, 2,2'-dihydroxy-3,3',5,5'-tetrachlorodiphenyl sulfide, 2,2'-dihydroxy-3,5',5,5',6,6'-hexachlorodiphenyl sulfide, and 3,3'-dibromo-5,5'-dichloro-2,2'-dihydroxydiphenylamine. Other diphenyl compounds are listed in WO 98/55096, incorporated herein by reference.

Similarly, topically active medicaments, like antifungal compounds; antibacterial compounds; antiinflammatory compounds; topical anesthetics; skin rash, skin disease, and dermatitis medications; and antiitch and irritation-reducing compounds can be included in a composition of the present invention. For example, analgesics, such as benzocaine, dyclonine, aloe vera, and the like; anesthetics, such as butamben picrate, lidocaine, xylocaine, and the like; antibacterials and antiseptics, such as polymyxin b sulfate-bacitracin, zinc-neomycin sulfate-hydrocortisone, chloramphenicol, erythromycin, and the like; antiparasitics, such as lindane; antiinflammatory agents, such as alclometasone dipropionate, betamethasone valerate, and the like; burn relief ointments, such as o-amino-p-toluenesulfonamide monoacetate and the like; depigmenting agents, such as monobenzone; dermatitis relief agents, such as the active steroid amcinonide, diflorasone, hydrocortisone, and the like; fungicides, such as butocouazole, haloprogin, clotrimazole, and the like; psoriasis, seborrhea, and scabicide agents, such as anthralin, methoxsalen, coal tar, pyrithione zinc, salicyclic acid, sulfur, and the like; steroids, such as 2-(acetyloxy)-9-fluoro-1',2', 3',4'-tetrahydro-11-hydroxypregna-1,4-dieno-[16,17-b] naphthalene-3, 20-dione and 21-chloro-9-fluoro-1',2',3',4'-tetrahydro-11b-hydroxypregna-1,4-dieno[16z,17-b] naphthalene-3,20-dione. Any other medication capable of topical administration also can be incorporated in a composition of the present invention in an amount sufficient to perform its intended function. Other topically active compounds are listed in *Remington's Pharmaceutical Sciences*, 17th Ed., Merck Publishing Co., Easton Pa. (1985), pp. 773–791 and pp. 1054–1058 (hereinafter *Remington's*), incorporated herein by reference.

The topically active compound also can be an antiacne agent such as benzoyl peroxide, erythromycinbenzoyl peroxide, clindamycin, 5,7-dichloro-8-hydroxyquinoline, salicylic acid, sulfur, and the like.

In addition, the topically active compound can be a sunscreen, such as benzophenone-3, benzophenone-4, trihydroxycinnamic acid, tannic acid, uric acid, quinine, dihydroxy naphtholic acid, an anthranilate, methoxycinnamate, p-aminobenzoic acid, phenylbenzimidazole sulfonic acid, dioxybenzone, ethyl 4-[bis(hydroxypropyl)] aminobenzoate, glyceryl aminobenzoate, homosalate, menthyl anthranilate, octocrylene, octyl methoxycinnamate, octyl salicylate, oxybenzone, padimate O, red petrolatum, 4-menthylbenzylidene camphor, benzophenone-1, benzophenone-2, benzophenone-6, benzophenone-12, isopropyl dibenzoyl methane, butyl methoxydibenzoylmethane, zotocrylene, cinoxate, digalloyl trioleate, benzophenone-8, glyceryl PABA, ethyl dihydroxypropyl PABA, benzophenone-4, and the like. Other sunscreen compounds are listed in *CTFA Handbook*, pages 86 and 87, incorporated herein by reference.

Additional classes of topically active compounds include external analgesics, such as benzyl alcohol, camphor, juniper tar, menthol, methyl salicylate, phenol, and resorcinol;
  fragrances, such as the compounds disclosed in Appendix A;
  hair conditioning agents, such as the compounds disclosed in Appendix B;
  humectants, such as hydroquinone, mercaptopropionic acid, thioglycolic acid, and thiosalicylic acid;
  skin protectants, such as allantoin, calamine, cocoa butter, dimethicone, petrolatum, and shark liver oil;
  ultraviolet light absorbers, such as the compounds discloser in Appendix C; and
  skin care agents, such as the compounds disclosed in Appendix D. The identity of the skin care agent is not particularly limited, as long as the agent does not adversely affect the stability or efficacy of the composition. One important class of skin care agents is emollients. Emollients are cosmetic ingredients that help to maintain a soft, smooth, and pliable skin appearance. Emollients function by remaining on the skin surface or in the stratum corneum to act as lubricants, to reduce flaking, and to improve skin appearance.

In general, the skin care agent includes polymers, protein derivatives (e.g., derivatized hydrolyzed wheat protein), ethoxylated fatty ethers, and similar skin care agents. For example, suitable skin care agents include, but are not limited to, esters comprising an aliphatic alcohol having 2 to about 18 carbon atoms condensed with an aliphatic or aromatic carboxylic acid including 8 to about 20 carbon atoms, e.g., isopropyl myristate, decyl oleate, and cetearyl isononanate. The ester is either straight chained or branched. Preferably, the ester has a molecular weight of less than about 500 and provides emollient properties.

Nonlimiting examples of other skin care agents include, but are not limited to, a methyl ether of a polyethylene glycol, stearyl methicone, dimethicone copolyol, sorbitan oleate, steareth-2, PEG-7 glyceryl cocoate, a $C_{12}$–$C_{20}$ alcohol, canola oil, glyceryl laurate, triglyceryl monostearate, glyceryl monostearate, PPG-2 hydroxyethyl cocamide, mineral oil, petrolatum, and aloe barbadensis. The above skin care agents can be used alone or in admixture.

2. Anionic Surfactant

In addition to the topically active compound, a present composition also contains an anionic surfactant as the primary surfactant. The anionic surfactant is present in an amount of about 0.1% to about 15%, and preferably about 0.3% to about 8%, by weight, of the composition. To achieve the full advantage of the present invention, the composition contains about 0.5% to about 5%, by weight, of the anionic surfactant.

Ready-to-use compositions typically contain about 0.1% to about 2%, preferably about 0.3% to about 1.5%., and most preferably about 0.5% to about 1%, of an anionic surfactant, by weight of the composition. Concentrated compositions suitable for dilution typically contain greater than about 2%, by weight, of an anionic surfactant.

The amount of anionic surfactant present in the composition is related to the amount and identity of the topically active compound in the composition and to the identity of the surfactant. The amount of surfactant is determined such that the percent saturation of the topically active compound is at least about 25%, preferably at least about 50%, and most preferably at least about 75%.

The topically active compositions can contain any anionic surfactant having a hydrophobic moiety, such as a carbon chain including about 8 to about 30 carbon atoms, and particularly about 12 to about 20 carbon atoms, and further having a hydrophilic moiety, such as sulfate, sulfonate, carbonate, phosphate, or carboxylate. Often, the hydrophobic carbon chain is etherified, such as with ethylene oxide or propylene oxide, to impart a particular physical property, such as increased water solubility or reduced surface tension to the anionic surfactant.

Therefore, suitable anionic surfactants include, but are not limited to, compounds in the classes known as alkyl sulfates, alkyl ether sulfates, alkyl ether sulfonates, sulfate esters of an alkylphenoxy polyoxyethylene ethanol, alpha-olefin sulfonates, beta-alkoxy alkane sulfonates, alkylaryl sulfonates, alkyl monoglyceride sulfates, alkyl monoglyceride sulfonates, alkyl carbonates, alkyl ether carboxylates, fatty acids, sulfosuccinates, sarcosinates, octoxynol or nonoxynol phosphates, taurates, fatty taurides, fatty acid amide polyoxyethylene sulfates, isethionates, or mixtures thereof. Additional anionic surfactants are listed in McCutcheon's Emulsifiers and Detergents, 1993 Annuals, (hereafter McCutcheon's), McCutcheon Division, MC Publishing Co., Glen Rock; N.J., pp. 263–266, incorporated herein by reference. Numerous other anionic surfactants, and classes of anionic surfactants, are disclosed in Laughlin et al. U.S. Pat. No. 3,929,678, incorporated herein by reference.

Examples of anionic surfactants include a $C_8$–$C_{18}$ alkyl sulfate, a $C_8$–$C_{18}$ fatty acid salt, a $C_8$–$C_{18}$ alkyl ether sulfate having one or two moles of ethoxylation, a $C_8$–$C_{18}$ alkamine oxide, a $C_8$–$C_{18}$ alkyl sarcosinate, a $C_8$–$C_{18}$ sulfoacetate, a $C_8$–$C_{18}$ sulfo succinate, a $C_8$–$C_{18}$ alkyl diphenyl oxide disulfonate, a $C_8$–$C_{18}$ alkyl carboxylate, a $C_8$–$C_{18}$ alpha-olefin sulfonate, a methyl ester sulfonate, and mixtures thereof. The $C_8$–$C_{18}$ alkyl group contains eight to eighteen carbon atoms, and can be straight chain (e.g., lauryl) or branched (e.g., 2-ethylhexyl). The cation of the anionic surfactant can be an alkali metal (preferably sodium or potassium), ammonium, $C_1$–$C_4$ alkylammonium (mono-, di-, tri), or $C_1$–$C_3$ alkanolammonium (mono-, di-, tri-). Lithium and alkaline earth cations (e.g., magnesium) can be used, but antibacterial efficacy is reduced.

Specific surfactants include, but are not limited to, lauryl sulfates, octyl sulfates, 2-ethylhexyl sulfates, lauramine oxide, decyl sulfates, tridecyl sulfates, cocoates, lauroyl sarcosinates, lauryl sulfosuccinates, linear $C_{10}$ diphenyl oxide disulfonates, lauryl sulfosuccinates, lauryl ether sulfates (1 and 2 moles ethylene oxide), myristyl sulfates, oleates, stearates, tallates, cocamine oxide, decylamine oxide, myristamine oxide, ricinoleates, cetyl sulfates, and similar anionic surfactants.

3. Hydric Solvent and Hydrotrope

The present invention also contains about 0.5% to about 25%, by weight, of a hydric solvent, and 0.5% to about 35%, by weight, of a hydrotrope.

Preferred embodiments contain about 2% to about 20%, by weight, of a hydric solvent and about 3% to about 30%, by weight, of a hydrotrope. Most preferred embodiments contain about 5% to about 15%, by weight, of a hydric solvent and about 5% to about 25%, by weight, of a hydrotrope.

As defined herein, the term "hydric solvent" is a water-soluble organic compound containing one to six, and typically one to three, hydroxyl groups. The term "hydric solvent," therefore, encompasses water-soluble alcohols and diols. Specific examples of hydric solvents include, but are not limited to, methanol, ethanol, isopropyl alcohol, n-butanol, n-propyl alcohol, ethylene glycol, propylene glycol, diethylene glycol, dipropylene glycol, tripropylene glycol, hexylene glycol, butylene glycol, PEG 4, and similar hydroxyl-containing compounds.

A hydrotrope is a compound that has the ability to enhance the water solubility of other compounds. A hydrotrope utilized in the present invention lacks surfactant properties, and typically is a short-chain alkyl aryl sulfonate. Specific examples of hydrotropes includes, but are not limited to, sodium cumene sulfonate, ammonium cumene sulfonate, ammonium xylene sulfonate, potassium toluene sulfonate, sodium toluene sulfonate, sodium xylene sulfonate, toluene sulfonic acid, and xylene sulfonic acid. Other useful hydrotropes include sodium polynaphthalene sulfonate, sodium polystyrene sulfonate, sodium methyl naphthalene sulfonate, and disodium succinate.

4. Carrier

The carrier of the composition comprises water.

5. Optional Ingredients

A topically active composition of the present invention also can contain optional ingredients well known to persons skilled in the art. For example, the composition can contain an optional nonionic or ampholytic surfactant as a cosurfactant.

The compositions also can contain other optional ingredients, such as dyes and preservatives, that are present in a sufficient amount to perform their intended function and do not adversely affect the efficacy of the composition. Such optional ingredients typically are present, individually, from 0% to about 5%, by weight, of the composition, and, collectively, from 0% to about 20%, by weight, of the composition.

Classes of optional ingredients include, but are not limited to, a nonionic and/or ampholytic cosurfactant, dyes, pH adjusters, thickeners, viscosity modifiers, buffering agents, foam stabilizers, antioxidants, foam enhancers, chelating agents, opacifiers, and similar classes of optional ingredients known to persons skilled in the art.

Specific classes of optional ingredients include alkanolamides as foam boosters and stabilizers; gums and polymers as thickening agents; inorganic phosphates, sulfates, and carbonates as buffering agents; EDTA and phosphates as chelating agents; and acids and bases as pH adjusters.

Examples of preferred classes of basic pH adjusters are ammonia; mono-, di-, and tri-alkyl amines; mono-, di-, and tri-alkanolamines; alkali metal and alkaline earth metal hydroxides; and mixtures thereof. However, the identity of the basic pH adjuster is not limited, and any basic pH adjuster known in the art can be used. Specific, nonlimiting examples of basic pH adjusters are ammonia; sodium, potassium, and lithium hydroxide; monoethanolamine; triethylamine; isopropanolamine; diethanolamine; and triethanolamine.

Examples of preferred classes of acidic pH adjusters are the mineral acids and polycarboxylic acids. Nonlimiting examples of mineral acids are hydrochloric acid, nitric acid, phosphoric acid, and sulfuric acid. Nonlimiting examples of polycarboxylic acids are citric acid, glycolic acid, and lactic acid. The identity of the acidic pH adjuster is not limited and any acidic pH adjuster known in the art, alone or in combination, can be used.

An alkanolamide to provide composition thickening, foam enhancement, and foam stability can be, but is not limited to, cocamide MEA, cocamide DEA, soyamide DEA, lauramide DEA, oleamide MIPA, stearamide MEA, myristamide MEA, lauramide MEA, capramide DEA, ricinoleamide DEA, myristamide DEA, stearamide DEA, oleylamide DEA, tallowamide DEA, lauramide MIPA, tallowamide MEA, isostearamide DEA, isostearamide MEA, and mixtures thereof.

The topically active compositions can contain an optional nonionic cosurfactant. Typically, a nonionic surfactant has a hydrophobic base, such as a long chain alkyl group or an alkylated aryl group, and a hydrophilic chain comprising a sufficient number (i.e., 1 to about 30) of ethoxy and/or propoxy moieties. Examples of classes of nonionic surfactants include ethoxylated alkylphenols, ethoxylated and propoxylated fatty alcohols, polyethylene glycol ethers of methyl glucose, polyethylene glycol ethers of sorbitol, ethylene oxidepropylene oxide block copolymers, ethoxylated esters of fatty ($C_8$–$C_{18}$) acids, condensation products of ethylene oxide with long chain amines or amides, and mixtures thereof.

Exemplary nonionic surfactants include, but are not limited to, methyl gluceth-10, PEG-20 methyl glucose distearate, PEG-20 methyl glucose sesquistearate, $C_{11-15}$ pareth-20, ceteth-8, ceteth-12, dodoxynol-12, laureth-15, PEG-20 castor oil, polysorbate 20, steareth-20, polyoxyethylene-10 cetyl ether, polyoxyethylene-10 stearyl ether, polyoxyethylene-20 cetyl ether, polyoxyethylene-10 oleyl ether, polyoxyethylene-20 oleyl ether, an ethoxylated nonylphenol, ethoxylated octylphenol, ethoxylated dodecylphenol, or ethoxylated fatty ($C_6$–$C_{22}$) alcohol, including 3 to 20 ethylene oxide moieties, polyoxyethyiene-20 isohexadecyl ether, polyoxyethylene-23 glycerol laurate, polyoxyethylene-20 glyceryl stearate, PPG-10 methyl glucose ether, PPG-20 methyl glucose ether, polyoxyethylene-20 sorbitan monoesters, polyoxyethylene 80 castor oil, polyoxyethylene-15 tridecyl ether, polyoxyethylene-6 tridecyl ether, laureth-2, laureth-3, laureth-4, PEG-3 castor oil, PEG 600 dioleate, PEG 400 dioleate, and mixtures thereof.

Numerous other nonionic surfactants are disclosed in McCutcheon's Detergents and Emulsifiers, 1993 Annuals, published by McCutcheon Division, MC Publishing Co., Glen Rock, N.J., pp. 1–246 and 266–272; in the *CTFA International Cosmetic Ingredient Dictionary, Fourth Ed.*, Cosmetic, Toiletry and Fragrance Association, Washington, D.C. (1991) (hereinafter the CTFA Dictionary) at pages 1–651; and in the *CTFA Handbook*, at pages 86–94, each incorporated herein by reference.

In addition to an optional nonionic cosurfactant, ampholytic and amphoteric surfactants can be used in the topically active compositions as the optional cosurfactant.

Ampholytic surfactants can be broadly described as derivatives of secondary and tertiary amines having aliphatic radicals that are straight chain or branched, and wherein one of the aliphatic substituents contains from about 8 to 18 carbon atoms and at least one of the aliphatic substituents contains an anionic water-solubilizing group, e.g., carboxy, sulfonate, or sulfate. Examples of compounds falling within this description are sodium 3-(dodecylamino)propionate, sodium 3-(dodecylamino)propane-1-sulfonate, sodium 2-(dodecylamino)ethyl sulfate, sodium 2-(dimethylamino) octadecanoate, disodium 3-(N carboxymethyldodecylamino)propane-1-sulfonate, disodium octadecyliminodiacetate, sodium 1-carboxymethyl-2-undecylimidazole, and sodium N,N-bis(2-hydroxyethyl)-2-sulfato-3-dodecoxypropylamine.

More particularly, one class of ampholytic surfactants include sarcosinates and taurates having the general structural formula

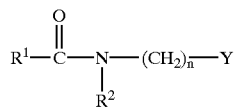

wherein $R^1$ is $C_{11}$ through $C_{21}$ alkyl, $R^2$ is hydrogen or $C_1$–$C_2$ alkyl, Y is $CO_2M$ or $SO_3M$, M is an alkali metal, and n is a number 1 through 3.

Another class of ampholytic surfactants is the amide sulfosuccinates having the structural formula

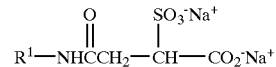

The following classes of ampholytic surfactants also can be used:

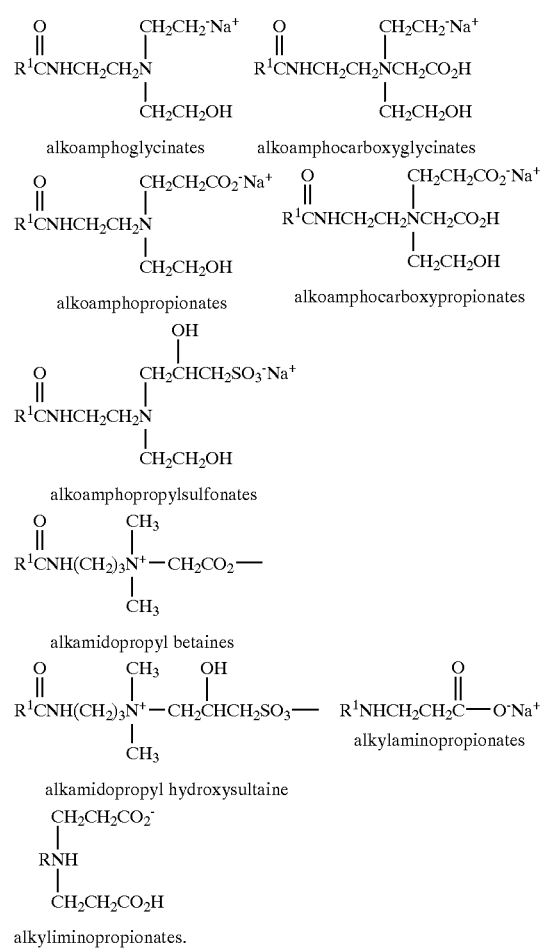

Additional classes of ampholytic surfactants include the phosphobetaines and the phosphitaines.

Specific, nonlimiting examples of ampholytic surfactants useful in the present invention are sodium coconut N-methyl taurate, sodium oleyl N-methyl taurate, sodium tall oil acid N-methyl taurate, sodium palmitoyl N-methyl taurate, cocodimethylcarboxymethylbetaine, lauryldimethylcarboxymethylbetaine, lauryldimethylcarboxyethylbetaine, cetyldimethylcarboxymethylbetaine, lauryl-bis-(2-hydroxyethyl)-carboxymethylbetaine, oleyldimethylgammacarboxypropylbetaine, lauryl-bis-(2-hydroxypropyl)-carboxyethylbetaine, cocoamidodimethylpropylsultaine, stearylamidodimethylpropylsultaine, laurylamido-bis-(2-hydroxyethyl)-propylsultaine, disodium oleamide PEG-2 sulfosuccinate, TEA oleamido PEG-2 sulfosuccinate, disodium oleamide MEA sulfosuccinate, disodium oleamide MIPA sulfosuccinate, disodium ricinoleamide MEA sulfosuccinate, disodium undecylenamide MEA sulfosuccinate, disodium wheat germamido MEA sulfosuccinate, disodium wheat germamido PEG-2 sulfosuccinate, disodium isostearamideo MEA sulfosuccinate, cocoamphoglycinate, cocoamphocarboxyglycinate, lauroamphoglycinate, lauroamphocarboxyglycinate, capryloamphocarboxyglycinate, cocoamphopropionate, cocoamphocarboxypropionate, lauroamphocarboxypropionate, capryloamphocarboxypropionate, dihydroxyethyl tallow glycinate, cocamido disodium 3-hydroxypropyl phosphobetaine, lauric myristic amido disodium 3-hydroxypropyl phosphobetaine, lauric myristic amido glyceryl phosphobetaine, lauric myristic amido carboxy disodium 3-hydroxypropyl phosphobetaine, cocoamido propyl monosodium phosphitaine, lauric myristic amido propyl monosodium phosphitaine, and mixtures thereof.

In addition, the topically active compositions of the present invention do not rely upon a low pH or a high pH to provide a rapid reduction in bacterial populations. The topically active compositions of the present invention can have a pH of about 4 to about 9, but at the two extremes of this pH range, the compositions can be irritating to the skin or damaging to other surfaces contacted by the composition. Accordingly, topically active compositions of the present invention preferably have a pH of about 5 to about 8, and more preferably about 6 to about 8. To achieve the full advantage of the present invention, the topically active compositions have a pH of about 6.5 to about 7.5.

To demonstrate the new and unexpected results provided by the topically active compositions of the present invention, the following Examples and Comparative Examples were prepared, and the ability of the compositions to control Gram positive and Gram negative bacteria, and to deposit a topically active compound on a surface, were determined. The weight percentage listed in each of the following examples represents the actual, or active, weight amount of each ingredient present in the composition. The compositions were prepared by blending the ingredients, as understood by those skilled in the art and as described below.

The following materials were used as ingredients in the examples. The source of each ingredient, and its abbreviation, are summarized below:

a) Alkyl (linear) diphenyl oxide disulfonate, Pilot Chemical Co., Santa Fe Springs, Calif., CALFAX 10L-45 (active=45.4%), b) Alkyl polyglucoside (APG), Henkel Corp., Hoboken, N.J., PLANTAREN 2000N UP (active=55.53%), c) Alpha-olefin sulfonate (AOS), Stepan Chemical Co., Northfield, Ill., BIOTERGE AS-40 (active=38.80%), d) Ammonium lauryl sulfate (ALS), Henkel Corp., STANDAPOL A (active level=28.3%), e) Ammonium xylene sulfonate (AXS), Stepan Corp., STEPANATE AXS (active=40%), f) Cocamidopropyl betaine (CAPB), McIntyre Group, Ltd., Chicago, Ill., MACKAM 35-HP (est. 30% active betaine), g) Dipropylene glycol (DPG), Dow Chemical Co., Midland, Mich., h) Disodium laureth sulfosuccinate (DSLScct), McIntyre Group, Ltd., MACKANATE EL (active=33.8%), i) Disodium lauryl sulfosuccinate (DSLrylScct), McIntyre Group, Ltd., MACKANATE LO (active est.=40%), j) DMDM Hydantoin (DMDM), MacIntyre Group, Ltd., MACKSTAT DM (approx. 55% active), k) DowFax Hydrotrope Solution (DFX), Dow Chemical Co., DowFax Hydrotrope Solution (Benzene, 1,1' oxybis-, sec-hexyl derivatives, sulfonated sodium salt) (active=45.7%), l) Glycerin (GLY), Henkel/Emery, Cincinnati, Ohio, Emery 916 Glycerine (99.7% CP/USP), m) Isopropanol (IPA), Fisher Scientific, Pittsburgh, Pa., 2-Propanol, HPLC Grade A 451–4, n) Lauramine oxide (LAO), McIntyre Group, Ltd., MACKAMINE LO (active=30.55%), o) Liquid Perfume (PF), p) Lithium lauryl sulfate (LLS), Henkel, TEXAPON LLS (active=28.8%), q) Magnesium lauryl sulfate (MLS), Stepan Chemical Co., STEPANOL MG (active=28.3%), r) Methyl ester sulfonate (MES), Stepan Chemical Co., ALPHA-STEP ML-40 (Sodium methyl-2 sulfo laurate and disodium 2-sulfo lauric acid) (active=36.47%), s) Monoethanolamine (MEA), Dow Chemical Co., t) Monoethanolamine lauryl sulfate (MEALS), Albright & Wilson, Cumbria, England, EMPICOL, LQ 33/F (active=33%), u) Octylphenol ethoxylate, 9–10 moles EO (TX100), Union Carbide, TRITON-X 100, v) PEG 6ME, polyethylene glycol 300 methyl ether, available from Dow Chemical Co., Midland, Mich., as MPEG 350 (active=est. 100%), w) Poloxymer 338 (F108), BASF, Wyandotte, Mich., PLURONIC F108 (active=est. 100%), x) Potassium cocoate (KCO), McIntyre Group, Ltd., MACKADET 40-K (active=38.4%), y) Potassium laurate (KL), prepared from lauric acid (Sigma, #L-4250, active=99.8%) and potassium hydroxide, z) Potassium oleate (KO), Norman, Fox & Co., Vernon, Calif., NORFOX KO (active=approx. 80%), aa) Propylene glycol (PG), Dow Chemical Co., USP Grade (active level=99.96%), bb) Sodium 2-ethylhexyl sulfate (S2EHS), Henkel, SULFOTEX OA (active=39.68%), cc) Sodium $C_{12}$–$C_{18}$ sulfate (SC12-18S) Henkel, TEXAPON ZHC needles (active=90.95%), dd) Sodium cocoamphoacetate (SCA), McIntyre Group, Ltd., MACKAM IC-90 (active=approx. 32%), ee) Sodium cumene sulfonate (SCS), Stepan Chemical Co., STEPANATE SCS (active=44.6%), ff) Sodium decyl sulfate (SDecS), Henkel, SULFOTEX 110 (active=30.80%), gg) Sodium lauroyl sarcosinate (SLSarc), Hampshire Chemical Co., Lexington, Mass., HAMPOSYL L-30 Type 724 (active=29.9%), hh) Sodium lauryl ether sulfate, 1 mole EO (SLES-1), Henkel, STANDAPOL ES-1 (active=25.40%), ii) Sodium lauryl ether sulfate, 2 mole EO (SLES-2), Henkel, STANDAPOL ES-2 (active level=25.71%), jj) Sodium lauryl sulfate/sodium dodecyl sulfate (SLS/SDS), BDH Biochemical, BDH Ltd., Poole, England, (active=99.0%), kk) Sodium lauryl sulfoacetate (SLSA), Stepan Chemical Co., LANTHIANOL LAL (active=72.65%), ll) Sodium octyl sulfate (SOS), Henkel, STANDAPOL LF (active=32.90%), mm) Sodium salt of NEODOX 23-4 (NDX23-4), Shell Chemical Co., derived from NEODOX 23-4, a compound having a 194 molecular weight chain, 4 moles of EO and a carboxylate group (active=94.2%), nn) Sodium tridecyl sulfate (SC13S), Rhodia, Parsippany, N.J., RHODAPON TDS (active=24.65%), oo) Sodium xylene sulfonate (SXS), Stepan Chemical Co, STEPANATE SXS (active level=40–42%), pp) Triclosan (TCS), IRGASAN DP 300, Ciba Specialty Chemicals Corp., Greensboro, N.C. (GC assay on lots used=99.8–99.9% active TCS; mp=56.0–58.0 C.), qq) Triethanolamine lauryl sulfate (TEALS), Henkel, STANDAPOL T (active=40.1%), rr) Tripropylene Glycol (TPG), Dow Chemical Co., Tripropylene Glycol, ss) Water—Unless otherwise indicated, the water was laboratory deionized (DI) water, tt) Lauramide TEA (LDEA), McIntyre Group, Ltd., MACKERNIUM L 10 (active=100%), uu) 2-Hydroxy-4-methoxybenzophenone (Bph-3), BASF Corp., Olive, N.J., UVINUL M40 (active=100%), vv) dl-α Tocopheryl acetate (VitE-OAc), Roche Vitamins, Inc., Parsippany, N.J., (actives=100%); and ww) α-Hexylcinnamaldehyde (AHCALD), Aldrich Chemical Co., Milwaukee, Wis. (actives=100%).

The following methods were used in the preparation and testing of the examples:

a) Determination of Rapid Germicidal (Time Kill) Activity of Antibacterial Products. The activity of antibacterial compositions was measured by the time kill method, whereby the survival of challenged organisms exposed to an antibacterial test composition is determined a's a function of time. In this test, a diluted aliquot of the composition is brought into contact with a known population of test bacteria for a specified time period at a specified temperature. The test composition is neutralized at the end of the time period, which arrests the antibacterial activity of the composition. The percent or, alternatively, log reduction from the original bacteria population is calculated. In general, the time kill method is known to those skilled in the art.

The composition can be tested at any concentration from 0–100%. The choice of which concentration to use is at the discretion of the investigator, and suitable concentrations are readily determined by those skilled in the art. For example, viscous samples usually are tested at 50% dilution, whereas nonviscous samples are not diluted. The test sample is placed in a sterile 250 ml beaker equipped with a magnetic stirring bar and the sample volume is brought to 100 ml, if needed, with sterile deionized water. All testing is performed in triplicate, the results are combined, and the average log reduction is reported.

The choice of contact time period also is at the discretion of the investigator. Any contact time period can be chosen. Typical contact times range from 15 seconds to 5 minutes, with 30 seconds and 1 minute being typical contact times. The contact temperature also can be any temperature, typically room temperature, or about 25 degrees Celsius.

The bacterial suspension, or test inoculum, is prepared by crowing a bacterial culture on any appropriate solid media (e.g., agar). The bacterial population then is washed from the agar with sterile physiological saline and the population of the bacterial suspension is adjusted. to about 108 colony forming units per ml (cfu/ml).

The table below lists the test bacterial cultures used in the following tests and includes the name of the bacteria, the ATCC (American Type Culture Collection) identification number, and the abbreviation for the name of the organism used hereafter.

| Organism Name | ATCC # | Abbreviation |
|---|---|---|
| Staphylococcus aureus | 6538 | S. aureus |
| Escherichia coli | 11229 | E. coli |
| Klebsiella pneumoniae | 10031 | K. pneum. |
| Salmonella choleraesuis | 10708 | S. choler. |

S. aureus is a Gram positive bacteria, whereas E. coli, K. pneum, and S. choler. are Gram negative bacteria.

The beaker containing the test composition is placed in a water bath (if constant temperature is desired), or placed on a magnetic stirrer (if ambient laboratory temperature is desired). The sample then is inoculated with 1.0 ml of the test bacteria suspension. The inoculum is stirred with the test composition for the predetermined contact time. When the contact time expires, 1.0 ml of the test composition/bacteria mixture is transferred into 9.0 ml of Tryptone-Histidine-Tween Neutralizer Solution (THT). Decimal dilutions to a countable range then are made. The dilutions can differ for different organisms. Plate selected dilutions in triplicate on TSA+ plates (TSA+ is Trypticase Soy Agar with Lecithin and Polysorbate 80). The plates then are incubated for 25±2 hours, and the colonies are counted for the number of survivors and the calculation of percent or log reduction. The control count (numbers control) is determined by conducting the procedure as described above with the exception that THT is used in place of the test composition. The plate counts are converted to cfu/ml for the numbers control and samples, respectively, by standard microbiological methods.

The log reduction is calculated using the formula

Log reduction=$\log_{10}$ (numbers control)–$\log_{10}$ (test sample survivors).

The following table correlates precent reduction in bacteria population to log reduction:

| % Reduction | Log Reduction |
|---|---|
| 90 | 1 |
| 99 | 2 |
| 99.9 | 3 |
| 99.99 | 4 |
| 99.999 | 5 | b) Preparation of saturated solutions of TCS in water: A four liter flask was equipped with a 3-inch magnetic stir bar and charged with approximately 7.5 grams (g) TCS and 3 liters (L) of water. The flask then was placed in a water bath, stirred, and heated (40–45° C.) for at least 8 hours. The flask containing the resulting TCS/water suspension was removed from the water bath, and the warm suspension filtered through a Coors #32-H porcelain Büchner funnel equipped with Whatman #40 (5.5 cm) filter paper. The filtering assembly was attached to a two liter vacuum filter flask, and filtration was conducted in batches. The filtrate then was transferred to another four liter flask and allowed to cool. Typically, fine needles of TCS crystals formed after the filtrate was stored at room temperature for a few days.

For some time kill studies, the TCS solution was refiltered at room temperature before use in the study. For other time kill studies, a small amount of crystalline TCS was allowed to remain in the test container to ensure saturation in the event of a temperature change. It was assumed that TCS crystals present in the time kill test vessel would not affect test results because crystalline TCS is unavailable to act on the bacteria (i.e., is not solubilized).

To determine the concentration of TCS in the water solutions, filtered samples (in triplicate) were analyzed by HPLC. The apparatus used to filter the solutions was a Whatman AUTOVIAL®, with 0.45 *m PTFE membrane and glass microfiber prefilter, cat. No. AV 125UORG. TCS concentrations were calculated using a linear regression line fit (Microsoft EXCEL® software) to TCS/IPA standards included on the same HPLC run.

c) Preparation of aqueous TCS/surfactant compositions: A French square bottle was charged with a solution containing a variable concentration of a surfactant and 0.3%, by weight, TCS. The mixture was stirred and heated (35–40° C.) for several hours until the TCS was solubilized. Variable transformer-controlled heat lamps were used for warming and the temperature of the solution was monitored with a digital thermometer. Stirring then was stopped, TCS seed crystals (about 1 mg) were added to the solution, and the mixture was allowed to stand at about 20° C. In a few days, crystals were observed on the bottom of solution containers in which the maximum solubility of TCS was exceeded.

The approximate concentration of surfactant necessary to almost completely solubilize the 0.3% TCS was determined by use of an experimental design in which the concentration of surfactant was serially reduced by a factor of two over a series of test samples until the approximate saturation point of TCS in the surfactant was observed. Then the difference in concentration (saturated vs. just solubilized) was halved until a close endpoint for TCS saturation could be determined. The saturation point of TCS/surfactant compositions could be effectively estimated with small-scale (15 to 100 mL) samples, but about 600–800 g samples were required to obtain reliable final results. The initial ranges, therefore, were established with small-scale samples, and the final concentrations were determined using larger-scale samples.

d) Preparation of compositions containing TCS and a solvent or solvent/hydrotrope combination: TCS first was dissolved in the solvent used in the composition. Water then was added to the TCS/solvent composition, followed by the addition of about 1 mg of TCS seed crystals, and the resulting mixture was allowed to stand at about 20° C. to crystallize. In compositions containing a solvent, hydrotrope, and surfactant, the TCS was dissolved in the solvent as above, and then the hydrotrope and surfactant were added to the TCS/solvent solution. The resulting mixture then was diluted to the batch total with water. Adjustment of pH also was performed, if required. The mixture was stirred at room temperature for about an hour, seed TCS was added, and the mixture allowed to stand and crystallize as above. The determination of the TCS saturation point described above also was used (i.e., halving surfactant concentrations). Methods similar to the above for determination of maximum additive concentration have been described in the literature. For example, P. H. Elworthy et al., "Solubilization by surface-active agents and its application in chemistry and biological sciences," Chapman and Hall, Ltd., London, pp. 62–65 (1968), describes detecmination of concentrations near saturation by observing turbidity of the mixture. A similar technique was used by observing the sample at right angles with a high-intensity light from a small flashlight equipped with a beam focusing attachment (i.e., MINI MAGLITE® AA, MAG Instruments, California, USA). This method also was used with solutions very near to saturation to enhance observation of small amounts of crystals formed on the bottom of containers.

e) Preparation of samples: The preparation of all samples involved equipment and procedures normally employed in formula development laboratories. All percents were by weight based on the active level of each ingredient.

f) Summary formula descriptions in example tables: A typical table entry for a test composition is "0.3TCS/5DPG/15SXS/0.75ALS." This entry is defined as 0.3% triclosan (TCS), 5% dipropylene glycol (DPG), 15% sodium xylene sulfonate (SXS), 0.75% ammonium lauryl sulfate (ALS), and the remainder of the formula is water (typically with 0.2%, by total weight, of a citrate/phosphate buffer designed to provide a pH of about 6).

g) Pigskin deposition test: The following protocol is a general description of how the relative deposition efficiencies of various text compositions were determined. The substrate was pigskin, which is similar to human skin in color and texture, and in having a layer of subcutaneous fat. Pigskin is well known in the art as a model substrate for deposition assays. The test samples (0.03 to 3 grams) first are weighed into 16 mL vials. The sample size varied depending upon the nature of the test, i.e., different test protocols were used to simulate different use situations from high dilution to neat application. Next, the pigskin samples (Brennen Medical, Inc., Mediskin I-Zenoderm, S-106) were cut into ⅜ inch diameter disks with a punch. If the protocol required addition of water to the sample, a controlled amount of water was added to the sample in the vial just prior to exposure of the pigskin disks to the sample. Typically, the water/sample mix was dispersed for 15 seconds by agitating the sample with a laboratory vortexer attached to a timer. Four pigskin disks then were added, and the vial was agitated for another 30 seconds. The sample/water mixture then was drained with a pipette, and the pigskin was rinsed with 30 second vortexing in like fashion with 3×3 mL aliquots of distilled water. On the last rinse, any remaining foam was carefully removed with a pipette. The pigskins then were extracted overnight with isopropyl alcohol, and the extracts were analyzed by high pressure liquid chromatography (HPLC) for the amount of active ingredient extracted. Control/recovery experiments were performed prior to testing to ensure that the isopropyl alcohol extraction procedure could adequately dissolve a known amount of active compound from the pigskin disks.

h) Dilution phase stability test: This test provides an indication of the ability of various test compositions to deposit topically active compounds on the test substrate. It also demonstrated the fundamental difference between the dilution behavior of a present composition and traditional compositions having solubilized actives. The test was conducted by diluting a given composition with a known amount of water (typically 25:50, 50:50, 75:25; all composition:water proportions weight/weight), then observing the formulation over an extended period of time. The diluted samples were maintained at about 22° C. to 25° C. The appearance of a separate phase (e.g., turbidity, crystals, and/or precipitate) was considered an indication of active compound deposition. As demonstrated by the examples, the compositions typically exhibited a sign of phase separation within about 0.25 to 1 hour after dilution.

i) Volar forearm deposition test: An in vivo deposition test was performed using a small number of volunteer panelists and three sites on the volar forearms. The sites were designated L1, L2, L3, and R1, R2, R3, for left and right arms, respectively. Site 1 was closest to the wrist, site 2 was in the middle of the forearm, and site 3 was near the inner elbow.

Sites L3 and R3 were chosen as blank control sites to give baseline values on untreated skin. These sites were treated as follows. A glass sampling device was held over the test site. One ml of isopropyl alcohol was placed on the skin area confined by a glass cylinder, and the area (about 4.5 $cm^2$) was scrubbed gently with a smooth glass rod for 60 seconds. When scrubbing was complete, the isopropyl alcohol extract was transferred to a preweighed 16 mL vial using a fine-tipped 1 mL pipette.

Treated sites (L1, L2, R1, and R2) were processed as follows. The skin site was wet by placing the site under running, warm water for about 15 seconds. Test product was applied to the designnated wet skin site, and the site was scrubbed gently for 30 seconds with the first and second fingers of the panelist's hand, followed by 15 seconds of rinsing with a gentle flow of warm tap water. The site then was gently pat dried with a paper towel, and extracted as above for L3 and R3, except three 1 mL extractions were made at each site.

The isopropyl alcohol extracts then were processed as described above in the "Pigskin Deposition Test" (HPLC analysis). The use of preweighed vials allowed for adjustments to be calculated for small solvent losses encountered in the extraction procedure.

Table 2 summarizes the results of time kill tests performed on TCS/water compositions. Two series of results, I and II, demonstrate the effect of % saturation in TCS/water compositions, i.e., that within a given test series, reduction in % saturation produces a concomitant reduction in time kill efficacy.

TABLE 2

Time Kill Results for Saturated TCS/Water Compositions

| | | LOG REDUCTION | | | | | | | |
|---|---|---|---|---|---|---|---|---|---|
| | TCS | S. aureus | | E. coli | | K. pneum. | | S. chol. | |
| Sample | (g/mL) (by HPLC) | 1 min/ or t | 5 min. | 1 min/ or t | 5 min. | 1 min/ or t | 5 min. | 1 min/ or t | 5 min. |
| I | 100% sat'd. | $9.3 \times 10^{-7}$ | 1.07/15 s | >3.91 | 0.44/15 s | >4.06 | 0.32/15 s | >4.00 | |
| | 50% sat'd. | $3.9 \times 10^{-7}$ | 0.03/15 s | 1.71 | 0.13/15 s | 1.15 | 0.21/15 s | 2.76 | |
| | 10% sat'd. | $6.7 \times 10^{-8}$ | 0.03/15 s | 0.02 | 0.06/15 s | 0.08 | 0/15 s | 0.14 | |
| II | 100% sat'd. | $9.6 \times 10^{-6}$ | 3.93 | | 1.76 | | 2.85 | | 2.15 |
| | 50% sat'd. | $4.9 \times 10^{-6}$ | 0.24 | | 0.26 | | 0.35 | | 1.28 |

Comparing the data in Tables 2 and 3 shows that at the very lowest concentration of TCS (i.e., 5 to 10 ppm), the efficacy of time kill is reduced compared to samples containing higher levels of TCS. For example, a sample in Table 2 containing 0.93 ppm TCS has a log reduction of 0.44 after 15 seconds vs. E. coli, whereas a sample in Table 3 containing 484 ppm TCS had a log reduction of 4.13 after 15 seconds vs. the same organism. This effect is more apparent at shorter-contact time periods. Another example, in more complex compositions is illustrated in samples in Table 3, i.e., 50 ppm TCS (est.)/10% PG/5% SXS vs. (448 ppm TCS (est.)/20% PG/10% SXS). The sample with the higher TCS concentration showed at least a log improvement in bacterial reduction after 1 minute. The data in Table 3 also show differences in efficacy when different solvents/hydrotropes are used with approximately the same TCS concentrations.

TABLE 3

TCS in Solvent and/or Hydrotrope Systems

| TCS (ppm) | Solvent/ Hydrotrope | S. aureus | | E. coli | |
|---|---|---|---|---|---|
| | | sec. | 1 min. | sec. | 1 min. |
| 112 (est) | 17% IPA | | >4.42 | | >3.56 |
| 0 | 17% IPA | | 0.42 | | −0.24 |
| 110 (est) | 23.85% PG | | >4.39 | | 2.37 |
| 342 | 40.01% PG | 4.97[1]/30[2] | >5.17 | 4.29/30 | >4.67 |
| 484 | 41.86% PG | >3.46/15 | >3.46 | 4.13/15 | >4.38 |
| 510 | 42.53% PG | >5.17/30 | >5.17 | 4.47/30 | >4.67 |
| 723 | 44.20% PG | >3.46/15 | >3.46 | >4.38/15 | >4.38 |
| 603 | 45.05% PG | >4.69/15 | >4.69 | 4.21/15 | >4.65 |
| 895 | 47.52% PG | >5.17/30 | >5.17 | 4.42/30 | >4.67 |
| 1385 | 50.00% PG | >4.49/15 | >4.49 | 4.45/15 | >4.65 |
| 0 | 50.00% PG | 0.15/15 | 0.13 | 0.25/15 | 0.26 |
| 0 | 75.00% PG | 1.20/15 | 2.35 | 0.35/15 | 1.73 |
| 63 | 5% SXS | | >4.43 | | 0.96 |
| 0 | 5% SXS | | 0.33 | | −0.15 |
| 57 | 5% SCS | | 3.64 | | 0.80 |
| 0 | 5% SCS | | −0.05 | | −0.11 |
| 448 (est) | 20% PG/10% SXS | >4.14/30 | >4.14 | >5.25/30 | >5.25 |
| 0 | 20% PG/10% SXS | 0.05/30 | 0.05 | 1.16/30 | 1.35 |
| 50 (est) | 10% PG/5% SXS | | 3.42 | | 3.18 |
| 0 | 10% PG/5% SXS | | 0.05 | | 0.35 |
| 50 (est) | 10% PG/5% SXS | | 0.59 | | 4.96 |
| 0 | 10% PG/5% SCS | | −0.03 | | 0.96 |
| 502 (est) | 14.5% DPG/10% SXS | >3.63/30 | >3.63 | >4.44/30 | >4.44 |
| 0 | 14.5% DPG/10% SXS | 0.03/30 | 0.04 | 0.26/30 | 0.17 |

| TCS (ppm) | Solvent/ Hydrotrope | K. pneum. | | S. chol. | |
|---|---|---|---|---|---|
| | | sec. | 1 min. | sec. | 1 min. |
| 112 (est) | 17% IPA | | >4.11 | | >3.79 |
| 0 | 17% IPA | | 0.89 | | 1.23 |
| 110 (est) | 23.85% PG | | | | |
| 342 | 40.01% PG | 4.33/30 | 5.29 | 2.52/30 | 3.51 |
| 484 | 41.86% PG | 2.96/15 | >3.44 | 1.14/15 | 2.31 |
| 510 | 42.53% PG | 4.61/30 | >5.64 | 1.56/30 | 2.27 |
| 723 | 44.20% PG | >3.44/15 | >3.44 | 1.29/15 | 2.59 |
| 603 | 45.05% PG | 2.60/15 | 4.79 | 1.79/15 | >4.50 |
| 895 | 47.52% PG | 5.26/30 | >5.64 | 2.92/30 | 4.33 |
| 1385 | 50.00% PG | 3.26/15 | >5.04 | 2.69/15 | >4.59 |
| 0 | 50.00% PG | 0.54/15 | 0.63 | 0.17/15 | 0.24 |
| 0 | 75.00% PG | 1.98/15 | >3.44 | 1.34/15 | 3.56 |
| 63 | 5% SXS | | | | |
| 0 | 5% SXS | | | | |

TABLE 3-continued

TCS in Solvent and/or Hydrotrope Systems

| | | | | | |
|---|---|---|---|---|---|
| 57 | 5% SCS | | | | |
| 0 | 5% SCS | | | | |
| 448 (est) | 20% PG/10% SXS | >4.32/30 | >4.32 | 3.17/30 | >3.68 |
| 0 | 20% PG/10% SXS | 0.22/30 | 0.37 | 0.25/30 | 1.29 |
| 50 (est) | 10% PG/5% SXS | | | | |
| 0 | 10% PG/5% SXS | | | | |
| 50 (est) | 10% PG/5% SXS | | | | |
| 0 | 10% PG/5% SCS | | | | |
| 502 (est) | 14.5% DPG/10% SXS | >4.14/30 | >4.14 | >4.14/30 | >4.14 |
| 0 | 14.5% DPG/10% SXS | 0.34/30 | 0.39 | 0.36/30 | 0.47 |

[1]log reduction; and
[2]seconds

The compositions of the present invention contain a surfactant, which potentially can reduce the efficacy of the antibacterial agent. The following examples show the unexpected benefits achieved by compositions of the present invention.

EXAMPLE 1

In this example, a composition of the present invention was compared to three commercially available antibacterial cleansing compositions in a time kill test using a contact time of 5 minutes. A composition of the present invention (Product A) was a saturated solution containing 0.3% triclosan in a 1.5% aqueous sodium lauryl sulfate (SLS). The three commercially available antibacterial compositions having unknown triclosan concentrations, were Jergens Antibacterial (JA) Hand Soap, a product of Andrew Jergens Inc.; Clean and Smooth (CS), a product of Benckiser; and Soft Soap (SSp), a product of Colgate Palmolive.

| Product | Triclosan (%) | % Saturation[3] | Log Reduction at 5 minutes (time kill) | | | |
|---|---|---|---|---|---|---|
| | | | S. aureus | E. coli | K. pneum. | S. chol. |
| A | 0.3 | 100 | >4.47 | >4.41 | >4.36 | 4.67 |
| JA | Unk.[2] | Unk. | 2.48 | 0.20 | 0.18 | —[1] |
| CS | Unk. | Unk. | 2.80 | 0.00 | 0.10 | — |
| SSp | Unk. | Unk. | 1.62 | 0.00 | 0.20 | — |

[1]"—" means not tested;
[2]"Unk." means Unknown; and
[3]"% saturation" means percent saturation of TCS in the continuous aqueous phase.

Example 1 demonstrates the surprising improvement in log reduction of bacteria populations provided by an inventive composition compared to currently available commercial antibacterial compositions. Thus, an aqueous composition containing triclosan in SLS, at 100% saturation, offers significantly greater antibacterial efficacy than any of the three commercial products tested, against Gram positive and against Gram negative microorganisms, both of which can present a significant health threat to consumers.

EXAMPLE 2

This example demonstrates that the antibacterial activity of an inventive composition is attributable to the active antibacterial agent, as opposed to the surfactant. Test compositions A-1 and A-2 were prepared. Composition A-1 is a solution containing 0.3% triclosan, 1.35% ammonium lauryl sulfate, with the balance being water. Composition A-1 is 100% saturated with triclosan. Composition A-2 is a "placebo," i.e., an aqueous 1.35% ammonium lauryl sulfate solution that is free of the active antibacterial agent.

| Product | Triclosan (%) | % Saturation[3] | Log Reduction at 5 minutes (time kill) | | | |
|---|---|---|---|---|---|---|
| | | | S. aureus | E. coli | K. pneum. | S. chol. |
| A-1 | 0.30 | 100 | >3.61 | 3.16 | >4.39 | 3.73 |
| A-2 | 0 | 0 | >3.61 | 0.25 | 0.15 | 0.04 |

The inventive composition A-1 clearly provided an excellent, broad spectrum antibacterial activity, whereas the "placebo" composition A-2 exhibited an extremely limited spectrum of activity. Composition A-2 has especially poor efficacy against Gram negative organisms. Control of Gram negative organisms is of particular concern to consumers because such organisms present a significant health threat. The excellent broad spectrum activity of composition A-1 clearly shows that the antibacterial activity is unambiguously attributed to the presence of the antibacterial agent in the continuous aqueous phase.

EXAMPLE 3

In this example, a solvent, (i.e., propylene glycol (PG)) was used to solubilize triclosan in an aqueous carrier. No hydrotrope or surfactant was present. Composition A-3 contained 0.0872% by weight triclosan, 47.5% aqueous PG, and the balance being water. Composition A-3 was 100% saturated with triclosan and is a composition of the present invention. Test composition A-4 was a "placebo" consisting of 47.5% PG, by weight, and the balance water. This example illustrates an added advantage of including an optional hydric solvent in the composition. In particular, it was observed that the excellent broad spectrum activity illustrated in earlier examples at contact times of 1 and 5 minutes can be achieved in the presence of the hydric solvent at a contact time of 30 seconds. This example further demonstrates that the antibacterial activity of a present composition is unambiguously attributable to the presence of the antibacterial agent.

| Product | Triclosan (%) | % Saturation | Log Reduction at 30 seconds (time kill) | | | |
|---|---|---|---|---|---|---|
| | | | S. aureus | E. coli | K. pneum. | S. chol. |
| A-3 | 0.0872 | 100 | >5.17 | 4.42 | 5.26 | 2.92 |
| A-4 | 0.0 | 0 | 0.15 | 0.25 | 0.54 | 0.17 |

EXAMPLE 4

This example illustrates the effect of the identity of the surfactant on the antibacterial activity of the composition. The test results summarized below were performed on a wide variety of compositions containing either an anionic surfactant or representative cationic, anionic/nonionic, amphoteric, and nonionic surfactants. The percent saturation of TCS in the compositions of this example is at least about 90%.

| Surfactant Type | Active Conc. | Surfactant and Amount | S. aureus (1 min.) | E. coli (1 min.) |
|---|---|---|---|---|
| Anionic | 0.3% TCS | 1.6% Sodium Lauryl Sulfate (SLS) | ++++ | ++++ |
| Anionic | 0.3% TCS | 1.35% Ammonium Lauryl Sulfate | ++++ | +++ |
| Anionic | 0.3% TCS | 1.5% Triethanolamine Lauryl Sulfate (TEALS) | +++ | ++++ |
| Anionic | 0.3% TCS | 5% Sodium Octyl Sulfate (SOS) | ++++ | ++++ |
| Anionic | 0.3% TCS | 9.5% Sodium 2-Ethylhexyl Sulfate (S2EHS) | ++++ | ++++ |
| Cationic | 0.3% TCS | 1.5% Lauramine Oxide (LAO) | ++++ | ++++ |
| Anionic | 0.3% TCS | 2.5% Sodium Decyl Sulfate (SdecS) | ++++ | + |
| Anionic | 0.3% TCS | 2.5% Sodium Tridecyl Sulfate (SC13S) | ++++ | 0 |
| Anionic | 0.3% TCS | 1.5% Lithium Lauryl Sulfate (LLS) | ++++ | 0 |
| Anionic | 0.3% TCS | 1.5% Potassium Coccate (KCO) | ++++ | + |
| Anionic | 0.3% TCS | 2.0% Methyl Ester Sulfonate (MES) | ++++ | 0 |
| Anionic | 0.3% TCS | 1.25% Sodium Lauroyl Sarcosinate (SLSarc) | ++++ | 0 |
| Anionic | 0.3% TCS | 1% Sodium Lauryl Sulfoacetate (SLSA) | +++ | 0 |
| Anionic | 0.3% TCS | 3% C10 (Linear) Sodium Diphenyl Oxide Disulfonate (L10-45) | ++++ | 0 |
| Anionic | 0.3% TCS | 1.5% Disodium Lauryl Sulfosuccinate (DSLrylScet) | +++ | 0 |
| Anionic/Nonionic | 0.3% TCS | 1.25% Sodium Lauryl Ether Sulfate, 1-mole EO (SLES-1) | ++++ | 0 |
| Anionic/Nonionic | 0.3% TCS | 1% Sodium Lauryl Ether Sulfate, 2-mole EO (SLES-2) | ++++ | 0 |
| Amphoteric | 0.3% TCS | 1.25% Sodium Cocamphoacetate (SCA) | 0 | 0 |
| Amphoteric | 0.3% TCS | 1.75% Cocamidopropyl Betaine (CAPB) | 0 | 0 |
| Anionic | 0.3% TCS | 1.25% Alpha-Olefin Sulfonate (AOS) | n/a | 0 |
| Anionic | 0.3% TCS | 1.5% Sodium Alkyl Sulfate, $C_{12-18}$(SC12–18S) | ++ | 0 |
| Anionic | 0.3% TCS | 1.5% Magnesium Lauryl Sulfate (MLS) | n/a | 0 |
| Anionic/Nonionic | 0.3% TCS | 2.0% Sodium Myreth-4 Carboxylate (NaNDX23-4) | 0 | 0 |
| Anionic/Nonionic | 0.3% TCS | 1.25% Disodium Laureth Sulfosuccinate (DSLSect) | ++ | 0 |
| Nonionic | 0.3% TCS | 2.5% Alkyl Polyglucose (APG) | 0 | 0 |
| Nonionic | 0.3% TCS | 4% Octoxynol-9 (TX100) | 0 | 0 |

Key: log reduction in time kill test
++++ >3.99
+++ >2.99
++ >1.99
+ >0.99
0 <0.99

The results summarized above demonstrate, unexpectedly, that antibacterial agents and anionic surfactants form highly effective antibacterial compositions when the % saturation of antibacterial agent in the composition is high, i.e., at least 50%. In addition, it was observed that, within a homologous series of surfactants, efficacy can vary (i.e., in the sodium alkyl sulfate homologous series, sodium lauryl sulfate and sodium octyl sulfate yielded high efficacy formulas). The efficacy with respect to the cation also is unexpected (i.e., sodium, ammonium, and triethanolammonium lauryl sulfates provided high efficacy formulas, whereas lithium and magnesium lauryl sulfates did not).

EXAMPLE 5

The following table summarizes the effect of surfactant identity on the antibacterial activity of the composition. This example expands upon the data provided in Example 4. The table includes results of tests performed on a wide variety of compositions containing either anionic surfactants or representative examples containing cationic, anionic/nonionic, amphoteric, and nonionic surfactants.

The results demonstrate that various anionic surfactants form highly effective systems. The surfactants associated with very high activity (i.e., a high log reduction for both Gram positive (S. aureus) and Gram negative (E. coli) bacteria) include sodium lauryl sulfate, sodium octyl sulfate, sodium 2-ethylhexyl sulfate, and lauramine oxide. However, it is possible that the high activity of the lauramine oxide containing composition was due primarily to the surfactant.

Series I (Lauryl Sulfates) demonstrates efficacy effects attributed to the cation. The sodium lauryl sulfate had the highest efficacy, wherein ammonium, monoethanolammonium and triethanolammonium exhibited intermediate efficacy. Lithium and magnesium sulfates exhibited low efficacy. Potassium lauryl sulfate was not tested because of its low solubility at room temperature.

Comparing Series I (Lauryl Sulfates) and Series II (Other Alkyl Sulfates) shows that efficacy varies within a homologous series (i.e., sodium n-alkyl sulfates). Sodium lauryl sulfate and sodium octyl sulfate yield high efficacy formulas, as does the branched chain surfactant, sodium 2-ethylhexyl sulfate.

The data in Series III (Alkyl Carboxylates) suggests that TCS/carboxylate compositions are not highly active against Gram negative bacteria, but are of acceptable activity against Gram positive bacteria.

The results for Series IV (EO-Containing Surfactants) confirm observations that ethylene oxide (EO) in surfactants tends to inactivate TCS. The activity of SLES-1 and SLES-2 vs. S. aureus is attributed to the anionic ("lauryl sulfate-like" character) of these anionic/nonionic surfactants.

The results for Series V (Miscellaneous Surfactants) shows that these compositions exhibit moderate to low activity, with the exception of lauramine oxide. The portion of high activity of LAO is attributed to the surfactant alone because of its quasi-cationic character. The remaining surfactant/TCS compositions in Series V showed varied activity vs. S. aureus (Gram positive) and very little activity vs. E. coli (Gram negative).

| Type | Active Conc. | Other Ingredients | S. aureus (30 s/1 min.) | E. coli (30 s/1 min.) |
|---|---|---|---|---|
| | | TCS in Simple Surfactant Systems | | |
| | | Series I-Lauryl Sulfates | | |
| Anionic | 0.3% TCS | 1.6% sodium lauryl sulfate (SLS) | >3.94/>3.94 | 4.36/4.36 |
| | 0% TCS | 1.6% sodium lauryl sulfate (SLS) | >3.94/>3.94 | 1.51/2.96 |
| Anionic | 0.3% TCS | 1.35% ammonium lauryl sulfate (ALS) | >3.97/>3.97 | 1.39/3.95 |
| | 0% TCS | 1.35% ammonium lauryl sulfate (ALS) | >3.97/>3.97 | −0.07/−0.02 |
| Anionic | 0.3% TCS | 1.5% monoethanolamine lauryl sulfate (MEALS) | 2.29/4.03 | 0.58/2.04 |
| Anionic | 0.3% TCS | 1.5% triethanolamine lauryl sulfate (TEALS) | 2.74/3.73 | 1.3/4.33 |
| Anionic | 0.3% TCS | 1.5% lithium lauryl sulfate (LLS) | —/4.1 | .51/.81 |
| Anionic | 0.3% TCS | 1.5% magnesium lauryl sulfate (MLS) | —/— | 0.45/0.52 |
| | | Series II-Other Alkyl Sulfates | | |
| Anionic | 0.3% TCS | 5% sodium octyl sulfate (SOS) | >4.39/>4.39 | >4.83/>4.83 |
| | 0% TCS | 5% sodium octyl sulfate (SOS) | 1.76/1.81 | >4.47/>4.47 |
| Anionic | 0.3% TCS | 9.5% sodium 2 ethylhexyl sulfate (S2EHS) | >4.34/>4.84 | >4.47/>4.47 |
| | 0% TCS | 9.5% sodium 2-ethylhexyl sulfate (S2EHS) | >3.39/>3.39 | >4.45/4.35 |
| Anionic | 0.3% TCS | 2.5% sodium decyl sulfate (SdedS) | >4.39/>4.39 | 0.59/1.23 |
| Anionic | 0.3% TCS | 2.5% sodium tridecyl sulfate (SC13S) | 3.24/>3.39 | −0.04/0.31 |
| Anionic | 0.3% TCS | 1.5% sodium alkyl sulfate, C12–18 (SC12–18S) | 2.09/2.85 | 0.06/0.01 |
| | | Series V-Miscellaneous Surfactants | | |
| Cationic | 0.3% TCS | 1.5% lauramine oxide (LAO) | >4.25/>4.25 | >4.63/>4.63 |
| | 0% TCS | 1.5% lauramine oxide (LAO) | 3.55/3.86 | 4.18/4.73 |
| Anionic | 0.3% TCS | 1.25% sodium lauroyl sarcosinate (SLSarc) | 4.04/4.34 | −0.05/0.04 |
| Anionic | 0.3% TCS | 1.5% disodium lauryl sulfosuccinate (DSLrylScct) | 2.95/4.06 | 0.02/0.16 |
| Anionic/ Nonionic | 0.3% TCS | 1.25% disodium laureth sulfo succinate (DSLScct) | 1.76/2.68 | 0.36/0.38 |
| Anionic | 0.3% TCS | 1% sodium lauryl sulfoacetate (SLSA) | 3.19/3.83 | −0.09/−0.03 |
| Anionic | 0.3% TCS | 2.0% methyl ester sulfonate (MES) | >4.64/>4.64 | 0.11/0.22 |
| Anionic | 0.3% TCS | 1.25% alpha-olefin sulfonate (AOS) | 1.34/— | 0.28/0.33 |
| Anionic | 0.3% TCS | 3% C10 (linear) sodium diphenyl oxide disulfonate (L10–45) | 2.77/4.04 | 0.18/0.23 |
| Amphoteric | 0.3% TCS | 1.25% sodium coco-amphoacetate (SCA) | −0.15/−0.20 | −0.17/−0.15 |
| Amphoteric | 0.3% TCS | 1.75% cocamidopropyl betaine (CAPB) | −0.09/−0.03 | 0.21/0.61 |
| Nonionic | 0.3% TCS | 2.5% alkyl polyflucose (APG) | −0.10/−0.17 | 0.01/−0.02 |

EXAMPLE 6

This example illustrates the effect of % saturation of TCS in surfactant compositions (i.e., compositions free of a hydric solvent and hydrotrope). The data summarized in the following table illustrate the effect of % saturation of TCS on the efficacy of TCS in TCS/surfactant/water compositions. Two sections of the table (i.e., TCS/ALS compositions vs. E. coli and TCS/SOS compositions vs. S. aureus) show a substantial decrease in antibacterial activity with decreasing % saturation. Also, 100% saturated samples (0.15% TCS/0.67% ALS) and (0.15% TCS/4.0% SOS) have an antibacterial activity approaching that of 100% saturated samples containing 0.3% TCS. In these two examples, the effects are seen clearly for organisms wherein the surfactant does not show a strong placebo kill effect.

Effect of % TCS Saturation on Antibacterial Efficacy

| | | Log Reduction | | |
|---|---|---|---|---|
| TCS %/ % Sat'n. | Surfactant | S. aureus (30 s/1 min) | E. coli (30 s/1 min) | K. pneum. (30 s/1 min) |
| 0.30/100 | 1.35% ALS | >3.97/>3.97 | 1.39/3.95 | |
| 0.27/90 | 1.35% ALS | >3.97/>3.97 | 0.61/2.89 | |
| 0.21/70 | 1.35% ALS | >3.97/>3.97 | 0.37/1.54 | |
| 0.15/50 | 1.35% ALS | >3.97/>3.97 | 0.09/1.17 | |
| 0.15/100 | 0.67% ALS | >3.97/>3.97 | 1.10/3.63 | |
| 0/0 | 1.35% ALS | >3.97/>3.97 | −0.07/−0.02 | |
| 0.30/100 | 1.60% ALS | >3.94/>3.94 | 4.36/4.36 | |
| 0.27/90 | 1.60% SLS | >3.94/>3.94 | 4.36/>4.46 | |
| 0.21/70 | 1.60% SLS | >3.94/>3.94 | 4.04/>4.46 | |
| 0.15/50 | 1.60% SLS | >3.94/>3.94 | 4.13/>4.46 | |
| 0.15/100 | 0.80% SLS | >3.94/>3.94 | 3.17/>4.46 | |
| 0/0 | 1.60% SLS | >3.94/>3.94 | 1.51/2.96 | |
| 0.30/100 | 5.75% SOS | 3.39/3.04 | | >4.44/3.98 |
| 0.27/90 | 5.75% SOS | 2.59/3.04 | | >4.44/>4.44 |
| 0.21/70 | 5.75% SOS | 1.59/1.82 | | >4.44/>4.44 |
| 0.15/50 | 5.75% SOS | 0.96/1.43 | | >4.44/>4.44 |
| 0.15/100 | 4.00% SOS | 2.90/3.20 | | >4.44/>4.44 |
| 0/0 | 5.75% SOS | 0.23/0.30 | | >4.44/>4.44 |

This example illustrates a composition of the present invention that can be used as a hand cleanser. This example further illustrates an embodiment of the invention wherein the antibacterial agent is present in combination with a surfactant, hydric solvent, and hydrotrope. Composition A-5 contains, by weight, 0.3% triclosan, 0.5% ammonium lauryl sulfate, 20% propylene glycol, and 10% sodium xylene sulfonate, with the balance water. Composition A-6, by weight, contains 0.1% triclosan, 0.125% ammonium xylene sulfonate, 20% propylene glycol, and 10% sodium xylene sulfonate the balance being water. Compositions A-5 and A-6 were 100% saturated with triclosan. Composition A-7 was a "placebo" containing, by weight, 0.5% ammonium lauryl sulfate, 20% propylene glycol, 10% sodium xylene sulfate, and the balance being water.

EXAMPLE 7

| | | | Log Reduction at 30 seconds (time kill) | | | |
|---|---|---|---|---|---|---|
| Product | Triclosan (%) | % Saturation[3] | S. aureus | E. coli | K. pneum. | S. chol. |
| A-5 | 0.3 | 100 | >3.84 | >4.41 | 3.56 | 3.26 |
| A-6 | 0.1 | 100 | >3.84 | >4.41 | 3.82 | 3.95 |
| A-7 | 0.0 | 0 | 3.22 | 3.36 | 0.74 | 1.77 |

This example illustrates two important features of the present invention. First, the absolute amount of triclosan, or other antibacterial agent, is less important than the percent saturation of antibacterial agent in the composition. For example, composition A-6 (containing 0.10% triclosan) was at least as effective as composition A-5 (containing 0.3% triclosan). The important feature is that both compositions were 100% saturated with triclosan. Second, Example 5 also clearly showed that the active antibacterial agent is responsible for the excellent broad spectrum antibacterial activity. Compositions A-5 and A-6 of the invention clearly outperformed the "placebo" composition A-7, which did not contain an active antibacterial agent.

EXAMPLE 8

This example demonstrates that a hydric solvent and hydrotrope can impart activity to an otherwise inactive surfactant and antibacterial agent composition. In the following table, all percentages are by weight, and the balance of all compositions is water. Composition B contains 1.35% ammonium lauryl sulfate (ALS) and 0.3% triclosan (TCS). Composition C contains 1.35% ALS and 0.0% TCS. Composition D contains 0.25% ALS, 14.4% DPG, 10.0% SXS, and 0.3% TCS, and Composition E contains 0.25% ALS, 14.4% DPG, 10.0% SXS with 0.0% TCS. Compound F contains 2.5% alkyl polyglucoside (APG™) with 0.3% TCS. Compound G contains 0.3% APG, 14.4% dipropylene glycol (DPG), 10% sodium xylene sulfonate (SXS), and 0.3% TCS. Compound H contains 0.3% APG with 14.4% DPG, 10% SXS, and 0.0% TCS. Composition I contains 1.25% sodium cocoamphoacetate (SCA) and 0.3% TCS. Composition J contains 0.25% SCA, 14.4% DPG, 10.0% SXS, and 0.3% TCS. Composition K contains 0.25% SCA, 14.4% DPG, 10.0% SXS, and 0.0% TCS. Composition L contains 1.75% cocamidopropyl betaine (CAPB) and 0.3% TCS. Composition M contains 0.25% CAPB, 14.4% DPG, 10% SXS, and 0.3% TCS. Composition N contains 0.25% CAPB, 14.4% DPG, 10% SXS, and 0.0% TCS. Composition 0 contains 4% octoxynol-9 (TRITON X-100™, TX100). Composition P contains 0.75% TX100, 14.4% DPG, 10.0% SXS, and 0.3% TCS. Composition Q contains 1.25% sodium lauryl ether sulfate (1 EO, SLES-1) and 0.3% TCS. Composition R contains 0.25% SLES-1, 14.4% DPG, 10.0% SXS, and 0.3% TCS.

| Composition | Triclosan % | Other Ingredients | % Saturation | Log Reduction (Time Kill) | |
|---|---|---|---|---|---|
| | | | | S. aureus (30 s/60 s) | E. coli (30 s/60 s) |
| B | 0.3 | 1.35% ALS | ~100 | >3.97/>3.97 | 1.39 3.95 |
| C | 0.0 | 1.35% ALS | 0 | >3.97/>3.97 | −0.07/−0.02 |
| D | 0.3 | 0.25% ALS 14.4% DPG 10.0% SXS | ~100 | >3.80/>3.80 | >4.38/>4.38 |

-continued

| Composition | Triclosan % | Other Ingredients | % Saturation | Log Reduction (Time Kill) | |
|---|---|---|---|---|---|
| | | | | S. aureus (30 s/60 s) | E. coli (30 s/60 s) |
| E | 0.0 | 0.25% ALS 14.4% DPG 10.0% SXS | ~100 | 1.31/1.54 | >2.49/>4.38 |
| F | 0.3 | 2.5% APG | ~100 | 1.19/1.21 | >4.69/4.69 |
| G | 0.3 | 0.3% APG 14.4% DPG 10.0% SXS | ~100 | >4.69/>4.69 | 4.50/4.58 |
| H | 0.0 | 0.3% APG 14.4% DPG 10.0% SXS | 0 | 1.19/1.21 | >4.69/>4 69 |
| I | 0.3 | 1.25% SCA | ~100 | −0.15/−0.20 | −0.17/−0.15 |
| J | 0.3 | 0.25% SCA, 14.4% DPG, 10.0% SXS | ~100 | >4.39/>4.39 | >4.73/>4.73 |
| K | 0.0 | 0.25% SCA, 14.4% DPG, 10.0% SXS | 0 | 0.86/0.88 | 2.90/4.05 |
| L | 0.3 | 1.75% CAPB | ~100 | −0.09/−0.03 | 0.21/0.61 |
| M | 0.3 | 0.25% SCA, 14.4% DPG, 10.0% SXS | ~100 | >4.39/>4.39 | >4.73/>4.73 |
| N | 0.0 | 0.25% SCA, 14.4% DPG, 10.0% SXS | 0 | 0.76/0.85 | 3.26/4.69 |
| O | 0.3 | 4% TX100 | ~100 | 0.16/0.15 | 0.43/0.46 |
| P | 0.3 | 0.75% TX100, 14.4% DPG, 10.0% SXS | ~100 | 0.53/0.58 | 3.59/>4.73 |
| Q | 0.3 | 1.25% SLES-1 | ~100 | >4.39/>4.39 | 0.41/0.46 |
| R | 0.3 | 0.25% SLES-1, 14.4% DPG, 10.0% SXS | ~100 | >4.34/>4.84 | >4.47/>4.47 |

The results of the time kill tests summarized in the above table very surprisingly show that the use of a hydric solvent and hydrotrope can impart a high antibacterial activity to surfactant/TCS combinations which alone exhibit only low to moderate efficacy (i.e., compare efficacy of composition F vs. G; I vs. J; L vs. M; and Q vs. R). The hydric solvent and hydrotrope also can render active compositions more active in shorter contact times (i.e., compare composition B vs. D). Especially surprising is the observation that a hydric solvent and hydrotrope can impart antibacterial efficacy against *E. coli* even in a composition containing a nonionic surfactant, i.e., octoxynol-9 (compare compositions O vs. P). This result is unexpected because polyethoxylated surfactants are known to inactivate phenolic antibacterial agents.

EXAMPLE 9

This example demonstrates the importance of % saturation in compositions containing a hydric solvent and hydrotrope. As observed in surfactant/TCS compositions, the relative % saturation of the antibacterial agent in the continuous aqueous phase of the composition also greatly influences the antibacterial activity of compositions containing a hydric solvent and hydrotrope. As the results summarized below illustrate, this influence on antibacterial activity is especially apparent with respect to the Gram negative bacterium, *K. pneum*.

| Composition | Triclosan % | Other Ingredients | % Saturation |
|---|---|---|---|
| S | 0.3 | 0.25% ALS, 14.4% DPG, 10.0% SXS | ~100 |
| T | 0.3 | 0.50% ALS, 14.4% DPG, 10.0% SXS | <S |
| U | 0.3 | 1.00% ALS, 14.4% DPG, 10.0% SXS | <S, T |
| V | 0.0 | 1.00% ALS, 14.4% DPG, 10.0% SXS | 0 |
| W | 0.3 | 1.20% ALS, 2.5% DPG, 10.0% SXS | ~100 |
| X | 0.3 | 2.5% ALS, 2.5% DPG, 10.0% SXS | <W |
| Y | 0.3 | 5.0% ALS, 2.5% DPG, 10.0% SXS | <W, X |
| Z | 0.0 | 5.0% ALS, 2.5% DPG, 10.0% SXS | 0 |

| Composition | Log Reduction (Time Kill) | | | |
|---|---|---|---|---|
| | S. aureus (30 s/60 s) | E. coli (30 s/60 s) | K. pneum. (30 s/60 s) | S. chol. (30 s/60 s) |
| S | >3.62/>3.52 | >4.59/>4.59 | 2.64/>3.84 | >3.85/>3.85 |
| T | >3.62/>3.62 | >4.59/>4.59 | 0.43/3.69 | >3.85/>3.85 |
| U | 1.67/2.31 | >4.59/>4.59 | 0.89/1.93 | 3.50/>3.85 |
| V | 1.10/1.29 | 3.42/4.59 | 0.28/0.67 | 2.17/>3.85 |
| W | — | — | — | 4.19/4.39 |
| X | — | — | — | 2.83/3.99 |
| Y | — | — | — | 2.39/3.22 |
| Z | — | — | — | 1.80/2.52 |

From the above data, it is clear that an increase in antibacterial efficacy, as measured by a time kill test, is associated with an increasing % saturation of the antibacterial agent in the aqueous phase of a given composition. This example further shows that compositions containing an antibacterial agent, surfactant, hydric solvent, and hydrotrope are effective when a high % saturation of active antibacterial agent is maintained.

EXAMPLE 10

This example, in conjunction with Example 9, illustrates the effect of % saturation of TCS in compositions containing a hydric solvent, hydrotrope, and surfactant. As previously observed with simple surfactant/TCS compositions, the relative % saturation of the antibacterial agent in the composition also influences the antibacterial activity of a composition containing a hydric solvent and/or a hydrotrope. From the data summarized in the table of Example 9 and the following table, it is clear that a substantial gain in antibacterial efficacy (as measured by a time kill test) is associated with an increasing % saturation of the antibacterial agent in a given type of composition. The tables demonstrate this effect from two different perspectives. The table in Example 9 shows the effect of changing the concentration of surfactant while maintaining the amount of other composition components constant. The following table shows the effect of varying the concentration of TCS while the concentration of all other components is kept constant. In the table of Example 9, the information relating to % saturation is relative because % saturation is difficult to directly calculate. Even using this qualitative data, the effect of % saturation of TCS is clear from both tables for all organisms tested.

Activity Dependent on % Saturation of TCS in Hydric Solvent/Hydrotrope/Surfactant Compositions

| Triclosan % | Other Ingredients | % Saturation | Log Reduction (Time Kill) | |
|---|---|---|---|---|
| | | | S. aureus (30 s/60 s) | E. coli (30 s/60 s) |
| 0.413 | 5% DPG, 15% SXS, 0.75% ALS | 100 | >4.55/>4.55 | >3.81/>3.81 |

-continued

Activity Dependent on % Saturation of TCS in Hydric Solvent/Hydrotrope/Surfactant Compositions

| Triclosan % | Other Ingredients | % Saturation | Log Reduction (Time Kill) | |
|---|---|---|---|---|
| | | | S. aureus (30 s/60 s) | E. coli (30 s/60 s) |
| 0.372 | 5% DPG, 15% SXS, 0.75% ALS | 90 | >4.55/>4.55 | 3.81/>3.81 |
| 0.330 | 5% DPG, 15% SXS, 0.75% ALS | 80 | >4.55/>4.55 | 3.46/>3.81 |
| 0.300 | 5% DPG, 15% SXS, 0.75% ALS | 73 | >4.55/>4.55 | 3.40/>3.81 |
| 0.248 | 5% DPG, 15% SXS, 0.75% ALS | 60 | 3.02/4.05 | 2.73/>3.81 |
| 0.207 | 5% DPG, 15% SXS, 0.75% ALS | 50 | 1.96/3.05 | 2.45/>3.81 |
| 0.166 | 5% DPG, 15% SXS, 0.75% ALS | 40 | 1.94/2.15 | 2.30/>3.81 |
| 0.103 | 5% DPG, 15% SXS, 0.75% ALS | 25 | 1.72/1.93 | 1.34/2.78 |

EXAMPLE 11

This example illustrates the effect of different levels of hydric solvent and hydrotrope on antibacterial efficacy. In particular, the data summarized below demonstrates the effect of varying the relative amounts of hydric solvent and hydrotrope. It should further be noted that the addition of a perfume (PF) and/or a preservative (DMDM) to the composition had only a modest effect, if any, on the antibacterial efficacy of the compositions.

|  |  |  | Log Reduction (Time Kill) | | | |
|---|---|---|---|---|---|---|
| Composition | Triclosan % | Other Ingredients | S. aureus (30 s/60 s) | E. coli (30 s/60 s) | K. pneum. (30 s/60 s) | S. chol. (30 s/60 s) |
| CCC | Calc 0.0502 | 14.5% DPG, 10.0% SXS | >3.63/>3.63 | >4.44/>4.44 | >4.14/>4.14 | >4.14/>4.14 |
| DDD | 0.0 | 14.5% DPG, 10.0% SXS | 0.03/0.04 | 0.26/0.17 | 0.34/0.39 | 0.36/0.47 |
| E | 0.0 | 0.25% ALS, 14.4% DPG, 10.0% SXS | 1.31/1.54 | 2.49/4.18 | 0.41/0.78 | 2.62/>4.04 |
| S | 0.3 | 0.25% ALS, 14.4% DPG, 10.0% SXS | >3.62/>3.62 | >4.59/>4.59 | 2.64/3.84 | >3.85/>3.85 |
| T | 0.3 | 0.50% ALS, 14.4% DPG, 10.0% SXS | >3.62/>3.62 | >4.59/>4.59 | 2.43/3.69 | >3.85/>3.85 |
| U | 0.3 | 1.00% ALS, 14.4% DPG, 10.0% SXS | 1.67/2.31 | >4.59/>4.59 | 0.89/1.93 | 3.50/>3.85 |
| V | 0.0 | 1.00% ALS, 14.4% DPG, 10.0% SXS | 1.10/1.29 | 3.42/4.59 | 0.28/0.67 | 2.17/>3.85 |
| AA | 0.3 | 0.75% ALS, 5.0% DPG, 10.0% SXS |  |  | 0.95/2.00 |  |
| BB | 0.3 | 0.75% ALS, 5.0% DPG, 12.5% SXS |  |  | 1.77/3.36 |  |
| CC | 0.3 | 0.75% ALS, 5.0% DPG, 15.0% SXS |  |  | 3.49/>3.69 |  |
| DD | 0.3 | 0.75% ALS, 5.0% DPG, 17.5% SXS |  |  | >3.69/>3.69 |  |
| EE | 0.3 | 0.75% ALS, 5.0% DPG, 20.0% SXS |  |  | >3.69/>3.69 |  |
| FF | 0.3 | 0.75% ALS, 7.5% DPG, 10.0% SXS |  |  | 0.81/2.87 |  |
| GG | 0.3 | 0.75% ALS, 7.5% DPG, 12.5% SXS |  |  | 1.72/4.21 |  |
| HH | 0.3 | 0.75% ALS, 7.5% DPG, 15.0% SXS |  |  | 3.04/4.31 |  |
| II | 0.3 | 0.75% ALS, 7.5% DPG, 17.5% SXS |  |  | >4.41/>4.41 |  |
| JJ | 0.3 | 0.75% ALS, 7.5% DPG, 20.0% SXS |  |  | >4.41/>4.41 |  |
| KK | 0.3 | 1.0% ALS, 5.0% DPG, 10.0% SXS |  |  | 0.08/1.49 |  |
| LL | 0.3 | 1.0% ALS, 5.0% DPG, 12.5% SXS |  |  | 0.97/3.32 |  |
| MM | 0.3 | 1.0% ALS, 5.0% DPG, 15.0% SXS |  |  | 2.57/4.41 |  |
| NN | 0.3 | 1.0% ALS, 5.0% DPG, 17.5% SXS |  |  | >4.41/>4.41 |  |
| OO | 0.3 | 1.0% ALS, 5.0% DPG, 20.0% SXS |  |  | >4.41/>4.41 |  |
| PP | 0.3 | 1.0% ALS, 7.5% DPG, 10.0% SXS |  |  | 0.17/0.92 |  |
| QQ | 0.3 | 1.0% ALS, 7.5% DPG, 12.5% SXS |  |  | 0.92/2.94 |  |
| RR | 0.3 | 1.0% ALS, 7.5% DPG, 15.0% SXS |  |  | 2.92/3.69 |  |
| SS | 0.3 | 1.0% ALS, 7.5% DPG, 17.5% SXS |  |  | >3.69/>3.69 |  |
| TT | 0.3 | 1.0% ALS, 7.5% DPG, 20.0% SXS |  |  | >3.69/>3.69 |  |
| UU | 0.3 | 0.75% ALS, 5.0% DPG, 15.0% SXS | 3.79/>4.64 | >4.57/>4.57 | 4.07/>4.69 | >3.97/>3.97 |
| VV | 0.3 | 0.75% ALS, 5.0% DPG, 15.0% SXS | 3.07/3.76 | 4.01/>4.34 | 3.40/4.46 | >4.04/>4.04 |
| WW | 0.0 | 0.75% ALS, 5.0% DPG, 15.0% SXS | 0.79/0.90 | >4.34/>4.34 | 0.41/1.53 | >4.04/>4.04 |
| XX | 0.3 | 0.75% ALS, 10.0% DPG, 10.0% SXS |  | >4.78/>4.78 | 0.67/1.46 |  |
| YY | 0.3 | 0.75% ALS, 10.0% DPG, 20.0% SXS |  | >4.78/>4.78 | >4.17/>4.17 |  |
| ZZ | 0.0 | 0.75% ALS, 10.0% DPG, 20.0% SXS |  | >4.78/>4.78 | >4.17/>4.17 |  |
| AAA | 0.3 | 0.75% ALS, 14.4% DPG, 10% SXS |  | >4.95/>4.95 |  |  |
| BBB | 0.0 | 0.75% ALS, 14.4% DPG |  | 0.28/0.28 |  |  |

It was observed that for compositions S, T, and U, the antibacterial activity against *S. aureus* and *K. pneum.* increases, especially, with a decreasing wt % of ALS surfactant (i.e., an increase in % saturation of TCS). Compositions CC, HH, MM, and RR demonstrate that about 15% SXS, or more, is preferred to exhibit high activity against *K. pneum.* in compositions containing a hydric solvent and a hydrotrope. This observation suggests that the hydrotrope may be acting as an adjuvant for the TCS because the time required for a substantial antibacterial kill, i.e., log reduction of at least 2, is reduced.

EXAMPLE 12

The data summarized in the following table support a theory that the two primary factors for improved antibacterial efficacy are the relative amounts of surfactant and hydrotrope to the amount of antibacterial agent in compositions containing a surfactant, hydric solvent, and antibacterial agent. A higher percentage of surfactant can reduce the % saturation, and thereby decrease the antimicrobial activity of the composition. On the other hand, a higher percentage of hydrotrope appears to provide a higher activity against certain organisms, like *K. pneum.* and *S. choler.* It is theorized that the higher percentage of hydrotrope in the composition provides a greater amount of active antibacterial compound in the aqueous (i.e., nonmicellar) phase of the composition, thereby providing a higher time kill activity. The solvent, therefore, may be acting as both an additive to enhance antimicrobial activity and to provide better physical stability in these compositions.

|  |  |  | Log Reduction (Time Kill) | | | |
|---|---|---|---|---|---|---|
| Composition | Triclosan % | Other Ingredients | S. aureus (30 s/60 s) | E. coli (30 s/60 s) | K. pneum. (30 s/60 s) | S. chol. (30 s/60 s) |
| CCC | Calc. 0.0502 | 14.5% DPG, 10.0% SXS | >3.63/>3.63 | >4.44/>4.44 | >4.14/>4.14 | >4.14/>4.14 |
| DDD | 0.0 | 14.5% DPG, 10.0% SXS | 0.03/0.04 | 0.26/0.17 | 0.34/0.39 | 0.36/0.47 |
| EEE | 0.3% TCS | 0.25% ALS, 14.4% DPG, 10.0% SXS | >3.80/>3.80 | >4.38/>4.38 | 3.54/4.07 | >4.04/>4.04 |
| FFF | 0% TCS | 0.25% ALS, 14.4% DPG, 10.0% SXS | 1.31/1.54 | 2.49/4.18 | 0.41/0.78 | 2.62/>4.04 |

-continued

|  |  |  | Log Reduction (Time Kill) | | | |
|---|---|---|---|---|---|---|
| Composition | Triclosan % | Other Ingredients | *S. aureus* (30 s/60 s) | *E. coli* (30 s/60 s) | *K. pneum.* (30 s/60 s) | *S. chol.* (30 s/60 s) |
| GGG | 0.3% TCS | 0.25% ALS, 14.4% DPG, 10.0% SXS | >3.62/>3.62 | >4.59/>4.59 | 2.64/3.84 | >3.85/>3.85 |
| HHH | 0.3% TCS | 0.5% ALS, 14.4% DPG, 10.0% SXS | >3.62/>3.62 | >4.59/>4.59 | 2.43/3.69 | >3.85/>3.85 |
| III | 0.3% TCS | 1% ALS, 14.4% DPG, 10.0% SXS | 1.67/2.31 | >4.59/>4.59 | 0.89/1.93 | 3.50/>3.85 |
| JJJ | 0% TCS | 1% ALS, 14.4% DPG, 10.0% SXS | 1.10/1.29 | 3.42/4.59 | 0.28/0.67 | 2.17/>3.85 |
| KKK | 0.4% TCS | 0.25% ALS, 14.4% DPG, 10.0% SXS, 0.05% PF | >4.59/>4.59 | >4.70/>4.70 | 4.11/>4.41 | >4.04/>4.04 |
| LLL | 0.3% TCS | 0.25% ALS, 14.4% DPG, 10.0% SXS, 0.05% PF | >4.59/>4.59 | >4.70/>4.70 | 4.06/>4.41 | >4.04/>4.04 |
| MMM | 0% TCS | 0.25% ALS, 14.4% DPG, 10.0% SXS, 0.05% PF | 1.70/2.19 | 3.97/4.70 | 0.50/1.43 | 3.04/>4.04 |
| NNN | 0.3% TCS | 0.25% ALS, 14.4% DPG, 10.0% SXS, 0.05% PF | >4.77/4.57 | >4.71/>4.71 | 3.90/>4.55 | >4.20/>4.20 |
| OOO | 0.3% TCS | 1% ALS, 14.4% DPG, 10.0% SXS, 0.05% PF | 3.18/4.09 | >4.71/>4.71 | 1.11.3.62 | 3.90/>4.20 |
| PPP | 0.3% TCS | 0.5% ALS, 14.4% DPG, 10.0% SXS, 0.05% PF | 4.39/>4.77 | >4.71/>4.71 | 3.00/>4.55 | >4.20/>4.20 |
| QQQ | 0% TCS | 1% ALS, 14.4% DPG, 10.0% SXS, 0.05% PF | 2.42/3.07 | 3.03/>4.71 | 0.65/0.98 | 2.29/4.10 |
| RRR | 0.3% TCS | 0.5% ALS, 14.4% DPG, 10.0% SXS, 0.05% PF | >4.71/>4.71 | >4.61/>4.61 | 2.10/3.97 | >3.87/>3.87 |
| SSS | 0.3% TCS | 0.6% ALS, 14.4% DPG, 10.0% SXS, 0.05% PF | >4.71/>4.71 | 4.61/>4.61 | 1.46/3.62 | >3.87/>3.87 |
| TTT | 0.3% TCS | 0.75% ALS, 14.4% DPG, 10.0% SXS, 0.05% PF | 4.28/>4.71 | >4.61/>4.61 | 1.42/3.34 | >3.87/ >3.87 |
| UUU | 0.3% TCS | 0.35% ALS, 10.0% DPG, 10.0% SXS, 0.05% PF | >4.23/>4.23 | >4.62/>4.62 | 3.30/4.63 | >3.87/>3.87 |
| VVV | 0.3% TCS | 0.5% ALS, 10.0% DPG, 10.0% SXS, 0.05% PF | >4.23/>4.23 | >4.62/>4.62 | 2.86/4.18 | >3.87/>3.87 |
| WWW | 0.3% TCS | 0.5% ALS, 7.5% DPG, 10.0% SXS, 0.05% PF | >4.23/>4.23 | >4.62/>4.62 | 2.63/3.77 | >3.87/>3.87 |
| XXX | 0.3% TCS | 0.6% ALS, 7.5% DPG, 10.0% SXS, 0.05% PF | >4.23/>4.23 | >4.63/>4.62 | 2.45/3.15 | >3.87/>3.87 |
| YYY | 0.3% TCS | 0.5% ALS, 14.4% DPG, 10.0% SXS, 0.05% PF, 0.25% DMDM | >3.83/>3.83 | >4.41/>4.41 | 2.89/>3.78 | >3.59/>3.59 |
| ZZZ | 0% TCS | 0.5% ALS, 14.4% DPG, 10.0% SXS, 0.05% PF, 0.25% DMDM | 1.48/2.10 | 3.84/4.41 | 0.38/1.12 | 2.09/3.45 |
| AAAA | 0.3% TCS | 0.75% ALS, 5.0% DPG, 10.0% SXS, 0.05% PF | >4.07/>4.07 | 3.90/4.03 | 1.97/3.66 | 3.24/3.24 |
| BBBB | 0.3% TCS | 0.75% ALS, 5.0% DPG, 7.5% SXS, 0.05% PF | >4.07/>4.07 | 3.10/4.28 | 0.25/2.23 | 0.91/2.80 |
| CCCC | 0.3% TCS | 0.75% ALS, 7.5% DPG, 10.0% SXS, 0.05% PF | >4.07/>4.07 | 3.82/4.53 | 1.49/3.56 | 2.93/3.34 |
| DDDD | 0.3% TCS | 0.75% ALS, 7.5% DPG, 7.5% SXS, 0.05% PF | >4.07/>4.07 | 3.47/4.18 | 0.19/2.00 | 0.99/2.76 |
| EEEE | 0.3 | 0.75% ALS, 5.0% tripropylene glycol (TPG), 10.0% SXS | 4.24/3.91 | >4.73/>4.73 | — | — |
| FFFF | 0.3 | 0.75% ALS, 10.0% TPG, 10.0% SXS | 2.59/3.65 | >4.73/>4.73 | — | — |
| GGGG | 0.0 | 0.75% ALS, 10.0% TPG, 10.0% SXS | 0.77/1.11 | 3.60/4.40 | — | — |
| HHHH | 0.3 | 0.75% ALS, 14.4% propylene glycol (PG), 10.0% SXS | >4.44/>4.44 | 4.58/>4.78 | — | — |
| IIII | 0.3 | 1.0% ALS, 10.0% PG, 10.0% SXS | >4.44/>4.44 | 4.48/>4.78 | — | — |
| JJJJ | 0.3 | 0.5% ALS, 20.0% PG, 10.0% SXS | >3.99/>3.99 | >4.45/>4.55 | 3.66/>4.04 | 3.23/3.28 |
| KKKK | 0.1 | 0.5% ALS, 20.0% PG, 10.0% SXS | >3.99/>3.99 | 3.75/>4.55 | 1.08/3.13 | 1.51/2.84 |
| LLLL | 0.0 | 0.5% ALS, 20.0% PG, 10.0% SXS | >3.99/>3.99 | 2.58/4.14 | 0.25/.072 | 1.28/2.36 |
| MMMM | 0.1 | 0.12% ALS, 20.0% PG, 10.0% SXS | >3.84/>3.84 | >4.41/>4.41 | 3.82/>3.92 | 3.95/>3.95 |
| NNNN | 0.3 | 0.5% ALS, 20.0% PG, 10.0% SXS | >3.84/>3.84 | >4.41/>4.41 | 3.56/>3.92 | 3.26/>3.95 |
| OOOO | 0.0 | 0.5% ALS, 20.0% PG, 10.0% SXS | 3.22/3.84 | 3.36/4.41 | 0.74/1.49 | 1.77/2.93 |
| PPPP | 0.3 | 0.8% SLS, 10.0% PG, 5.0% SXS | >4.11/>4.11 | 2.50/3.61 | — | — |
| QQQQ | 0.0 | 0.8% SLS, 10.0% PG, 5.0% SXS | 2.67/3.91 | 1.19/2.40 | — | — |
| RRRR | 0.3 | 0.8% SLS, 10.0% PG, 5.0% SXS | >4.11/>4.11 | 1.66/3.25 | — | — |
| SSSS | 0.0 | 0.8% SLS, 10.0% PG, 5.0% SXS | 2.28/3.03 | 0.79/1.63 | — | — |
| TTTT | 0.26 | 0.9% ALS, 10.0% PG, 5.0% SXS | >4.24/4.26 | 0.16/0.93 | -0.02/0.07 | 0.53/0.33 |
| UUUU | 0.0 | 0.9% ALS, 10.0% PG, 5.0% SXS | 2.53/>4.25 | 0.06/0.21 | 0.10/0.00 | 0.17/0.13 |

In addition to the observation that other solvents (e.g., PG and TPG) can be used in compositions of the present invention, products JJJJ through OOOO illustrate another effect of relative saturation of antibacterial agent in the system. The relative % saturation (highest to lowest) of the first three compositions is JJJJ>KKKK>LLLL. Composition of the present invention. Samples 13A through 13E show indications of phase separation very soon after dilution. Sample 13F phase separated after about 2 weeks. This observation is attributed to Sample 13F having a lower percent saturation of active ingredient than Samples 13A–13E.

Dilution Test Results

| Sample No. | Ingredients | Dilution (composition:water) | Results |
|---|---|---|---|
| 13A | 0.3 TCS/0.75 ALS/5 DPG/15 SXS | 50:50 | cloudy within 1 hr.; ppt formed within 1 day |
| 13B | 0.3 TCS/0.75 ALS/5 DPG/15 SXS | 75:25 | cloudy within 1 hr.; ppt formed within 1 day |
| 13C | 0.3 TCS/0.75 ALS/5 DPG/15 SXS | 25:75 | cloudy within 1 hr.; ppt tormed within 1 day |
| 13D | 1.0 TCS/2.5 ALS/0.75 CAPB/5 DPG/15 SXS | 50:50 | cloudy within 1 hr.; ppt formed within 1 day |
| 13E | 0.3 TCS/0.75 ALS/5 DPG/15 SXS | 50:50 | cloudy within 10 min.,; ppt formed within 30 min. |
| 13F | 0.2 TCS/0.75 ALS/2 DPG/15 SXS | 50:50 | clear, ppt formed in about 15 days |
| 13G | 0.3 TCS/1.35 ALS | 50:50 | clear, no ppt; unchanged after 23 days |
| 13H | 0.3 TCS/1.35 ALS | 75:25 | clear, no ppt; unchanged after 23 days |
| 13I | 0.3 TCS/1.35 ALS | 25:75 | clear, no ppt; unchanged after 22 days |
| 13J | 0.3 TCS/1.84 ALS | 50:50 | clear, no ppt; unchanged after 23 days |
| 13K | 0.3 TCS/1.84 ALS | 25:75 | clear, no ppt; unchanged after 22 days |
| 13L | 0.3 TCS/5.4 ALS/4.55 SLES-2/4 LDEA | 50:50 | clear, no ppt: unchanged after 15 days |
| 13M | Commercial Product A (PC) | 50:50 | clear, no ppt; unchanged after 15 days |
| 13N | Commercial Product B (SX) | 50:50 | clear, no ppt; unchanged after 15 days |
| 13O | Commercial Product C (LD) | 50:50 | clear, no ppt; unchanged after 15 days |

KKKK has one-third the amount of TCS as composition JJJJ solubilized in the same level of ALS (0.5%), and compositions LLLL contains 0% TCS. Significant reductions in activity were observed with respect to K. pneum. and S. choler. when the relative % saturation of TCS in the composition decreases. It also was observed that when the relative % saturation is essentially equal (i.e., about 100%), the activity remains essentially constant even though the absolute amount of TCS in the composition is decreased (i.e., compare Compositions MMMM to NNNN). These data further support the observations with respect to the importance of % saturation set forth in Example 6.

In addition, a comparison of composition IIII to composition TTTT shows that composition TTTT contains slightly less ALS (0.9% vs. 1.0% for TTTT), the same amount of PG (10.0%), and one-half the amount of SXS (5.0% vs. 10.0% for IIII). Experimental observations indicated that compositions IIII and TTTT were at or near 100% saturation. However, the log reductions of E. coli were considerably lower (about 4 log) for Composition TTTT. This observation further supports the data set forth in Example 7 wherein minimum level of hydrotrope may be needed for a high antibacterial efficacy against at least some Gram negative bacteria.

EXAMPLE 13

Dilution Tests

As described above, this test provides an indication of the ability of various compositions of the present invention to deposit topically active compounds on a test substrate. It also demonstrates that there is a fundamental difference between the dilution behavior of the present compositions and traditional compositions having solubilized actives. In the table below, Samples 13A through 13F are compositions Samples 13G through 13K are examples of active compound solubilized in surfactant alone (ALS). In those samples, the active compound does not phase separate from the composition upon dilution. These samples illustrate a fundamental difference in the present compositions versus surfactant-solubilized actives, i.e., although the TCS is nearly 100% saturated in Samples 13G–13I (0.3% TCS/1.35 ALS), no phase separation is observed upon dilution. Therefore, percent saturation of topically active compound is one factor in the deposition performance of the present compositions, but not the only factor. The unique ability of the present composition to phase separate upon dilution is also an important factor. Note also, Samples 13L–13O behave like solubilized active systems in that they do not phase separate on dilution.

EXAMPLE 14

Deposition Test Using Triclosan (TCS)

Examples of the present compositions were tested using the deposition test protocol described above. The mean deposition values were determined and subjected to statistical analysis (analysis of variance, ANOVA). As indicated in the table below, means with different letters have statistically significant differences at the 95% confidence limit. Note that four examples of the present composition (Samples 14A–14D) surprisingly have exceptional deposition enhancement over Commercial Product C, and substantial enhancements over Commercial Products A and B. Also note that although Sample 14B contains 0.3% TCS and Commercial Product C contains 0.2% TCS, the improved deposition enhancement (12.6 times greater for Example 14B) cannot be expected from the TCS content difference alone (i.e., only 1.5 times more TCS).

Deposition Test Results (TCS)

| Sample No. | Ingredients | Mean Deposition log$_{10}$ (gm/cm$^2$) | Relative Deposition |
|---|---|---|---|
| 14A | 1.0 TCS/2.5 ALS/0.75 CAPB/ 5 DPG/15 SXS | −4.21390a | 11.0 |
| 14B | 0.3 TCS/0.75 ALS/5 DPG/15 SXS | −4.15786a | 12.6 |
| 14C | 1.0 TCS/2.5 ALS/0.75 CAPB/ 5 DPG/15 SXS/0.3 Fragrance | −4.20673a | 11.2 |
| 14D | 0.6 TCS/1.5 ALS/0.75 CAPB/ 5 DPG/15 SXS | −4.37245b | 7.7 |
| Commercial Product A (PC) | 1% TCS | −4.45997b | 6.3 |
| Commercial Product B (SX) | 1% TCS | −4.62448c | 4.3 |
| Commercial Product C (LD) | 0.2% TCS | −5.25715d | 1.0 |

Note: Means with different letters (3rd column) are significantly different at 95%

EXAMPLE 15

Deposition Test Using Triclosan (TCS)

A second set of examples of the present compositions was tested using the deposition test protocol described above. The mean deposition values were determined and are presented as above. As in Example 14, samples based on the present compositions outperformed the traditional solubilized compositions. In this example, deposition enhancement was about fourteen times greater when compositions containing comparable amounts of TCS were compared (i.e., Example 15C vs. Example 15E, and Example 15D vs. Commercial Product C). In addition, this example illustrates the effect of percent saturation on deposition efficacy. It was observed that relative deposition decreases with decreasing relative % saturation. Comparative Sample 15E was a traditional, solubilized active composition having a base formulation very similar to Commercial Product C.

Deposition Test Results (TCS)

| Sample No. | Ingredients | Mean Deposition log$_{10}$ (gm/cm$^2$) | Relative % Saturation | Relative Deposition |
|---|---|---|---|---|
| 15A | 0.35 TCS/ 0.75 ALS/ 2 DPG/15 SXS | −3.98627a | ≈100 | 30.6 |
| 15B | 0.30 TCS/ 0.75 ALS/ 2 DPG/15 SXS | −4.07822b | 86 | 24.7 |
| 15C | 0.30 TCS/ 0.75 ALS/ 5 DPG/15 SXS | −4.11729b | — | 22.6 |
| 15D | 0.20 TCS/ 0.75 ALS/ 2 DPG/15 SXS | −4.33085c | 57 | 13.8 |
| 15E (Comparative) | 0.3 TCS/ 5.4 ALS/ 4.5 SLES-2/ 4 LDEA | −5.25315d | — | 1.7 |
| Commercial Product C (LD) | 0.2 TCS | −5.47155e | — | 1.0 |

Note: Means with different letters (3rd column) are significantly different at 95%

EXAMPLE 16

Deposition Test Using the Sunscreen Benzophenone-3 (BPh-3)

The present compositions also were tested for sunscreen deposition. The mean deposition values were determined and are presented as before. As in earlier examples, samples which are based on the present compositions (i.e., Samples 16A, 16B, and 16D–16F) outperformed the traditional, solubilized composition (Samples 16C and 16G).

Deposition Test Results (BPh-3)

| Sample No. | Ingredients | Mean Deposition log$_{10}$ (gm/cm$^2$) | Relative Deposition |
|---|---|---|---|
| 16A | 0.075 BPh-3/ 0.75 ALS/ 5 DPG/15 SXS | −5.03626a | 5.1 |
| 16B | 0.05 BPh-3/ 0.75 ALS/ 5 DPG/15 SXS | −5.17743b | 3.7 |
| 16C (Comparative) | 0.075 BPh-3/ 5.4 ALS/ 4.5 SLES-2/ 4 LDEA | −5.74745c | 1.0 |

Note: Means with different letters (3rd column) are significantly different ac 95%

EXAMPLE 16A

A Deposition Test Using the Sunscreen, Benzophenone-3 (BPh-3)

Deposition Test Results (BPh-3)

| Sample No. | Ingredients | Mean Deposition log$_{10}$ (gm/cm$^2$) | Relative Deposition |
|---|---|---|---|
| 16A | 0.75 BPh-3/ 0.75 ALS/ 5 DPG/15 SXS | −6.50234a | 1.5 |
| 16C (Comparative) | 0.075 BPh-3/ 5.4 ALS/ 4.5 SLES-2/ 4 LDEA | −6.71430b | 1.0 |
| 16D | 0.3 BPh-3/ 4.5 ALS/ 5 DPG/15 SXS | −4.83944a | 2.5 |

-continued

Deposition Test Results (BPh-3)

| Sample No. | Ingredients | Mean Deposition $\log_{10}$ (gm/cm$^2$) | Relative Deposition |
|---|---|---|---|
| 16E | 0.3 BPh-3/ 4.13 ALS/ 5 DPG/15 SXS | −4.88265a | 2.2 |
| 16F | 0.3 BPh-3/ 6.0 ALS/ 5 DPG/15 SXS | −4.88328a | 2.2 |
| 16G (Comparative) | 0.3 BPh-3/ 5.4 ALS/ 4.5 SLES-2/ 4 LDEA | −5.23377b | 1.0 |

Note: Means with different letters (3rd column) are significantly different at 95%

EXAMPLE 17

Deposition Test Using a Vitamin Derivative, Vitamin E Acetate (VitEOAc)

The present compositions also were tested using a vitamin derivative. The mean deposition values were determined and are presented as before, except the ANOVA test was not performed in this test. The values are approximate because the HPLC comparisons were estimated by hand analysis. Notwithstanding the approximations, the indications are clear that samples are based on the present compositions outperformed the traditional, solubilized compositions, i.e., Compare Example 17A to Example 17B, and Example 17C to Commercial Product D.

Deposition Test Results (VitEOAc)

| Sample No. | Ingredient | Estimated Relative Deposition |
|---|---|---|
| 17A | 0.15 VitEOAc/12 ALS/5 DPG/15 SXS | 24.5 |
| 17B (Comparative) | 0.15 VitEOAc/5.4 ALS/4.5 SLES-2/ 4 LDEA | 1.0 |
| 17C | 0.10 VitEOAc/12 ALS/5 DPG/15 SXS | 7.5 |

Deposition Test Results (VitEOAc)

| Sample No. | Ingredient | Estimated Relative Deposition |
|---|---|---|
| Commercial Product D (UMD) | 0.1% VitEOAc | 1.0 |

EXAMPLE 18

Deposition Test Using a Perfume Ingredient, Alpha-Hexylcinnamaldehyde (AHCALD)

The present compositions were also tested using a fragrance ingredient. The mean deposition values were determined and are presented as before. The sample based on the present compositions (Example 18A) outperformed a traditional, solubilized composition (Example 18B).

Deposition Test Results (ACHALD)

| Sample No. | Ingredient | Mean Deposition $\log_{10}$ (gm/cm$^2$) | Relative Deposition |
|---|---|---|---|
| 18A | 0.3 ACHALD/1.35 ALS/ 5 DPG/15 SXS | −4.79393b | 6.0 |
| 18B (Comparative) | 0.3 ACHALD/5.4 ALS/ 4.5 SLES-2/4 LDEA | −5.57478a | 1.0 |

Note: Means with different letters (3rd column) are significantly different at 95%

EXAMPLE 19

Deposition Test Using Triclosan (TCS) Solubilized in Solutions of Ammonium Lauryl Sulfate (ALS)

This examples shows the effect of percent saturation on the ability of the topically active ingredient to deposit on a surface. These results indicate, surprisingly, that for topically active compounds solubilized in surfactant solutions, the relative deposition increases with increasing percent saturation.

Deposition of TCS from Solutions of ALS

| % TCS | % ALS | Estimated % Saturation | Relative Deposition of TCS (%) | | | | | |
|---|---|---|---|---|---|---|---|---|
| | | | Run #1 | Run #2 | Run #3 | Run #4 | Run #5 | Run #6 |
| 0.3 | 1.35 | 100 | 100 | 100 | 100 | 100 | 100 | 100 |
| 0.3 | 2.00 | 68 | 95 | 98.5 | 62 | 57 | 61 | 59 |
| 0.3 | 2.50 | 54 | 95 | — | — | — | — | — |
| 0.3 | 5.00 | 27 | 88 | 82.3 | 47 | 38 | 43 | 40 |
| 0.3 | 10.00 | 14 | 65 | 55.4 | 27 | 32 | 25 | 28 |
| product dose size, g/mL H$_2$O | | | 0.02/3 | 0.03/3 | 0.3/2.7 | 3/neat | 0.3/2.7 | 0.3/2.7 |

EXAMPLE 20

Comparison of Pigskin vs. Volar Forearm Deposition Test Results

This example includes tests showing a comparison of the Pigskin Deposition Test to a Volar Forearm Deposition Test, and contains additional examples illustrating improved deposition performance of compositions of the present invention over traditional compositions. The volar forearm test validates the pigskin test. Further, the additional examples include a thickened composition that can be dispensed from ordinary packages as opposed to more expensive self-foaming pumps.

In particular, a composition of the present invention, i.e., Sample 20A, containing 0.975TCS/15SXS/5DPG/2.5ALS/0.75CAPB/0.20 Fragrance plus a pH buffer and colorants, was tested on human forearms. In a separate test, a commercially available hand wash product containing 0.18% TCS was tested. The test results for these tests are illustrated in the table below.

Volar Forearm Deposition Results

| Site | Commercial Product (0.18% TCS) TCS Deposition (g/cm$^2$) | Sample 20A (0.975% TCS) TCS Deposition (g/cm$^2$) |
| --- | --- | --- |
| JLF-L1 | 4.12E-7 | 1.48E-5 |
| JLF-R1 | 4.76E-7 | 1.29E-5 |
| EPS-L1 | 3.93E-7 | 1.32E-5 |
| EPS-R1 | 3.93E-7 | 1.26E-5 |
| PSF-L1 | 1.19E-7 | — |
| PSF-R1 | 2.88E-7 | — |
| JLF-L2 | 4.68E-7 | 1.82E-5 |
| JLF-R2 | 7.36E-7 | 1.94E-5 |
| EPS-L2 | 7.36E-7 | 1.82E-5 |
| PSF-L2 | 1.42E-7 | — |
| PSF-R2 | 2.29E-7 | — |
| Average | 3.97E-7 | 1.55E-5 |

For comparison, the samples used in the Volar Forearm Deposition Test were tested using the Pigskin Deposition Test, together with two additional compositions of the present invention, i.e.:

Sample 20B (a thickened composition containing 1.0TCS/15.0SXS/5.0DPG/2.5ALS/0.75CAPB/0.8 Natrosol 250 HHR Cs (hydroxyethylcellulose polymer)/0.20 Fragrance (plus a pH buffer and colorants); and Sample No. 20C (a composition containing additional skin care ingredients, i.e., 0.46TCS/15.0SXS/5.0DPG/2.97 glycerin/1.0 sodium PCA/0.75ALS/0.75CAPB/0.25 Polyquaternium-10/0.1 Cetyl Alcohol/0.1 Aloe Barbadensis/(plus fragrance, a pH buffer, preservatives and colorants).

Pigskin TCS Deposition Results

| Sample No. | Relative Deposition | Relative Deposition Adjusted for TCS Content | TCS Deposition (g/cm$^2$) | TCS Deposition from Volar Forearm Test (g/cm$^2$) |
| --- | --- | --- | --- | --- |
| 20A (0.97% TCS/invention) | 17.0 | 3.06 | 1.99E-5 | 1.55E-5 |
| 20C (0.46% TCS/invention) | 9.7 | 3.80 | 1.15E-5 | — |
| 20B (1.0% TCS/invention) | 18.6 | 3.35 | 2.18E-5 | — |
| Commercial product (0.18% TCS) | 1.0 | 1.0 | 1.17E-6 | 3.97E-7 |

The deposition results for Sample 20A in the pigskin test compared favorably with the data from the in vivo test. However, the pigskin results showed a somewhat higher deposition of the commercial product than the in vivo test. This has been attributed to an extraction technique for the pigskin test that may be more aggressive than in the in vivo test. Further, lower amounts of topically active compound may be more difficult to extract completely from a surface (i.e., binding "sites" are overwhelmed where more active compound is on the surface). As such, retrieval of most of the sample from a high deposition formula like Sample 20A is expected, whereas complete recovery of the active compound from a low depositing formula, like the commercial product, is not expected, especially if the extraction technique for the in vivo test is less aggressive. The pigskin deposition test, therefore, has been demonstrated as an effective screening model for deposition performance on human skin.

In addition, it should be noted that all of the three examples of the invention composition deposited the active ingredient in an amount at least three times greater than the commercial product.

The data presented in the above tables show that % saturation of a topically effective compound in a present composition can be directly correlated to a log reduction of bacteria, i.e., to efficacy. For example, as shown in the prior tables, a composition having 50% saturation of TCS in the aqueous phase demonstrates a log reduction versus *S. aureus* of 1.96 (30 seconds) and 3.05 (60 seconds) and a log reduction versus *E. coli* of 2.45 (30 seconds) and greater than 3.81 (60 seconds). A 75% saturated and a 100% saturated composition exhibited a log reduction of greater than 4.55 (30 and 60 seconds) vs. *S. aureus* (i.e., a log reduction in excess of the detection limit of the assay). The 75% and 100% saturated compositions exhibited a log reduction of 3.40 (30 seconds) and greater than 3.81 (60 seconds) and greater than 3.81 (30 and 60 seconds) vs. *E. coli*, respectively. Accordingly, the present antibacterial compositions can be characterized as exhibiting a log reduction of at least about 2 (after 30 seconds) or at least about 3 (after 60 seconds) vs. *S. aureus*, or of at least about 2.5 (after 30 seconds) or at least about 3.5 (after 60 seconds) vs. *E. coli*.

In addition, the compositions have an enhanced ability to deposit the topically active compound on a treated surface, thereby providing an effective residual activity. Prior compositions did not have an ability to effectively deposit the topically active compound, and the topically active compound was removed during the rinsing step, and wasted. The present compositions, therefore, have a dual benefit of a rapid, effective topical effect, and an excellent residual effect.

The topically active compositions of the present invention have several practical end uses, including hand cleansers, mouthwashes, surgical scrubs, body splashes, hand sanitizer gels, hair care products, topical medicaments, skin care products, and similar personal care products. Additional types of compositions include foamed compositions, such as creams, mousses, and the like, and compositions containing organic and inorganic filler materials, such as emulsions, lotions, creams, pastes, and the like. The compositions further can be used as an antibacterial cleanser for hard surfaces, for example, sinks and countertops in hospitals, food service areas, and meat processing plants. The present antibacterial compositions can be manufactured as dilute ready-to-use compositions, or as concentrates that are diluted prior to use.

The compositions also can be incorporated into a web material to provide an antibacterial wiping article. The wiping article can be used to clean and sanitize skin or inanimate surfaces.

The present compositions provide the advantages of a broad spectrum kill of Gram positive and Gram negative bacteria in short contact times. The short contact time for a substantial log reduction of bacteria is important in view of the typical 15 to 60 second time frame used to cleanse and sanitize the skin and inanimate surfaces. The compositions also effectively deposit the topically active compound for a strong residual topical effect.

The present compositions are effective in short contact time because the topically active compound is present in the aqueous continuous phase of the composition, as opposed to surfactant micelles. The active compound, therefore, is available to immediately begin providing a topical effect, and further effectively deposits on the skin, hair, or other surface to provide residual topical efficacy. In addition, because the topically effective compound is in solution as opposed to surfactant micelles, the absolute amount of topically effective compound in the composition can be reduced without adversely affecting efficacy, and the topically active compound is not rinsed from the skin with the surfactant prior to performing its antibacterial function. The topically active compound also is effectively deposited on the skin to provide an excellent residual effect. In addition, the amount of surfactant in the present topically active compositions typically is low, thereby providing additional environmental benefits.

The following examples illustrate various compositions of the present invention.

EXAMPLE 21

Hand Wash Composition

A composition in accordance with the instant invention, suitable for use as a hand wash, was prepared. The composition contained the following components in the indicated weight percentages:

| Ingredient | Weight Percent |
|---|---|
| Triclosan | 0.3 |
| Ammonium Lauryl Sulfate | 0.75 |
| Dipropylene Glycol | 5.0 |
| Sodium Xylene Sulfonate | 10.0 |
| Fragrance | 0.05 |
| Water | q.s. |

The composition was prepared by admixing the dipropylene glycol, TCS, and fragrance until homogeneous (about 5 minutes). After the triclosan was completely dissolved, as evidenced by the absence of undissolved solid material, the sodium xylene sulfonate was added to the solution. The resulting mixture then was stirred to completely dissolve the sodium xylene sulfonate (about 5 minutes). Finally, the ammonium lauryl sulfate and water were added to the resulting solution, and the composition was stirred until homogeneous (about 5 minutes).

The composition had a weight ratio of surfactant:triclosan of 2.5:1, and was at least about 90% saturated with triclosan. The composition was evaluated for antibacterial efficacy against *S. aureus* and *E. coli* using a time kill test. Against *S. aureus*, the composition exhibited a log reduction of >4.07 in 30 seconds, while against *E. coli* the composition exhibited a log reduction of 3.90 in 30 seconds. Thus, the composition exhibited an excellent broad spectrum antibacterial activity. Also, the composition was an excellent hand wash composition in an actual use test, providing both good cleansing and a smooth feel to the hands.

EXAMPLE 22

Body Splash Composition

A composition in accordance with the present invention, suitable for use as a body splash, is prepared using the following ingredients in the following weight percentages:

| Ingredient | Weight Percent |
|---|---|
| Triclosan | 0.3 |
| Alkyl Polyglycoside | 0.3 |
| Propylene Glycol | 14.4 |
| Sodium Xylene Sulfonate | 10.0 |
| Ethanol | 10.0 |
| Fragrance | 0.05 |
| Water | q.s. |

The composition is prepared by combining the triclosan, propylene glycol, fragrance, and ethanol, and admixing the components until all the triclosan is dissolved, as evidenced by the absence of undissolved solid material. The sodium xylene sulfonate then is added, and the resulting mixture is stirred until the sodium xylene sulfonate is completely dissolved. Finally, the alkyl polyglycoside and water are added, and the mixture again is stirred until homogeneous. The resulting composition forms an excellent and refreshing body splash that provides a desirable level of bacterial reduction on the skin of the user.

EXAMPLE 23

Mouthwash Composition

A composition in accordance with the present invention, suitable for use as a mouthwash, is prepared using the following ingredients in the following weight percentages:

| Ingredient | Weight Percent |
|---|---|
| Triclosan | 0.3 |
| Alkyl Polyglycoside | 0.3 |
| Propylene Glycol | 14.4 |
| Sodium Xylene Sulfonate | 10.0 |
| Denatured Alcohol | 10.0 |
| Oil of Wintergreen (flavor) | 0.05 |
| Water | q.s. |

The composition is prepared by combining the triclosan, propylene glycol, flavor, and denatured alcohol, and admixing the components by any conventional means until all the triclosan is dissolved, as evidenced by the absence of undissolved solid material. Then, the sodium xylene sulfonate is added, and the resulting mixture is stirred until the sodium xylene sulfonate is completely dissolved. Finally, the alkyl polyglycoside and water are added, and the mixture again is stirred until homogeneous. The resulting composition forms an excellent and refreshing mouthwash that provides a desirable level of bacterial reduction on the teeth, gums, and tongue of the user.

EXAMPLE 24

Wet Wipe Composition

A composition in accordance with the present invention, suitable for impregnating a nonwoven material for the preparation of a wet wipe article, was prepared using the following ingredients in the following weight percentages:

| Ingredient | Weight Percent |
| --- | --- |
| Triclosan | 0.3 |
| Ammonium Lauryl Sulfate | 0.75 |
| Dipropylene Glycol | 5.0 |
| Sodium Xylene Sulfonate | 15.0 |
| Water | q.s. |

The composition was prepared by combining the triclosan and dipropylene glycol, and admixing the components until all the triclosan was dissolved, as evidenced by the absence of undissolved solid material. The sodium xylene sulfonate then was added, and the resulting mixture was stirred until the sodium xylene sulfonate was completely dissolved. Finally, the ammonium lauryl sulfate and water were added, and the mixture was again stirred until homogeneous.

A piece of nonwoven cellulosic web material (i.e., a commercial paper towel) then was dipped by hand into the composition to form a wet wipe article, suitable for wiping and cleaning surfaces, for example, hands. The article formed an excellent wet wipe and the impregnated antibacterial composition was freely expressed from the web to provide a broad spectrum antibacterial activity.

EXAMPLE 25

Hand Wash Composition

A composition in accordance with the present invention, suitable for use as a hand wash, was prepared. The composition comprised the following components at the indicated weight percentages:

| Ingredient | Weight Percent |
| --- | --- |
| Triclosan | 0.3 |
| Ammonium Lauryl Sulfate | 0.75 |
| Dipropylene Glycol | 5.0 |
| Sodium Xylene Sulfonate | 15.0 |
| Water | q.s. |

The composition was prepared by first admixing the triclosan and dipropylene glycol until homogeneous (about 5 minutes). After the triclosan was completely dissolved, as evidenced by the absence of undissolved solid material, the sodium xylene sulfonate was added to the solution. The mixture then was stirred to completely dissolve the sodium xylene sulfonate (about 5 minutes). Finally, the ammonium lauryl sulfate and water were added to the resulting solution, and the composition was stirred until homogeneous (about 5 minutes).

The composition had a weight ratio of surfactant:triclosan of 2.5:1 and was at least about 90% saturated with triclosan. The composition was evaluated for its antibacterial efficacy against $S.$ aureus, $E.$ coli, $K.$ pneum., and $S.$ choler. using a time kill test, and a contact time of 30 seconds. The composition exhibited log reductions of >3.59, >4.49, >3.20, and >4.27 against the four test organisms, respectively.

Thus, the composition exhibited an excellent broad spectrum antibacterial activity. In addition, the composition was an excellent hand wash composition in an actual use test, providing both good cleansing and a smooth feel to the hands.

EXAMPLE 26

Comparison to a Previously Disclosed Composition

This example compares the antibacterial efficacy of a composition of the present invention to a previously disclosed composition. Accordingly, the composition of Example 18 was compared to the sole example disclosed in WO98/01110. In both compositions, the active antibacterial agent was triclosan (TCS). Both compositions were evaluated for antibacterial efficacy in a time kill test against $S.$ aureus, $E.$ coli, $K.$ pneum., and $S.$ choler. The example of WO98/01110 was tested at 50% dilution, in accordance with the test procedure for viscous compositions. The following data summarizes the percent of active antibacterial agent in each composition at the test dilution (i.e., test dilution is 100% for the composition of Example 18 and 50% for the example of WO98/01110), and the log reduction observed in the time kill test at a contact time of 30 seconds.

| Composition | % TCS | Log Reduction at 30 seconds | | | |
| --- | --- | --- | --- | --- | --- |
| | | S. aureus | E. coli | K. pneum. | S. choler. |
| Example 25 | 0.3 | >4.60 | >4.50 | 4.21 | >4.68 |
| WO 98/01110 | 0.5 | 3.29 | 0.29 | 1.00 | 0.45 |

This example demonstrates the superior time kill performance of a composition of the present invention compared to a prior composition, especially against Gram negative bacteria. This superiority is demonstrated even through the comparative composition contained substantially more active antibacterial agent compared to the inventive composition. Thus, an inventive composition utilizes the active agent more efficiently, as illustrated in a higher log reduction using a reduced concentration of antibacterial agent.

EXAMPLE 27

Comparison to a Previously Disclosed Composition

This example compares the antibacterial efficacy of a composition of the present invention to a previously disclosed composition. Accordingly, the composition of Example 25 was compared to a composition disclosed in WO96/06152. WO96/06152 discloses effective compositions comprising TCS, an anionic surfactant, a hydrotrope; a hydric solvent, and further comprising an organic acid, specifically citric acid. WO96/06152 contains additional pH adjusting agents, such as monoethanolamine and sodium hydroxide. Further, the examples disclosed in WO96/06152 all have a pH of 4 or 9.1, with no examples having a desirable, neutral pH of about 7. A pH of about 7 is desired for compositions contacting skin or inanimate surfaces because compositions of pH substantially different from 7, such as 4 or 9.1, have a greater potential to damage the surfaces they contact. Accordingly, the composition of Example 1 of WO96/06152 (hereafter referred to as composition 27-A) was prepared. For comparison, composition 27-A was prepared as above, except that the pH was adjusted to 7 by the addition of further monoethanolamine (this composition hereafter referred to as composition 27-B). To provide an additional comparison, the composition of Example 3 of WO96/06152 was prepared, except that it was prepared at a pH of 7 by the addition of further monoethanolamine (this composition is hereafter referred to as composition 27-C). The table below summarizes the results of a time kill test on the compositions of this example against the bacteria indicated at a contact time of 30 seconds.

| Composition | pH | % TCS | Log Reduction at 30 seconds | | | |
|---|---|---|---|---|---|---|
| | | | S. aureus | E. coli | K. pneum. | S. choler. |
| Example 25 | 7.1 | 0.3 | >4.54 | >4.25 | 3.67 | >4.77 |
| Comparative 27-A | 4 | 0.075 | — | — | >4.84 | — |
| Comparative 27-B | 7 | 0.075 | — | — | 0.07 | — |
| Comparative 27-C | 7 | 0.15 | 4.44 | 2.91 | 0.28 | 4.67 |

This example demonstrates the superior time kill performance of a composition of the present invention compared to prior compositions, especially with respect to Gram negative bacteria at a pH of about 7. From the data presented in this example, it can be concluded that the compositions of WO96/06152 rely substantially on a relatively extreme pH (either 4 or 9, as disclosed) to achieve a desirable, rapid and broad spectrum reduction of bacterial populations. This is in contrast to Example 18 of the present invention, which provides a rapid broad spectrum bacteria kill at the desirable pH of about 7.

EXAMPLE 28

Antibacterial Composition Containing PCMX

An antibacterial composition in accordance with the present invention containing p-chloro-m-xylenol (PCMX) as the active antibacterial agent was prepared. The composition contained the following components in the indicated weight percentages:

| Ingredient | Weight Percent |
|---|---|
| PCMX | 0.1 |
| Ethanol | 13.42 |
| Water | q.s. |

The composition was prepared by first mixing the PCMX and ethanol to completely solubilize the PCMX (about 5 minutes). After the PCMX was completely dissolved, as evidenced by the absence of undissolved solid material, the water was added, and the composition was stirred until homogeneous (about 5 minutes).

The composition was at least about 90% saturated with PCMX. The composition was evaluated for antibacterial efficacy against S. aureus, E. coli, K. pneum., and S. choler. using a time kill test. Against S. aureus, the composition exhibited a log reduction of 4.16 in 30 seconds; against E. coli the composition exhibited a log reduction of >4.34 in 30 seconds; against K. pneum. the composition exhibited a log reduction of 3.99 in 30 seconds; and against S. choler. the composition exhibited a log reduction of >4.04 in 30 seconds. Thus, the composition exhibited an excellent broad spectrum antibacterial activity.

EXAMPLE 29

Antibacterial Composition Containing PCMX

A composition in accordance with the present invention incorporating p-chloro-m-xylene as the active antibacterial ingredient was prepared. The composition contained the following components in the indicated weight percentages:

| Ingredient | Weight Percent |
|---|---|
| PCMX | 0.3 |
| Ammonium Lauryl Sulfate | 0.8 |
| Water | q.s. |

The composition was prepared by first combining the PCMX and water, then adding the ammonium lauryl sulfate and mixing the components for such time as to completely admix the components and dissolve the PCMX (about 2 hours).

The composition was at least about 90% saturated with PCMX. The composition was evaluated for its antibacterial efficacy against S. aureus and E. coli using a time kill test. Against S. aureus, the composition exhibited a log reduction of >3.57 in 30 seconds; and against E. coli the composition exhibited a log reduction of >4.17 in 30 seconds. Thus, the composition exhibited an excellent broad spectrum antibacterial activity.

Obviously, many modifications and variations of the invention as hereinbefore set forth can be made without departing from the spirit and scope thereof, and, therefore, only such limitations should be imposed as are indicated by the appended claims.

APPENDIX A

| Fragrance Compounds | | |
|---|---|---|
| Acetyl Hexamethyl Tetralin | Balm Mint Extract | Benzyl Cinnamate |
| | Balm Mint Oil | Benzyl Salicylate |
| Amyl Acetate | Bay Oil | Bitter Almond |
| Amyl Salicylate | Benzaldehyde | Calendula Oil |
| Anethole | Benzyl Acetate | Camellia Oil |
| Anise Oil | Benzyl Alcohol | Camphor |
| Annatto | Benzyl Benzoate | Caraway Oil |
| Cardamom Oil | Juniper Tar | Pentadecalactone |
| Carvone | Lavender Oil | Peppermint Extract |
| Chamomile Oil | Lemongrass Oil | Peppermint Oil |
| | Lemon Oil | Phenethyl Alcohol |
| Cinnamin Oil | Lovage Oil | Pine Oil |
| Citral | Matricaria Oil | Pine Tar Oil |
| Cloveleaf Oil | Menthol | Rose Extract |
| Clove Oil | Menthyl Acetate | Rosemary Oil |
| Conander Oil | Menthyl Lactate | Rose Oil |
| Coumarin | Menthyl Salicylate | Rue Oil |
| Cumin Extract | Methyldihydrojasmonate | Sage Oil |

APPENDIX A-continued

Fragrance Compounds

| | | |
|---|---|---|
| p-Cymene | Methyl Eugenol | Sambucus Extract |
| Dimethyl Brassylate | Methyl Rosinate | Sambucus Oil |
| Dipentene | Nutmeg Oil | Sandalwood Oil |
| Ethylene Brassylate | Ocotea Cymbarum Oil | Sassafras Oil |
| Ethyl Vanillin | Olibanum | Sweet Marjoram Oil |
| Eucalyptol | Olibanum Extract | Tar Oil |
| Eucalytus Oil | Orange Extract | Tea Tree Oil |

APPENDIX A-continued

Fragrance Compounds

| | | |
|---|---|---|
| Eugenol | Orange Flower Oil | Terpineol |
| | Orange Flower Water | Thyme Oil |
| Ginger Oil | Orange Oil | Thymol |
| Gum Benzoin | Orange Peel Extract | Vanilla |
| Hops Oil | Orns Root Extract | Vanillin |
| Isoamyl Acetate | Parsley Seed Oil | Yarrow Oil |

APPENDIX B

Hair Conditioning Agents

| | | |
|---|---|---|
| | Allantoin Acetyl Methionine | Methionine |
| | Ammonium Hydrolyzed Animal Protein | Methyl Hydroxymethyl Oleyl Oxazoline |
| Acetylated Lanolin | Hydroxyethyl Stearamide-MIPA | Mineral Oil |
| Acetylated Lanolin Alcohol | Hydroxylated Lanolin | Mink Oil |
| Acetylated Lanolin Ricinoleate | Hydroxyphenyl Glycinamide | Mink Wax |
| Dihydroxyethyl Oleyl Glycinante | | |
| Dihydroxyethyl Soya Glycinante | | |
| Dihydroxyethyl Soyamine Dioleate | | Montan Acid Wax |
| | Isobutylated Lanolin Oil | Montan Wax |
| Dihydroxyethyl Stearyl Glycinante | Isodecyl Isononanoate | |
| Dihydroxyethyl Tallowamine Oleate | Capryloyl Hydrolyzed Animal Keratin | |
| Amodimethicone | Isononyl Isononanoate | |
| Dihydroxyethyl Tallow Glycinante | Isopropyl Lanolate | |
| Dimethicone Copolyol | Isopropyl Myristate | |
| Dimethyl Lauramine Oleate | Isopropyl Palmitate | Myristaminopropionic Acid |
| Disodium Caproamphodiacetate | Aspartic Acid | Myristoyl Hydrolyzed Animal Protein |
| Disodium Caproamphodipropionate | Avocado Oil | Myristoyl Sarcosine |
| Disodium Capryloamphodiacetate | Avocado Oil Unsaponifiables | Niacin |
| Disodium Capryloamphodipropionate | Balsam Canada | Niacinamide |
| Disodium Cocoamphodiacetate | Balsam Oregon | Nonfat Dry Milk |
| Disodium Cocoamphodipropionate | Balsam Peru | Norvaline |
| | | Carnauba |
| | | Casein |
| Disodium Isostearoamphodipropionate | | Ceresin |
| Disodium Lauroamphodiacetate | | Coal Tar |
| Disodium Lauroamphodipropionate | Isostearoyl Hyrolyzed Animal Protein | |
| Disodium Oleamido MIPA-Sulfosuccinate | Japan Wax | Oleamidopropyl Dimethylamine Hydrolyzed |
| Disodium Oleoamphodipropionate | Jojoba Butter | Animal Protein |
| Disodium Stearoamphodiacatate | Jojoba Oil | |
| | Jojoba Wax | |
| Dried Egg Yolk | Juniper Tar | |
| Egg | Keratin | Oleoyl Hydrolyzed Animal Protein |
| Egg Powder | Lanolin | |
| Egg Yolk | Lanolin Alcohol | |
| Ethyl Ester of Hydrolyzed Animal Protein | | Oleyl Lanolate |
| Ethyl Glutamate | Lanolin Linoleate | Olive Oil |
| | Lanolin Oil | Olive Oil Unsaponifiables |
| Ethyl Morrhuate | Lanolin Ricinoleate | Ouncury Wax |
| Ethyl Serinate | Lanolin Wax | Balsam Tolu |
| | Colloidal Sulfur | Bayberry Wax |
| Glutamic Acid | Corn Oil | |
| | Cyclomethicone | C12–16 Alcohols |
| Glyceral Distearate | | Calcium Pantothenate Oxide |
| Glyceral Lanolate | | Candelilla Wax |
| Glyceral Trioctanoate | | |
| Glyceral Triundecanoate | Lauraminopropionic Acid | Palmitoyl Animal Collagen Amino Acids |
| Glycine | Lauroampodipropionic Acid | Palmitoyl Hydrolyzed Animal Protein |
| Glycol Oleate | Lauroyl Hydrolyzed Animal Protein | Palmitoyl Hydrolyzed Milk Protein |
| Glycol Ricinoleate | Dicapryloyl Cystine | Palm Kernelamide DEA |
| Henna Extract | Diethylaminoethyl PEG-5 Laurate | Palm Kernelamide MEA |
| Hinokitiol | Diethylene Tricaseinamide | Palm Kernelamide MIPA |
| Histidine | | Panthenol |
| Hybrid Safflower Oil | Lauryl Glycol | Panthenyl Ethyl Ether |
| Hydrogenated Jojoba Wax | Lauryl Mynstate | Panthenyl Ethyl Ether Acetate |
| Hydrogenated Lanolin | Lauryl Palmitate | Pantothenic Acid |
| Hydrogenated Rice Bran Wax | Cocaminobutyric Acid | |
| | Cocaminopropionic Acid | |
| Hydrolyzed Animal Elastin | Cocoamphodipropionic Acid | PEG-5 Hydrogenated Lanolin |
| Hydrolyzed Animal Keratin | Coco-Hydrolyzed Animal Protein | PEG-10 Hydrogenated Lanolin |
| Hydrolyzed Animal Protein | | PEG-20 Hydrogenated Lanolin |

APPENDIX B-continued

Hair Conditioning Agents

| | | |
|---|---|---|
| Hydrolyzed Casein | | PEG-24 Hydrogenated Lanolin |
| Hydrolyzed Human Placental Protein | Linoleic Acid | PEG-30 Hydrogenated Lanolin |
| Hydrolyzed Silk | Linolenic Acid | PEG-70 Hydrogenated Lanolin |
| Hydrolyzed Soy Protein | Linseed Oil | Animal Collagen Amino Acids |
| Hydrolyzed Vegetable Protein | Coconut Oil | Animal Elastin Amino Acids |
| Hydrolyzed Yeast | | Animal Keratin Amino Acids |
| Hydrolyzed Yeast Protein | Methicone | |
| Petrolatum | | Soluble Animal Collagen |
| Phenylalanine | | |
| Phenyl Trimethicone | | Soybean Oil |
| PPG-2-Buteth-3 | | Soybean Oil Unsaponifiables |
| PPG-3-Buteth-5 | | Squalane |
| PPG-5-Buteth-7 | | Squalene |
| PPG-7-Buteth-10 | | Stearlyl Alcohol |
| PPG-9-Buteth-12 | | Sulfur |
| PPG-12-Buteth-16 | | Sweet Almond Oil |
| PPG-15-Buteth-20 | | Synthetic Wax |
| PPG-20-Buteth-30 | | Threonine |
| PPG-24-Buteth-27 | | Tripaba Panthenol |
| PPG-26-Buteth-26 | | |
| PPG-28-Buteth-35 | | |
| PPG-33-Buteth-45 | | |
| PPG-4 Butyl Ether | | |
| PPG-5 Butyl Ether | | |
| PPG-9 Butyl Ether | | |
| PPG-14 Butyl Ether | | Vegatable Oil |
| PPG-15 Butyl Ether | | Wheat Germanidopropylamine Oxide |
| PPG-16 Butyl Ether | | Wheat Germ Oil |
| PPG-18 Butyl Ether | | Zein |
| PPG-22 Butyl Ether | | Zinc Hydrolyzed Animal Protein |
| PPG-30 Butyl Ether | | |
| PPG-33 Butyl Ether | | |
| PPG-40 Butyl Ether | | |
| PPG-53 Butyl Ether | | |
| Pyridoxine Dicaprylate | | |
| Pyridoxine Dilaurate | | |
| Pyridoxine Dioctenoate | | |
| Pyridoxine Dipalmitate | | |
| Pyridoxine Tripalmitate | | |
| Resorcinol Acetate | | |
| Rice Bran Wax | | |
| Safflower Oil | | |
| Salicylic Acid | | |
| Serine | | |
| Sesame Oil | | |
| Shea Butter Unsaponifiables | | |
| Shellac Wax | | |
| Silk | | |

APPENDIX C

Ultraviolet Light Absorbers

| | | |
|---|---|---|
| Allantoin PABA | Benzyl Salicylate | Isoamyl p-Methoxycinnamate |
| Amsonic Acid | Bornelone | Isobutyl PABA |
| Benzophenone-1 | Bumetrizole | Isopropylbenzylsalicylate |
| Benzophenone-2 | Butyl Methoxydibenzoylmethane | Isopropyl Methoxycinnamate |
| Benzophenone-3 | Butyl PABA | Menthyl Anthranilate |
| Benzophenone-4 | Cinoxate | Menthyl Salicylate |
| Benzophenone-5 | | Octocrylene |
| Benzophenone-6 | Digalloyl Trioleate | Octrizole |
| Benzophenone-7 | Drometrizole | Octyl Dimethyl PABA |
| Benzophenone-8 | Ethyl Dihydroxypropyl PABA | Octyl Methoxycinnamate |
| Benzophenone-9 | Ethyl Diisopropylcinnamate | Octyl Salicylate |
| Benzophenone-10 | Etocrylene | PABA |
| Benzophenone-11 | Glyceryl PABA | |
| Benzophenone-12 | Glycol Salicylate | Tripaba Panthenol |
| 3-Benzylidene Camphor | Homosalate | |

Skin Care Agents

| | | |
|---|---|---|
| Acetyl Trioctyl Citrate | Dihydrophytosteryl Octyldecanoate | Hydrogenated Lard Glyceride |
| Apricot Kernel Oil PEG-6 Esters | Dihydroxyethyl Soyamine Dioleate | Hydrogenated Lard Glycerides |
| Arachidyl Propionate | Dihydroxyethyl Tallowamine Oleate | Hydrogenated Palm Glycerides |
| Avocado Oil | Diisobutyl Adipate | Hydrogenated Palm Kernel Glycerides |

APPENDIX C-continued

Bay Oil
Behenyl Erucate
Bisphenylhexamethicone
Butyl Acetyl Ricinoleate
Butyl Myristate
Butyl Oleate
Butyl Stearate
C18–36 Acid Glycol Ester
C12–15 Alcohols Benzoate
C12–15 Alcohols Lactate
C12–15 Alcohols Octonoate
C14–15 Alcohols
C15–18 Glycol
C18–20 Glycol Isostearate
C14–16 Glycol Palmitate
C13–14 Isoparaffin
C13–16 Isoparaffin
C20–40 Isoparaffin
C11–15 Pareth-3 Oleate
C11–15 Pareth-3 Stearate
C11–15 Pareth-12 Stearate
C12–15 Pareth-9 Hydrogenated Tallowate
C12–15 Pareth-12 Oleate
C30–46 Piscine Oil
Caprylic/Capric/Diglyceryl Succinate
Caprylic/Capric Glycerides
Caprylic/Capric/Isostearic/Adipic Triglycerides
Cetearyl Alcohol
Cetearyl Isononanoate
Cetearyl Octanoate
Cetearyl Palmitate
Cetyl Acetate
Cetyl Alcohol
Cetylarachidol
Cetyl Esters
Cetyl Lactate
Cetyl Myristate
Cetyl Octanoate
Cetyl Palmitate
Cetyl Ricinoleate
Cetyl Stearate
Coco-Caprylate/Caprate
Cocoglycerides
Coconut Alcohol
Corn Oil PEG-06 Esters
Cottonseed Glyceride
Cottonseed Oil
Cyclomethicone
Decyl Alcohol
Decyl Isostearate
Decyl Oleate
Decyl Succinate
Decyltetradecanol
Dibutyl Adipate
Dibutyl Sebacate
Di-C12–15 Alcohols Adipate
Dicapryl Adipate
Dicetyl Adipate
Diethylene Glycol Dibenzoate
Diethyl Palmitoyl Aspartate
Diethyl Sebacate
Dihexyl Adipate
Dihydrocholesteryl Octyldecanoate
Laureth-2 Benzoate
Lauryl Alcohol
Lauryl Glycol
Lauryl Isostearate
Lauryl Lactate
Lauryl Myristate
Lauryl Palmitate
Methyl Acetyl Ricinoleate
Methyl Caproate
Methyl Caprylate
Methyl Caprylate/Caprate
Methyl Cocoate
Methyl Dehydroabietate
Methyl Glucose Sesquioleate
Methyl Glucose Sesquistearate
Methyl Hydrogenated Rosinated Diisocetyl Adipate
Diisodecyl Adipate
Diisopropyl Adipate
Diisopropyl Dilinoleate
Diisopropyl Sebacate
Diisostearyl Adipate
Diisostearyl Dilinoleate
Diisostearyl Malate
Dilauryl Citrate
Dimethicone Copolyol
Dimethiconol
Dioctyl Adipate
Dioctyl Dilinoleate
Dioctyl Sebacate
Dioctyl Succinate
Dipropylene Glycol Dibenzoate
Ditridecyl Adipate
Dodecyltetradecanol
Ethyl Arachidonate
Ethyl Laurate
Ethyl Linoleate
Ethyl Linolenate
Ethyl Monhuate
Ethyl Mynstate
Ethyl Palmitate
Ethyl Pelargonate
Ethyl Persate
Ethyl Stearate
Fish Glycerides
Glyceryl Behenate
Glyceryl Caprate
Glyceryl Caprylate
Glyceryl Caprylate/Caprate
Glyceryl Cocoate
Glyceryl Dilaurate
Glyceryl Dioleate
Glyceryl Distearate
Glyceryl Erucate
Glyceryl Hydroxystearate
Glyceryl Isostearate
Glyceryl Lanolate
Glyceryl Laurate
Glyceryl Linoleate
Glyceryl Myristate
Glyceryl Oleate
Glyceryl Palmitate
Glyceryl Ricinoleate
Glyceryl Sesquioleate
Glyceryl Stearate
Glyceryl Stearate Citrate
Glyceryl Stearate Lactate
Glyceryl Triacetyl Hydroxystearate
Glyceryl Triacetyl Ricinoleate
Glyceryl Trioctanoate
Glyceryl Triundecanoate
Glyceryl Dioctanoate
Glycol Hydroxystearate
Glycol Oleate
Glycol Ricinoleate
Glycol Stearate
Heptylundecanol
Hexyl Laurate
Hydrogenated Coco-Glycerides
Octyl Myristate
Octyl Palmitate
Octyl Pelargonate
Octyl Stearate
Oleyl Acetate
Oleyl Alcohol
Oleyl Arachidate
Oleyl Erucate
Oleyl Lanolate
Oleyl Myristate
Oleyl Oleate
Oleyl Stearate
Palm Kernel Alcohol
Palm Kernel Glycerides
Palm Oil Glycerides
PEG-6 Caprylic/Capric Glycerides Hydrogenated Palm Oil Glyceride
Hydrogenated Palm Oil Glycerides
Hydrogenated Palm/Palm Kernel Oil
 PEG-6 Esters
Hydrogenated Polyisobutene
Hydrogenated Soybean Oil Glycendes
Hydrogenated Soy Glyceride
Hydrogenated Tallow Glyceride
Hydrogenated Tallow Glyceride Citrate
Hydrogenated Tallow Glyceride Lactate
Hydrogenated Tallow Glycerides
Hydrogenated Tallow Glycerides Citrate
Hydrogenated Vegetable Glyceride
Hydrogenated Vegetable Glycerides
Hydrogenated Vegetable Glycerides
 Phosphate
Hydroxylated Lanolin
Hydroxyoctacosanyl Hydroxystearate
Isoamyl Laurate
Isobutyl Myristate
Isobutyl Palmitate
Isobutyl Pelargonate
Isobutyl Stearate
Isocetyl Alcohol
Isocetyl Isodecanoate
Isocetyl Palmitate
Isocetyl Stearate
Isocetyl Stearoyl Stearate
Isodecyl Hydroxystearate
Isodecyl Isononanoate
Isodecyl Laurate
Isodecyl Myristate
Isodecyl Neopentanoate
Isodecyl Oleate
Isodecyl Palmitate
Isohexyl Laurate
Isohexyl Palmitate
Isononyl Isononanoate
Isopropyl Isostearate
Isopropyl Lanolate
Isopropyl Laurate
Isopropyl Linoleate
Isopropyl Methoxycinnamate
Isopropyl Myristate
Isopropyl Oleate
Isopropyl Palmitate
Isopropyl Ricinoleate
Isopropyl Stearate
Isopropyl Tallowate
Isostearyl Alcohol
Isostearyl Benzoate
Isostearyl Isostearate
Isostearyl Lactate
Isostearyl Neopentanoate
Isostearyl Palmitate
Isotridecyl Isononanoate
Laneth-9 Acetate
Laneth-10 Acetate
Lanolin
Lanolin Alcohol
Lanolin Oil
Lanolin Wax
Lard Glycerides
PPG-5 Lanoilin Wax Glyceride
PPG-9 Laurate
PPG-4 Lauryl Ether
PPG-3 Myristyl Ether
PPG-4 Myristyl Ether
PPG-26 Oleate
PPG-36 Oleate
PPG-10 Oleyl Ether
PPG-20 Oleyl Ether
PPG-23 Oleyl Ether
PPG-30 Oleyl Ether
PPG-37 Oleyl Ether
PPG-50 Oleyl Ether
PPG-9-Steareth-3
PPG-11 Stearyl Ether
PPG-15 Stearyl Ether

APPENDIX C-continued

| | | |
|---|---|---|
| Methyl Hydroxystearate | PEG-2 Castor Oil | Propylene Glycol Isostearate |
| Methyl Laurate | PEG-3 Castor Oil | Propylene Glycol Hydroxystearate |
| Methyl Linoleate | PEG-4 Castor Oil | Propylene Glycol Laurate |
| Methyl Myristate | PEG-5 Castor Oil | Propylene Glycol Myristate |
| Methyl Oleate | PEG-8 Castor Oil | Propylene Glycol Myristyl Ether |
| Methyl Palmitate | PEG-9 Castor Oil | Propylene Glycol Myristyl Ether Acetate |
| Methyl Pelargonate | PEG-10 Castor Oil | Propylene Glycol Oleate |
| Methyl Ricinoleate | PEG-10 Coconut Oil Esters | Propylene Glycol Ricinoleate |
| Methyl Rosinate | PEG-5 Glyceryl Triisostearate | Propylene Glycol Soyate |
| Methyl Stearate | PEG-5 Hydrogenated Castor Oil | Propylene Glycol Stearate |
| Mineral Oil | PEG-7 Hydrogenated Castor Oil | Silica Silylate |
| Mink Oil | PEG-5 Hydrogenated Corn Glycerides | Soybean Oil Unsaponifiables |
| Myreth-3 Caprate | PEG-8 Hydrogenated Fish Glycerides | Soy Sterol |
| Myreth-3 Laurate | PEG-20 Methyl Glucose Sesquistearate | Soy Sterol Acetate |
| Myreth-3 Myristate | Pentaerythrityl Rosinate | Squalene |
| Myreth-3 Palmitate | Pentaerythrityl Tetraoctanoate | Stearoxytrimethylsilane |
| Myristyl Alcohol | Pentaerythrityl Tetraoleate | Stearyl Acetate |
| Myristyleicosanol | PPG-4-Ceteth-1 | Stearyl Alcohol |
| Myristyleicosyl Stearate | PPG-8-Ceteth-1 | Stearyl Citrate |
| Myristyl Isostearate | PPG-8-Ceteth-2 | Stearyl Lactate |
| Myristyl Lactate | PPG-10 Cetyl Ether | Sucrose Distearate |
| Myristyl Lignocerate | PPG-10 Cetyl Ether Phosphate | Sulfurized Jojoba Oil |
| Myristyl Myristate | PPG-28 Cetyl Ether | Sunflower Seed Oil Glycerides |
| Myristyl Neopentanoate | PPG-30 Cetyl Ether | Tall Oil Glycerides |
| Myristyloctadecanol | PPG-50 Cetyl Ether | Tallow Glyceride |
| Myristyl Propionate | PPG-17 Dioleate | Tallow Glycerides |
| Myristyl Stearate | PPG-3 Hydrogenated Castor Oil | Tridecyl Alcohol |
| Neopentyl Glycol Dicaprate | PPG-30 Isocetyl Ether | Triisocetyl Citrate |
| Neopentyl Glycol Dioctanoate | PPG-5 Lanolate | Triisostearin PEG-6 Esters |
| Nonyl Acetate | PPG-2 Lanolin Alcohol Ether | Trimethylsilylamodimethicone |
| Octyl Acetoxystearate | PPG-5 Lanolin Alcohol Ether | Triolein PEG-6 Esters |
| Octyldodecanol | PPG-10 Lanolin Alcohol Ether | Tris(Tributoxysiloxy)Methylsilane |
| Octyldodecyl Neodecanoate | PPG-20 Lanolin Alcohol Ether | Undecylpentadecanol |
| Octyl Hydroxystearate | PPG-30 Lanolin Alcohol Ether | Vegetable Glycerides Phosphate |
| Octyl Isononanoate | PPG-5 Lanolin Wax | Wheat Germ Glycerides |
| Adenosine Phosphate | Desamido Animal Collagen | Hydrolyzed Human Placental Protein |
| Adenosine Triphosphate | Dicapryloyl Cystine | Hydrolyzed Mucopolysaccharides |
| Alanine | Diethyl Aspartate | Hydrolyzed Silk |
| Albumen | Diethylene Tricaseinamide | Hydrolyzed Soy Protein |
| Aldioxa | Diethyl Glutamate | Hydrolyzed Vegetables Protein |
| Allantoin | Dihydrocholesterol | Hydrolyzed Yeast Protein |
| Allantoin Ascorbate | Dipalmitoyl Hydroxyproline | Hydroxylated Lanolin |
| Allantoin Biotin | Disodium Adenosine Triphosphate | |
| Allantoin Calcium Pantothenate | Dried Buttermilk | Isobutylated Lanolin Oil |
| Allantoin Galacturonic Acid | Dried Egg Yolk | |
| Allantoin Glycyrrhetinic Acid | Egg | |
| Allantoin Polygalacturonic Acid | Egg Oil | Isostearyl Diglyceryl Succinate |
| Aloe | Egg Yolk | Keratin |
| Animal Collagen Amino Acids | Egg Yolk Extract | Laneth-4 Phosphate |
| Animal Elastin Amino Acids | Ethyl Aspartate | Laneth-5 |
| Animal Keratin Amino Acids | Ethyl Ester of Hydrolyzed Animal Protein | |
| Arginine | Ethyl Glutamate | Lanosterol |
| Asparagine | Ethyl Serinate | Lard Glycerides |
| Aspartic Acid | Ethyl Urocanate | |
| C10–11 Isoparaffin | PPG-9 | PPG-16 Butyl Ether |
| C10–13 Isoparaffin | PPG-12 | PPG-18 Butyl Ether |
| C11–12 Isoparaffin | PPG-15 | PPG-22 Butyl Ether |
| C11–13 Isoparaffin | PPG-17 | PPG-24 Butyl Ether |
| C12–14 Isoparaffin | PPG-20 | PPG-30 Butyl Ether |
| Camphor | PPG-26 | PPG-33 Butyl Ether |
| Glyceryl Lanolate | PPG-30 | PPG-40 Butyl Ether |
| Glycine | PPG-34 | PPG-53 Butyl Ether |
| Glycogen | PPG-2-Buteth-3 | PPG-2 Isostearate |
| | PPG-3-Buteth-5 | PPG-10 Methyl Glucose Ether |
| Hexamethyldisiloxane | PPG-5-Buteth-7 | PPG-20 Methyl Glucose Ether |
| Hexyl Nicotinate | PPG-7-Buteth-10 | PPG-20 Methyl Glucose Ether Acetate |
| | PPG-9-Buteth-12 | PPG-2 Myristyl Ether Propionate |
| Human Placental Protein | PPG-12-Buteth-16 | Pregnenolone Acetate |
| Hyaluronic Acid | PPG-15-Buteth-20 | Tocopheryl Acetate |
| Hydrogenated Animal Glyceride | PPG-20-Buteth-30 | Tocopheryl Linoleate |
| Hydrogenated Honey | PPG-24-Buteth-27 | Tocopheryl Nicotinate |
| Hydrogenated Palm Oil | PPG-26-Buteth-26 | Tocopheryl Succinate |
| Hydrogenated Tallow Betaine | PPG-28-Buteth-35 | Tridecyl Salicylate |
| Hydrogenated Tallowtrimonium Chloride | PPG-33-Buteth-45 | Tridecyl Stearate |
| Hydrogenated Laneth-5 | PPG-4 Butyl Ether | Tryptophan |
| Hydrolyzed Animal Elastin | PPG-5 Butyl Ether | Tyrosine |
| Hydrolyzed Animal Keratin | PPG-9 Butyl Ether | Undecylenyl Alcohol |
| Hydrolyzed Animal Protein | PPG-14 Butyl Ether | Undecylpentadecanol |
| Hydrolyzed Casein | PPG-15 Butyl Ether | Uric Acid |

APPENDIX C-continued

Whey Protein
Whole Dry Milk
Witch Hazel Distillate
Witch Hazel Extract
Linoleic Acid
Linolenic Acid
Orotic Acid Norvaline
Serum Albumin
Serum Proteins
Silk
Acetylated Castor Oil
Acetylated Glycol Stearate
Acetylated Hydrogenated Cottonseed
  Glyceride
Acetylated Hydrogenated Lard Glyceride
Acetylated Hydrogenated Tallow Glyceride
Acetylated Hydrogenated Tallow Glycerides
Acetylated Hydrogenated Vegetable Glyceride
Apricot Kernol Oil
Avocado Oil
Avocado Oil Unsaponifiables
Batyl Alcohol
Batyl Isostearate
Batyl Stearate
Bayberry Wax
Bisphenylhexamethicone
Butter
C18–36 Acid Triglyceride
C30–46 Piscine Oil
C10–18 Triglycerides
Caprylic/Capric/Isostearic/Adipic
  Triglycerides
Caprylic/Capric/Lauric Triglyceride
Caprylic/Capric/Linoleic Triglyceride
Caprylic/Capric/Stearic Triglyceride
Caprylic/Capric Triglyceride
Castor Oil
Chaulmoogra Oil
Cherry Pit Oil
Cocoa Butter
Coconut Oil
Cod Liver Oil
Corn Oil
Cottonseed Oil
Dihydrogenated Tallow Phthalate
Diisostearyl Dilinoleate
Diinoleic Acid
Dimethicone
Dioctyl Dilinoleate
Ditridecyl Dilinoleate
Egg Oil
Erucyl Arachidate
Erucyl Erucate
Ethiodized Oil
Glyceryl Tribehenate
Glycol Dibehenate
Grape Seed Oil
Hazel Nut Oil
Hexadecyl Methicone
Hexanediol Distearate
Hybrid Safflower Oil
Hydrogenated C6–14 Olefin Polymers
Hydrogenated Castor Oil
Hydrogenated Coconut Oil
Hydrogenated Cottonseed Oil
Hydrogenated Jojoba Oil
Hydrogenated Jojoba Wax
Hydrogenated Lanolin
Hydrogenated Lard
Hydrogenated Menhaden Oil
Hydrogenated Palm Kernel Oil
Hydrogenated Palm Oil
Hydrogenated Peanut Oil Pyridoxine Dicaprylate
Pyridoxine Dilaurate
Pyridoxine Dioctenoate
Pyridoxine Dipalmitate
PEG-5 Hydrogenated Lanolin
PEG-10 Hydrogenated Lanolin
PEG-2 Milk Solids
PEG-6 Soya Sterol Undecylenate
Phenylalanine
Polyglyceryl-2 Lanolin Alcohol Ether
Sulfurized Jojoba Oil
Tall Oil Sterol
Acetylated Lanolin
Acetylated Lanolin Alcohol
Acetylated Lanolin Ricinoleate
Acetylated Lard Glyceride
Acetylated Palm Kernal Glycerides
Acetylated Sucrose Distearate Hydrogenated Rice Bran Wax
Hydrogenated Shark Liver Oil
Hydrogenated Soybean Oil
Hydrogenated Tallow
Hydrogenated Vegetable Oil
Isobutylated Lanolin Oil
Isostearyl Erucate
Isostearyl Stearoyl Stearate
Jojoba Butter
Jojoba Oil
Jojoba Wax
Lanolin Linoleate
Lanolin Ricinoleate
Lard
Lauryl Stearate
Linseed Oil
Menhaden Oil
Methicone
Mineral Oil
Mink Oil
Mink Wax
Moringa Oil
Neatsfoot Oil
Octyldodecyl Myristate
Octyldodecyl Stearate
Octyldodecyl Stearoyl Stearate
Oleostearine
Oleyl Lanolate
Oleyl Linoleate
Olive Husk Oil
Olive Oil
Olive Oil Unsaponifiables
Palm Kernel Oil
Palm Oil
Paraffin
Peach Kernel Oil
Peanut Oil
Pengawar Djambi Oil
Pentadesma Butter
Pentaerythrityl Hydrogenated Rosinate
Pentaerythrityl Tetraabietate
Pentaerythrityl Tetrabehenate
Pentaerythrityl Tetrastearate
Pentahydrosqualene
Petrolatum
Phenyl Trimethicone
Pristane
Propylene Glycol Dicaprylate
Propylene Glycol Dicaprylate/Dicaprate
Propylene Glycol Dicocoate
Propylene Glycol Dilaurate
Propylene Glycol Dioctanoate
Propylene Glycol Dipelargonate
Propylene Glycol Distearate Urocanic Acid
Vegatable Oil
Retinyl Acetate
Retinyl Palmitate
Ribonucleic Acid Methionine
2-Methyl-4-Hydroxypyrrolidine
Milk
Pyridoxine Tripalmitate
Resorcinol Acetate Propylene Glycol Diundecanoate
Rapeseed Oil
Rapeseed Oil Unsaponifiables
Rice Bran Oil
Rice Bran Wax
Safflower Oil
Sesame Oil
Shark Liver Oil
Shea Butter
Shea Butter Unsaponifiables
Shellac Wax
Soybean Oil
Soybean Oil Unsaponifiables
Soy Sterol Acetate
Squalane
Stearoxy Dimethicone
Stearyl Caprylate
Stearyl Caprylate/Caprate
Stearyl Erucate
Stearyl Heptanoate
Stearyl Octanoate
Stearyl Stearate
Stearyl Stearoyl Stearate
Sunflower Seed Oil
Sweet Almond Oil
Synthetic Jojoba Oil
Synthetic Wax
Tall Oil
Tallow
Tallow Glycerides
Tricaprin
Trihydroxystearin
Triisononanon
Triisopropyl Trilinoleate
Triisostearin
Triisostearyl Trilinoleate
Trilaurin
Trilauryl Citrate
Trilinoleic Acid
Trilinolein
Trimethylolpropane Triisostearate
Trimethylolpropane Trioctanoate
Trimethyloxysilicate
Trimyristin
Trioctyl Citrate
Triolein
Trioleyl Phosphate
Tripalmitin
Tristearin
Tristearyl Citrate
Vegetable Oil
Walnut Oil
Wheat Bran Lipids
Wheat Germ Oil

What is claimed is:

1. A topically active composition comprising:
   (a) about 0.001% to about 5%, by weight, of a topically active compound;
   (b) about 0.1% to about 15%, by weight, of an anionic surfactant;
   (c) about 0.5% to about 35%, by weight, of a hydrotrope;
   (d) about 0.5% to about 25%, by weight, of a water-soluble hydric solvent;
   (e) 0% to about 5%, by weight, of a cosurfactant selected from the group consisting of a nonionic surfactant, an ampholytic surfactant, and mixtures thereof; and
   (f) water,
   wherein the topically active compound is present in the composition in an amount of at least 50% of saturation concentration, when measured at room temperature, and the topically active compound is water-insoluble and is selected from the group consisting of an antidandruff agent, a sunscreen, a medicament, a skin conditioner, a hair conditioner, a vitamin, an emollient, an antioxidant, a fragrance, an antiacne agent, a skin protectant, an external analgesic, an ultraviolet light absorber, and mixtures thereof,
   and wherein upon dilution of one weight part of the composition with 0.33 to 3 parts of water, by weight, a phase separation is observed within one hour.

2. The composition of claim 1 wherein the topically active compound is present in an amount of at least 75% of saturation concentration.

3. The composition of claim 1 comprising about 0.01% to about 1.5% by weight, of the topically active compound.

4. The composition of claim 1 wherein the surfactant is present in an amount of about 0.3% to about 8%, by weight of the composition.

5. The composition of claim 1 wherein the anionic surfactant comprises a $C_8$–$C_{18}$ alkyl sulfate, a $C_8$–$C_{18}$ fatty acid salt, a $C_8$–$C_{18}$ alkyl ether sulfate having one or two moles of ethoxylation, a $C_8$–$C_{18}$ alkamine oxide, a $C_8$–$C_{18}$ alkyl sarcosinate, a $C_8$–$C_{18}$ sulfoacetate, a $C_8$–$C_{18}$ sulfosuccinate, a $C_8$–$C_{18}$ alkyl diphenyl oxide disulfonate, a $C_8$–$C_{18}$ alkyl carbonate, a $C_8$–$C_{18}$ alpha-olefin sulfonate, a methyl ester sulfonate, and mixtures thereof.

6. The composition of claim 1 wherein the hydrotrope is present in an amount of about 3% to about 30% by weight.

7. The composition of claim 1 wherein the hydric solvent present in an amount of about 2% to about 20% by weight.

8. The composition of claim 1 wherein the hydric solvent comprises an alcohol, a diol, a triol, and mixtures thereof.

9. The composition of claim 1 wherein the hydrotrope is selected from the group consisting of sodium cumene sulfonate, ammonium cumene sulfonate, ammonium xylene sulfonate, potassium toluene sulfonate, sodium toluene sulfonate, sodium xylene sulfonate, toluene sulfonic acid, xylene sulfonic acid, sodium polynaphthalene sulfonate, sodium polystyrene sulfonate, sodium methyl naphthalene sulfonate, disodium succinate, and mixtures thereof.

10. The composition of claim 1 having a pH of about 5 to about 8.

11. The composition of claim 1 comprising about 0.01% to about 0.5%, by weight, of a nonionic surfactant, an ampholytic surfactant, or a mixture thereof.

12. The composition of claim 1 comprising about 0.001% to about 5.0% of a water-insoluble topically active compound, about 5% to about 15% dipropylene glycol, about 10% to about 20% sodium xylene sulfonate, about 0.5% to about 5% ammonium lauryl sulfate, and 0% to about 5% cocamidopropylbetaine.

13. A method of cleaning a surface and depositing a topically active compound on the surface comprising contacting the surface with a composition of claim 1, then rinsing the composition from the surface.

14. The method of claim 13 wherein the surface is a skin or hair of a mammal.

15. The method of claim 13 wherein the surface is a hard, inanimate surface.

* * * * *